(12) United States Patent
Foung et al.

(10) Patent No.: US 7,091,324 B2
(45) Date of Patent: Aug. 15, 2006

(54) PREVENTION AND TREATMENT OF HCV INFECTION EMPLOYING ANTIBODIES DIRECTED AGAINST CONFORMATIONAL EPITOPES

(75) Inventors: Steven K. H. Foung, Stanford, CA (US); Kenneth G. Hadlock, San Francisco, CA (US); Zhen-yong Keck, Redwood City, CA (US)

(73) Assignee: Board of Trustees of Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/728,720

(22) Filed: Dec. 1, 2000

(65) Prior Publication Data

US 2006/0104980 A1 May 18, 2006

Related U.S. Application Data

(63) Continuation-in-part of application No. 09/430,489, filed on Oct. 29, 1999, now Pat. No. 6,692,908, which is a continuation-in-part of application No. 09/187,057, filed on Nov. 5, 1998, now abandoned.

(51) Int. Cl.
*C07K 16/10* (2006.01)
(52) U.S. Cl. .............. 530/388.3; 530/388.15; 530/387.3; 530/389.4
(58) Field of Classification Search .......... 530/388.3, 530/388.1, 388.15, 387.3, 389.4; 435/5, 435/339; 424/142.1, 149.1, 133.1, 141.1, 424/147.1, 159.1
See application file for complete search history.

(56) References Cited

U.S. PATENT DOCUMENTS

| | | | |
|---|---|---|---|
| 4,376,110 A | 3/1983 | David et al. ............ 436/513 |
| 4,415,491 A | 11/1983 | Vyas .................. 260/112.5 |
| 4,683,136 A | 7/1987 | Milich et al. ............. 424/89 |
| 5,106,726 A | 4/1992 | Wang ..................... 435/5 |
| 5,308,750 A * | 5/1994 | Mehta et al. .............. 435/5 |
| 5,350,671 A | 9/1994 | Houghton et al. ........... 435/5 |
| 5,514,539 A | 5/1996 | Bukh et al. ............... 435/5 |
| 5,574,132 A | 11/1996 | Lacroix ................. 530/323 |
| 5,670,153 A | 9/1997 | Weiner et al. .......... 424/189.1 |
| 5,695,390 A | 12/1997 | Mizuno et al. ........... 451/124 |
| 5,709,995 A | 1/1998 | Chisari et al. ............. 435/5 |
| 5,756,312 A | 5/1998 | Weiner et al. .......... 435/69.3 |
| 5,843,639 A | 12/1998 | Reyes et al. ............... 435/5 |
| 5,871,962 A | 2/1999 | Bukh et al. ............ 435/69.1 |
| 5,985,609 A | 11/1999 | Min et al. ............. 435/69.3 |
| 6,020,122 A | 2/2000 | Okasinski et al. ........... 435/5 |
| 6,020,167 A | 2/2000 | Thoma ................. 435/69.3 |
| 6,027,729 A | 2/2000 | Houghton et al. ........ 424/228.1 |
| 6,074,846 A | 6/2000 | Ralston et al. .......... 435/69.3 |
| 6,110,706 A | 8/2000 | Thoma ................. 435/69.3 |
| 6,121,020 A | 9/2000 | Selby et al. ............ 435/69.3 |
| 6,538,114 B1 * | 3/2003 | Persson et al. |

FOREIGN PATENT DOCUMENTS

| | | |
|---|---|---|
| WO | WO 97/40176 | * 10/1997 |
| WO | WO 99/24054 | 11/1998 |
| WO | WO 00/26418 | 5/2000 |

OTHER PUBLICATIONS

Burioni et al., Dissection of Human Humoral Immune Response Against Hepatitis C Virus E2 Glycoprotein by Repertoire Cloning and Generation of Recombinant Fab Fragments. Hepatology 28(3):810-814, 1998.*
Mondelli et al., Significance of the Immune Response to a Major, Conformational B-Cell Epitope on the Hepatitis C Virus NS3 Region Defined by a Human Monoclonal Antibody. Journal of Virology 68(8): 4829-4836, 1994.*
Deleersnyder et al., Formation of Native Hepatitis C Virus Glycoprotein Complexes. Journal of Virology 71(1):697-704, 1997.*
Da Silva Cardoso et al., Isolation and Characterization of Human Monoclonal Antibodies Against Hepatitis C Virus Envelope Glycoproteins. Journal of Medical Virology 55:28-34, 1998.*
Habersetzer et al., Isolation of human monoclonal antibodies (HMabs) directed at conformational determinants of the heptitis C virus (HCV) E2 envelope protein. Hepatology 24(4), Pt. 2, 381A, Abstract 1020, 1996.*
Abrignani, S., "Immune Responses Throughout Hepatitis C Virus (HCV) Infection: HCV from the Immune System Point of View", *Springer Semin Immunopathol*, 19: 47-55, 1997.
Akatsuka, et al., "B-Cell Epitopes on the Hepatitis C Virus Nucleocapsid Protein Determined by Human Monospecific Antibodies", *Hepatology*, 18: 503-510, 1993.
Burioni, et al., "Dissection of Human Humoral Immune Response Against Hepatitis C Virus E2 Glycoprotein by Repertorie Cloning and Generation of Recombinant Fab Fragments", *Hepatology*, 28: 810-814, 1998.
Burton and Barbas, et al., "Human Antibodies from Combinatorial Libraries", *Advances in Immunology*, 57:191-280.
da Silva Cardosa, et al., "Isolation and Characterization of Human Monoclonal Antibodies Against Hepatitis C Virus Envelope Glycoproteins", *J. Med. Virology*, 55: 28-34, 1998.

(Continued)

*Primary Examiner*—Mary E. Mosher
(74) *Attorney, Agent, or Firm*—Choate, Hall & Stewart LLP; Brenda Hershbach Jarrell; C. Hunter Baker

(57) ABSTRACT

Conformational epitopes of the envelope protein E2 of the Hepatitis C virus (HCV) have been identified and characterized using a panel of monoclonal antibodies derived from patients infected with HCV. These conformational epitopes have been determined to be important in the immune response of humans to HCV and may be particularly important in neutralizing the virus. Based on the identification of these conformational epitopes, vaccines containing peptides and mimotopes with these conformational epitopes intact may be prepared and administered to patients to prevent and/or treat HCV infection. The identification of four distinct groups of monoclonal antibodies with each directed to a particular epitope of E2 may be used to stratify patients based on their response to HCV and may be used to determine a proper treatment regimen.

26 Claims, 35 Drawing Sheets

OTHER PUBLICATIONS

DeLalla, et al., "Properties of a Human Monoclonal Antibody Specific for the NS4 Region of Hepatitis C Virus", *J. Hepatol.* 18:163-167, 1993.

Deleersnyder et al., "Formation of Native Hepatitis C Virus Glycoprotein Complexes", *J. Virology*, 71:697-704, 1997.

Foung, et al., "Rescue of Human Monoclonal Antibody Production from an EBV-Transformed B Cell Line by Fusion to a Human-Mouse Hybridoma", *J. Immunol. Methods*, 701:83-90, 1990.

Habersetzer, et al., "Characterization of Human Monoclonal Antibodies Specific to the Hepatitis C Virus Glycoprotein E2 with In Vitro Binding Neutralization Properties", *Virology*, 249: 32-41, 1998.

Hadlock, et al., "Neutralizing Human Monoclonal Antibodies to Conformational Epitopes of Human T-Cell Lymphotropic Virus Type 1 and 2 gp46", *J. Virology*, 71:5828-5840, 1997.

Landford, et al., "Analysis of Hepatitis C Virus Capsid, E1, and E2/NS1 Proteins Expressed in Insect Cells", *Virology*, 197: 225-235, 1993.

Mahaney, et al., "Genotypic Analysis of Hepatitis C Virus in American Patients", *Hepatology*, 20: 1405-1411, 1994.

Meola, et al., Derivation of Vaccines from Mimotopes, Immunologic Properties of Human Hepatitis B Virus Surface Antigen Mimotopes Displayed on Filamentous Phage, *J. Immunol.* 154:3162-3172, 1995.

Mondelli, et al., "Significance of the Immune Response to a Major, Conformational B-Cell Epitope on the Hepatitis C Virus NS3 Region Defined by a Human Monoclonal Antibody", *J. Virol.* 68:4829-4836, 1994.

Moradpour, et al., "Characterization of Three Novel Monoclonal Antibodies Against Hepatitis C Virus Core Protein", *J. Med. Virol.* 48:234-241, 1996.

Plaisant et al., "Human Monoclonal Recombinant Fabs Specific for HCV Antigens Obtained by Repertoire Cloning in Phage Display Combinatorial Vectors", *Res. Virol.* 148:-169, 1997.

Puntoriero, et al., "Towards a Solution for Hepatitis C Virus Hypervariability: Mimotopes of the Hypervariable Region 1 Can Induce Antibodies Cross-Reacting with a Large Number of Viral Variants", *EMBO J.* 17:3521-3533, 1998.

Ralston, et al., "Characterization of Hepatitis C Virus Envelope Glycoprotein Complexes Expressed by Recombinant Vaccinia Viruses", *J. Virology*, 67:6753-6761, 1993.

Rosa, et al., "A Quantitative Test to Estimate Neutralizing Antibodies to the Hepatitis C Virus: Cytofluorimetric Assessment of Envelope Glycoprotein 2 Binding to Target Cells", *PNAS USA*, 93:1759-1763, 1996.

Siemoneit, et al., "Isolation and Eptiope Characterization of Human Monoclonal Antibodies to Hepatitis C Virus Core Antigen", *Hybridoma*, 13:9-13, 1994.

Siemoneit, et al., "Human Monoclonal Antibodies for the Immunological Characterization of a Highly Conserved Protein Domain of the Hepatitis C Virus Glycoprotein E1" *Clin. and Experimental Immun.* 101:278-283, 1995.

Simmonds, "Variability of Hepatitis C Virus", *Hepatology*, 21:570-583, 1995.

Tafi, et al, "Identification of HCV Core Mimotopes: Improved Methods for the Selection and Use of Disease-Related Phage-Displayed Peptides", *Biol. Chem.* 378:495-502, 1997.

Ward, et al., "Stringent Chemical and Thermal Regulation of Recombinant Gene Expression by Vaccinia Virus Vectors in Mammalian Cells", *Proc. N.H. Acad. Sci., USA*, 92: 6773-6777, 1995.

Zimmerman, et al., "Efficient Hybridization of Mouse-Human Cell Lines by Means of Hypo-Osmolar Electrofusion", *J. Immunol. Methods.* 134: 43-50, 1990.

International Search Report issued for corresponding PCT application PCT/US01/45029, 2003.

Chan, S-W, et al., "Human recombinant antibodies specific for hepatitis C virus core and envelope E2 peptides from an immune phage display library", *Journal of General Virology*, 77:251-2539, 1996.

Database EMBL Online retrieved from EBI Database accession No. Q81497, XP002222487 abstract, 1996.

Hadlock, K.G. et al, Human Monoclonal Antibodies That Inhibit Binding Of Hepatitis C Virus E2 Protein to CD81 and Recognize Conserved Conformational Epitopes, *J. Virology*, 74:10407-10416, 2000.

Prince, A. et al., Visualization of hepatitis C virions and putative defective interfering particles isolated from low-density lipoproteins, *Journal of Viral Hepatitis*, 3:11-17, 1996.

* cited by examiner

HCV E2 proteins detected with mMAb E2G

Sequences amplified from central region of HCV E2 vaccinia virus clones

>hcv-1a3, (Q1a)
CTCAACTGGATTCACCAAAGTGTGCGGAGCGCCCCCTGTGTCATCGGAGGGGCGGG
CAACAACACCTT        GCGCTGCCCCACTGTTGTTTCCGCAAGCATCCGGAAGCCAC
GTACTCTCGGTGCGGCTCCGGTCCCTGGATTACGCCCAGGTGCCTGGTc >hcv-1b8, (Q1b)
TGGCACAGGGTTCACCAAGAGCGTGTGGGGCCCCCATGTAACATCGGGGGGGTCGG
CAATAACACCTT        GACTTGCCCCACGGACTGTTTCCGGAAGCACCCGAGGCCAC
TACCAAAATGTGGTTCGGGGCCTTGGCTGACACCTAGGTGCATAGTt >hcv-2a-25, (Q2a)
CTCCACTGT TTCACCAAAAACTTGCGGCGGCACCACCCCTGCCGCATCAGAGCTGACTT
TAATGCCAGCACggaCCTGTGTGCCCCACGGACTGTTTCAGGAAGCATCCTGAAGCCAC
TTACATCAAAATGTGGCTCTGCCCCctgtgacgccaaagtgcctgata >HCV-2B-1, (Q2b)
TGGGACTGGGTTCACTAAGACATGCGGTGCACCACCTTGCCGCATTAGGAGGGACTG
CAACGGAACCCTcgaCCTATTGTGCCCACAGACTGTTTCAGAAAGCACCCAGATACTAC
CTACCTTAAGTGTGGAGCGCCCTTGGTTGACCCCAAATGCATGGTa

FIG. 2

| Name | Sequences | | | | | | |
|---|---|---|---|---|---|---|---|
| HCV-1a | CTCAACTGGA | TTCACCAAAG | TGTGCGGAGC | GCCTCCTTGT | GTCATCGGAG | GGGCGGGCAA | |
| HCV-Q1a-FR | TAGT....G | .......T..GA | ......C... | ...C..C.. | ......AA.. | .....G.... | ...TC..T.. |
| HCV-1b | TGGC...A..G | .........GA | C...T..G.. | C..C..G..A | ......AA.. | .....G.... | ...TC..... |
| HCV-Q1b-FR | ...C...C | .A......GA | ......CT.. | A..A..C..C | ...CG...TA | .....TA... | CT.ACTT... |
| HCV-2a | ...C...-T | ..........A | ......CT.. | A..A..C..C | ...CG....A | .....A.... | CT.ACTTT.. |
| HCV-Q2a-FR | ...GGG.....G | .........T..GA | ......CA.. | A..A......C | ...CG...TA.GA | .....AA.ACTA.. | |
| HCV-2b | TGGG.....G | .........T..GA | ......CA.. | A..A......C | ...CG...TA.GA | .....TA.GA | ...ACT.... |
| HCV-Q2b-FR | | | | | | | |
| HCV-1a | CAACACC--- | ---CTGCACT | GCCCCACTGA | TTGCTTCCGC | AAGCATCCGG | ACGCCACATA | |
| HCV-Q1a-FR | ........... | .....T..G.. | ........... | ...T....... | .......C.C. | ......A.... | ......G... |
| HCV-1b | ..CG....... | .....T..AT. | ......G... | ...C..T... | .......C.C. | ........... | ...G..T..T.. |
| HCV-Q1b-FR | T.......... | .....T..ACT | ......G... | ...C..T... | .......C.C. | ....T...... | ...G......T.. |
| HCV-2a | TGC..G.ATG | GACT...TTG. | ......G... | ...C..T..TA.G | .......T... | ...TA....C. | |
| HCV-Q2a-FR | TGC..G.ACG | GAC....TG. | ......A... | ...C..T..A.G | .......T... | ...A......T.. | |
| HCV-2b | ..G....TATC | GATT.ATTG. | ........... | ...C..T..TA.G | .......C.A. | ...T..T..C. | |
| HCV-Q2b-FR | .GGA....CTC | GAC..ATTG. | ......A... | ...C..T..A.A | .....?..C.A. | ...TA.T..C. | |

FIG. 3A

```
Name             Sequences
HCV-1a       CTCTCGGTGC GGCTCCGGTC CCTGGATCAC ACCCAGGTGC CTGGTC
HCV-Q1a-FR   .......... .......... .......T.. G......... ......
HCV-1b       .A.AAAA..T .....G..G. .....T.G.. ...T...... ..A..A
HCV-Q1b-FR   .A.CAAA..T ..T..G..G. .T...C.G.. ...T...... A.A..T
HCV-2a       .ATCAAA..T .....T..G. .....C.... G..A...... ...A..
HCV-Q2a-FR   .ATCAAA..T .....T..G. ..CT.-.G.. G..A.A.... ...A.A
HCV-2b       TCT.AA...T ..AG.A..G. .T...T.A.. T......... .....A
HCV-Q2b-FR   .CT.AA...T ..AG.G..G. .T...T.G.. C....AA... A....A +--HCV-2B-1.C
                                            +-----7
                                            !     +--hcv-2B,
     One most parsimonious tree found:  +-----6
                                        !   !     +--hcv-2a-25.
                                        !   +-----5
                                     +--4         +--HCV-2A,
                                     !  !
                                     !  !         +--hcv-1b8.se
                                  +--2  +---------3
                                  !  !            +--HCV-1B,
                                --1  !
                                  !  +---------------HCV-Q1a
```

FIG. 7

Competition Assays

- Biotinylated test Ab
- Streptavidin AP conjugate
- HCV E2
- Competing HMAb
- GNA

- Coat plates with GNA lectin
- Capture full-length intracellular E2 onto microtiter plate by binding CHO moieties to GNA lectin
- Mix competing HMAb with GNA-captured E2
- Add biotinylated test HMAb. Detect binding of biotinylated test HMAb to E2 with streptavidin-AP conjugate
- Inhibition of binding of test HMAb suggests epitopes within same antibody binding domain

FIG. 20

Summary of HMAb Competition Analysis

| Competitor Grp | HMAb | E2 | GROUP I | | | | | GRP II | GROUP III | |
|---|---|---|---|---|---|---|---|---|---|---|
| | | | CBH 2 | CBH 5 | CBH 8C | CBH 11 | CBH 7 | CBH 4G | CBH 4B |
| I | CBH 2 | 1a | 18 | 39 | 51 | ND | 93 | 66 | 76 |
| | | 1b | 17 | 50 | 50 | 48 | 91 | 84 | 84 |
| | CBH 8E | 1a | 13 | 39 | 48 | ND | 79 | 63 | 80 |
| | | 1b | 23 | 45 | 57 | 51 | 91 | 87 | 78 |
| | CBH 5 | 1a | 17 | 9 | 22 | ND | 71 | 60 | 74 |
| | | 1b | 4 | 7 | 24 | 9 | 77 | 76 | 80 |
| | CBH 8C | 1a | 27 | 48 | 25 | ND | 85 | 74 | 84 |
| | | 1b | 11 | 23 | 33 | 23 | 84 | 87 | 86 |
| | CBH 11 | 1a | 96 | 93 | 84 | ND | 97 | 72 | 87 |
| | | 1b | 24 | 25 | 43 | 25 | 82 | 97 | 83 |
| II | CBH 7 | 1a | 40 | 42 | 45 | ND | 2 | 251 | 11 |
| | | 1b | 104 | 104 | 89 | 92 | 2 | 146 | 36 |

FIG. 22A

| | | | | | | | | |
|---|---|---|---|---|---|---|---|---|
| | XTL U68 | 1a | 60 | 63 | 108 | ND | 0 | 1 | 2 |
| | | 1b | 39 | 57 | 73 | 66 | 0 | 23 | 9 |
| III | CBH 4G | 1a | 107 | 95 | 85 | ND | 112 | 40 | 68 |
| | | 1b | 87 | 83 | 81 | 87 | 114 | 40 | 44 |
| | CBH 4B | 1a | 92 | 92 | 87 | ND | 85 | 24 | 29 |
| | | 1b | 78 | 93 | 66 | 81 | 63 | 34 | 13 |
| | CBH 4D | 1a | 98 | 86 | 90 | ND | 135 | 37 | 58 |
| | | 1b | 91 | 82 | 76 | 87 | 102 | 45 | 37 |
| IV | CBH 17 | 1a | 94 | 87 | 87 | ND | 114 | 102 | 103 |
| | | 1b | 73 | 101 | 88 | 95 | 92 | 89 | 64 |
| C | R04 | 1a | 98 | 91 | 92 | ND | 101 | 92 | 98 |
| | | 1b | 96 | 104 | 104 | 101 | 99 | 120 | 101 |

Scale: >140%  60%–140%  30%–59%  10%–29%  <10%

FIG. 22B

Results are the mean percent binding of test antibody relative to wells without any competing antibody. Results are the mean values obtained from 2–5 separate experiments. Both genotype 1a and 1b E2 proteins were tested. ND = not done.

HCV E2 Deletion Constructs sf1b
pDN-411
pDN-447
pDN-470
pDC-644
pDC-579
pDNH-411
sfH1a 384  483  583  661

FIG. 23

HCV E2 Deletion Constructs

HCV 1b E2 w or w/o HVR-1
- sf1b E2
- pDN411
- HEK 293

HCV H1a E2 w or w/o HVR-1
- sfH1a E2
- pDNH-411
- HEK 293

HCV antibodies: CBH 2, CBH 8E, CBH 5, CBH 8C, CBH 11, CBH 7, XTL U68, CBH 4G, CBH 4B, CBH 4D, CBH 17, 3/11, HA, c-myc, R04

FIG. 25A

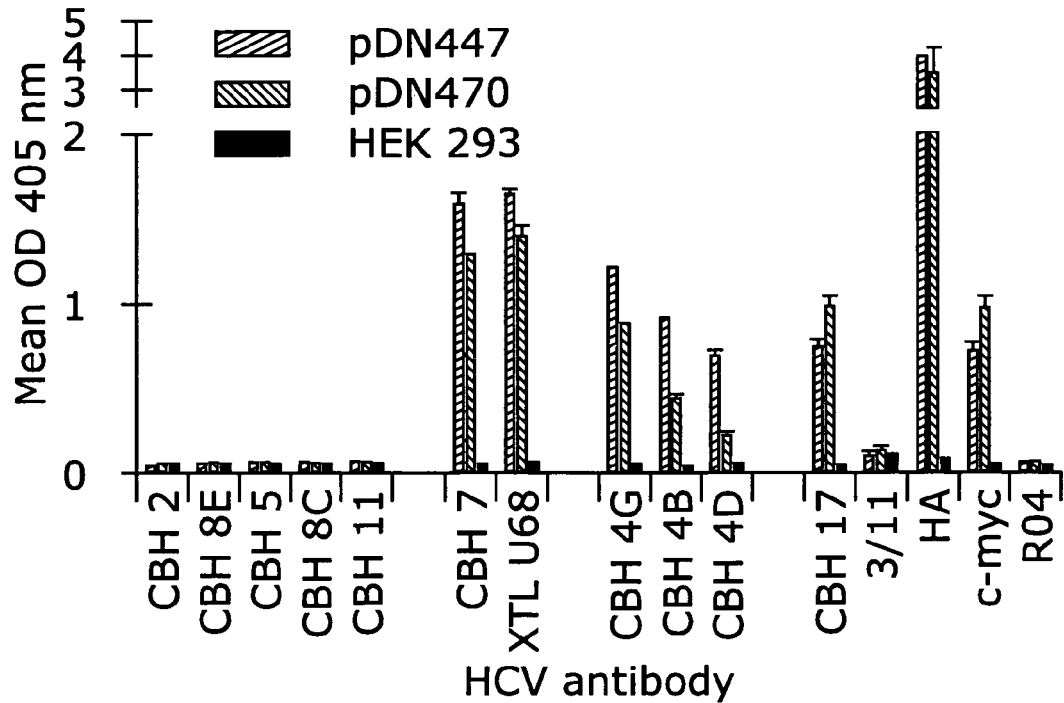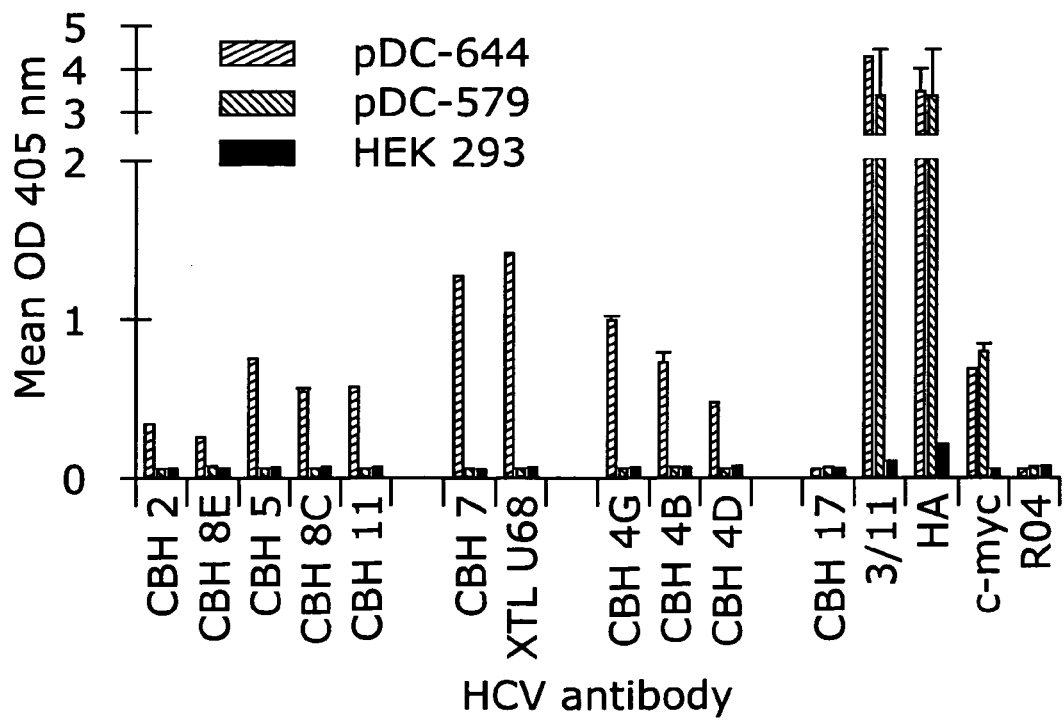
FIG. 25B

SEQUENCE LISTING

<160> NUMBER OF SEQ ID NOS: 35

<210> SEQ ID NO 1
<211> LENGTH: 160
<212> TYPE: DNA
<213> ORGANISM: Hepatitis C Virus

<400> SEQUENCE: 1
ctcaactgga ttcaccaaag tgtgcggagc gcctccttgt gtcatcggag gggcgggcaa      60
caacaccctg cactgcccca ctgattgctt ccgcaagcat ccggacgcca catactctcg     120

```
gtgcggctcc ggtccctgga tcacacccag gtgcctggtc                           160

<210> SEQ ID NO 2
<211> LENGTH: 160
<212> TYPE: DNA
<213> ORGANISM: Hepatitis C Virus

<400> SEQUENCE: 2
ctcaactgga ttcaccaaag tgtgcggagc gccccctgt gtcatcggag gggcgggcaa      60
caacaccttg cgctgcccca ctgattgttt ccgcaagcat ccggaagcca cgtactctcg    120
gtgcggctcc ggtccctgga ttacgcccag gtgcctggtc                          160

<210> SEQ ID NO 3
<211> LENGTH: 160
<212> TYPE: DNA
<213> ORGANISM: Bovine Pancreatic Ribonuclease A

<400> SEQUENCE: 3
tagtactggg ttcactaaga cgtgcggagg ccccccgtgt aacatcgggg gggtcggtaa     60
ccgcaccttg atctgcccca cggactgctt ccggaagcac cccgaggcta cttacacaaa   120
atgtggctcg gggccctggt tgacacctag gtgcctagta                          160

<210> SEQ ID NO 4
<211> LENGTH: 160
<212> TYPE: DNA
<213> ORGANISM: T7 Bacteriophage

<400> SEQUENCE: 4
tggcacaggg ttcaccaaga cgtgtggggc ccccccatgt aacatcgggg gggtcggcaa     60
taacaccttg acttgcccca cggactgttt ccggaagcac cccgaggcca cttacaccaa   120
atgtggttcg gggccttggc tgacacctag gtgcatagtt                          160

<210> SEQ ID NO 5
<211> LENGTH: 166
<212> TYPE: DNA
<213> ORGANISM: Bacterial Protein

<400> SEQUENCE: 5
ctccactggc tacaccaaga cttgcggcgc accaccctgc cgcattagag ctgacttcaa     60
tgccagcatg gacttgttgt gccccacgga ctgttttagg aagcatcctg ataccaccta   120
catcaaatgt ggctctgggc cctggctcac gccaaggtgc ctgatc                   166

<210> SEQ ID NO 6
<211> LENGTH: 167
<212> TYPE: DNA
<213> ORGANISM: Artificial Sequence
<220> FEATURE:
<223> OTHER INFORMATION: Description of Artificial Sequence:Synthetic

<400> SEQUENCE: 6
ctccactgtt tcaccaaaac ttgcggcgca ccaccctgcc gcatcagagc tgactttaat     60
gccagcacgg acctgctgtg ccccacggac tgtttcagga agcatcctga agccacttac   120
atcaaatgtg gctctgggcc cccctgtga cgccaaagtg cctaata                   167

<210> SEQ ID NO 7
<211> LENGTH: 166
<212> TYPE: DNA
<213> ORGANISM: Artificial Sequence
```

```
<220> FEATURE:
<223> OTHER INFORMATION: Description of Artificial Sequence:Synthetic

<400> SEQUENCE: 7
cgggactggg ttcactaaga catgcggtgc accaccttgc cgcattagga aagactacaa    60
cagcactatc gatttattgt gccccacaga ctgttttagg aagcacccag atgctaccta   120
tcttaagtgt ggagcagggc cttggttaac tcccaggtgc tggta                   166

<210> SEQ ID NO 8
<211> LENGTH: 166
<212> TYPE: DNA
<213> ORGANISM: Hepatitis C Virus

<400> SEQUENCE: 8
tgggactggg ttcactaaga catgcggtgc accaccttgc cgcattagga gggactgcaa    60
cggaaccctc gacctattgt gccccacaga ctgtttcaga aagcacccag atactaccta   120
ccttaagtgt ggagcggggc cttggttgac ccccaaatgc atggta                  166

<210> SEQ ID NO 9
<211> LENGTH: 160
<212> TYPE: DNA
<213> ORGANISM: Hepatitis C Virus

<400> SEQUENCE: 9
ctcaactgga ttcaccaaag tgtgcggagc gccccctgt gtcatcggag gggcgggcaa    60
caacaccttg cgctgcccca ctgattgttt ccgcaagcat ccggaagcca cgtactctcg   120
gtgcggctcc ggtccctgga ttacgcccag gtgcctggtc                         160

<210> SEQ ID NO 10
<211> LENGTH: 160
<212> TYPE: DNA
<213> ORGANISM: Hepatitis C Virus

<400> SEQUENCE: 10
tggcacaggg ttcaccaaga cgtgtggggc cccccatgt aacatcgggg gggtcggcaa    60
taacaccttg acttgcccca cggactgttt ccggaagcac cccgaggcca cttacaccaa   120
atgtggttcg gggccttggc tgacacctag gtgcatagtt                         160

<210> SEQ ID NO 11
<211> LENGTH: 164
<212> TYPE: DNA
<213> ORGANISM: Hepatitis C Virus

<400> SEQUENCE: 11
ctccactgtt tcaccaaaac ttgcggcgca ccaccctgcc gcatcagagc tgactttaat    60
gccagcacgg acctgctgtg ccccacggac tgtttcagga agcatcctga agccacttac   120
atcaaatgtg gctctgggcc cctgtgacgc caaagtgcct gata                    164

<210> SEQ ID NO 12
<211> LENGTH: 167
<212> TYPE: DNA
<213> ORGANISM: Artificial Sequence
<220> FEATURE:
<223> OTHER INFORMATION: Description of Artificial Sequence:Synthetic

<400> SEQUENCE: 12
tgggactggg ttcactaaga catgcggtgc accaccttgc cgcattagga gggactgcaa    60
```
cggaaccctc gacctattgt gccccacaga ctgtttcaga aagcacccag atactaccta      120
ccttaagtgt ggagcggggg ccttggttga cccccaaatg catggta                    167

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Flag
      Epitope

<400> SEQUENCE: 13

Asp Tyr Lys Asp Asp Asp Asp Lys
 1               5

<210> SEQ ID NO 14
<211> LENGTH: 10
<212> TYPE: PRT
<213> ORGANISM: T7 Bacteriophage

<400> SEQUENCE: 14

Met Ala Ser Met Thr Gly Gly Gln Met Gly
 1               5                  10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence:S-Tag
      Sequence

<400> SEQUENCE: 15

Lys Glu Thr Ala Ala Ala Lys Phe Glu Arg Gln His Met Asp Ser
 1               5                  10                  15

<210> SEQ ID NO 16
<211> LENGTH: 20
<212> TYPE: DNA
<213> ORGANISM: Hepatitis C Virus

<400> SEQUENCE: 16
cgcgcacraa gtasggyact                                                   20

<210> SEQ ID NO 17
<211> LENGTH: 21
<212> TYPE: DNA
<213> ORGANISM: Hepatitis C Virus
<220> FEATURE:
<221> NAME/KEY: variation
<222> LOCATION: (9)
<223> OTHER INFORMATION: n is inosine (i)
<220> FEATURE:
<221> NAME/KEY: modified_base
<222> LOCATION: (9)
<223> OTHER INFORMATION: i

<400> SEQUENCE: 17
cgcatggcnt gggayatgat g                                                 21

<210> SEQ ID NO 18
<211> LENGTH: 32
<212> TYPE: DNA
<213> ORGANISM: Hepatitus C Virus

<400> SEQUENCE: 18

```
cgaagcttca tatgatcgct ggtgctcact gg                                  32
```

<210> SEQ ID NO 19
<211> LENGTH: 38
<212> TYPE: DNA
<213> ORGANISM: Hepatitis C Virus

<400> SEQUENCE: 19

```
gcggatccct gcagctacaa actggcttga agaatcca                            38
```

<210> SEQ ID NO 20
<211> LENGTH: 34
<212> TYPE: DNA
<213> ORGANISM: Hepatitis C Virus

<400> SEQUENCE: 20

```
cgcatatgga gctcgcgggg gcccactggg gagt                                34
```

<210> SEQ ID NO 21
<211> LENGTH: 38
<212> TYPE: DNA
<213> ORGANISM: Hepatitis C Virus

<400> SEQUENCE: 21

```
gctctagact gcagctatat gccagcctgg agcaccat                            38
```

<210> SEQ ID NO 22
<211> LENGTH: 34
<212> TYPE: DNA
<213> ORGANISM: Hepatitis C Virus

<400> SEQUENCE: 22

```
cgctcgagcc atggttggcg gggctcattg gggc                                34
```

<210> SEQ ID NO 23
<211> LENGTH: 40
<212> TYPE: DNA
<213> ORGANISM: Hepatits C Virus

<400> SEQUENCE: 23

```
tcgaattcgg atcctacaaa gcacctttta ggagataagc                          40
```

<210> SEQ ID NO 24
<211> LENGTH: 34
<212> TYPE: DNA
<213> ORGANISM: Hepatitis C Virus

<400> SEQUENCE: 24

```
cgctcgagcc atggttttcg gcggccattg ggtg                                34
```

<210> SEQ ID NO 25
<211> LENGTH: 40
<212> TYPE: DNA
<213> ORGANISM: Hepatitis C Virus

<400> SEQUENCE: 25

```
tcgaattcgg atcctacaga gacgctttaa ggaggtaggc                          40
```

<210> SEQ ID NO 26
<211> LENGTH: 23
<212> TYPE: DNA
<213> ORGANISM: Hepatitis C Virus
<220> FEATURE:
<221> NAME/KEY: modified_base
<222> LOCATION: (15)
<223> OTHER INFORMATION: i

<400> SEQUENCE: 26
tggttcggbt gywcntggat gaa                                              23

<210> SEQ ID NO 27
<211> LENGTH: 26
<212> TYPE: DNA
<213> ORGANISM: Hepatitis C Virus
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (18)
<223> OTHER INFORMATION: i

<400> SEQUENCE: 27
taatgccana rcckrtangg gtagtc                                           26

<210> SEQ ID NO 28
<211> LENGTH: 379
<212> TYPE: PRT
<213> ORGANISM: Artificial Sequence
<220> FEATURE:
<223> OTHER INFORMATION: Description of Artificial Sequence:Pdisplay
      Vector Sequence with E2 insert of Sflb-E2

<400> SEQUENCE: 28

Met Glu Thr Asp Th

```
                225                 230                 235                 240
Arg Lys His Pro Glu Ala Thr Tyr Thr Lys Cys Gly Ser Gly Pro Trp
                    245                 250                 255
Leu Thr Pro Arg Cys Ile Val Asp Tyr Pro Tyr Arg Leu Trp His Tyr
                260                 265                 270
Pro Cys Thr Val Asn Phe Thr Ile Phe Lys Val Arg Met Tyr Val Gly
            275                 280                 285
Gly Met Glu His Arg Leu Asn Ala Ala Cys Asn Trp Thr Arg Gly Glu
        290                 295                 300
Arg Cys Asp Leu Glu Asp Arg Asp Arg Ser Glu Leu Gln Val Ala Glu
305                 310                 315                 320
Gln Lys Leu Ile Ser Glu Glu Asp Leu Asn Ala Val Gly Gln Asp Thr
                325                 330                 335
Gln Glu Val Ile Val Val Pro His Ser Leu Pro Phe Lys Val Val Val
            340                 345                 350
Ile Ser Ala Ile Leu Ala Leu Val Val Leu Thr Ile Ile Ser Leu Ile
        355                 360                 365
Ile Leu Ile Met Leu Trp Gln Lys Lys Pro Arg
370                 375

<210> SEQ ID NO 29
<211> LENGTH: 278
<212> TYPE: PRT
<213> ORGANISM: Hepatitis C Virus

<400> SEQUENCE: 29

Thr Thr Tyr Thr Thr Gly Gly Ala Ala Ser Arg Thr Thr Gly Thr Phe
1               5                   10                  15
Thr Ser Leu Phe Asn Ala Gly Ser Ser Gln Lys Ile Gln Leu Ile Asn
                20                  25                  30
Thr Asn Gly Ser Trp His Ile Asn Arg Thr Ala Leu Asn Cys Asn Asp
            35                  40                  45
Ser Leu Asn Thr Gly Phe Leu Ala Ala Leu Phe Tyr Val His Arg Phe
        50                  55                  60
Asn Ala Ser Gly Cys Pro Ala Arg Met Ala Ser Cys Arg Ser Ile Asp
65                  70                  75                  80
Ala Phe Asp Gln Gly Trp Gly Pro Ile Thr Tyr Ala Glu Ser His Ser
                85                  90                  95
Ser Asp Gln Arg Pro Tyr Cys Trp His Tyr Ala Pro Lys Pro Cys Gly
            100                 105                 110
Ile Val Pro Ala Ser Gln Val Cys Gly Pro Val Tyr Cys Phe Thr Pro
        115                 120                 125
Ser Pro Val Val Val Gly Thr Thr Asp His His Gly Val Pro Thr Tyr
130                 135                 140
Ser Trp Gly Glu Asn Glu Thr Asp Val Leu Leu Leu Asn Asn Thr Arg
145                 150                 155                 160
Pro Pro Gln Gly Asn Trp Phe Gly Cys Thr Trp Met Asn Gly Thr Gly
                165                 170                 175
Phe Thr Lys Thr Cys Gly Gly Pro Pro Cys Asn Ile Gly Gly Val Gly
            180                 185                 190
Asn Asn Thr Leu Thr Cys Pro Thr Asp Cys Phe Arg Lys His Pro Glu
        195                 200                 205
Ala Thr Tyr Thr Lys Cys Gly Ser Gly Pro Trp Leu Thr Pro Arg Cys
210                 215                 220
```

-continued

```
Ile Val Asp Tyr Pro Tyr Arg Leu Trp His Tyr Pro Cys Thr Val Asn
225                 230                 235                 240

Phe Thr Ile Phe Lys Val Arg Met Tyr Val Gly Gly Met Glu His Arg
                245                 250                 255

Leu Asn Ala Ala Cys Asn Trp Thr Arg Gly Glu Arg Cys Asp Leu Glu
            260                 265                 270

Asp Arg Asp Arg Ser Glu
        275

<210> SEQ ID NO 30
<211> LENGTH: 251
<212> TYPE: PRT
<213> ORGANISM: Hepatitis C Virus

<400> SEQUENCE: 30

Ile Gln Leu Ile Asn Thr Asn Gly Ser Trp His Ile Asn Arg Thr Ala
 1               5                  10                  15

Leu Asn Cys Asn Asp Ser Leu Asn Thr Gly Phe Leu Ala Ala Leu Phe
                20                  25                  30

Tyr Val His Arg Phe Asn Ala Ser Gly Cys Pro Ala Arg Met Ala Ser
            35                  40                  45

Cys Arg Ser Ile Asp Ala Phe Asp Gln Gly Trp Gly Pro Ile Thr Tyr
50                  55                  60

Ala Glu Ser His Ser Ser Asp Gln Arg Pro Tyr Cys Trp His Tyr Ala
65                  70                  75                  80

Pro Lys Pro Cys Gly Ile Val Pro Ala Ser Gln Val Cys Gly Pro Val
                85                  90                  95

Tyr Cys Phe Thr Pro Ser Pro Val Val Val Gly Thr Thr Asp His His
            100                 105                 110

Gly Val Pro Thr Tyr Ser Trp Gly Glu Asn Glu Thr Asp Val Leu Leu
        115                 120                 125

Leu Asn Asn Thr Arg Pro Pro Gln Gly Asn Trp Phe Gly Cys Thr Trp
130                 135                 140

Met Asn Gly Thr Gly Phe Thr Lys Thr Cys Gly Gly Pro Pro Cys Asn
145                 150                 155                 160

Ile Gly Gly Val Gly Asn Asn Thr Leu Thr Cys Pro Thr Asp Cys Phe
                165                 170                 175

Arg Lys His Pro Glu Ala Thr Tyr Thr Lys Cys Gly Ser Gly Pro Trp
            180                 185                 190

Leu Thr Pro Arg Cys Ile Val Asp Tyr Pro Tyr Arg Leu Trp His Tyr
        195                 200                 205

Pro Cys Thr Val Asn Phe Thr Ile Phe Lys Val Arg Met Tyr Val Gly
210                 215                 220

Gly Met Glu His Arg Leu Asn Ala Ala Cys Asn Trp Thr Arg Gly Glu
225                 230                 235                 240

Arg Cys Asp Leu Glu Asp Arg Asp Arg Ser Glu
                245                 250

<210> SEQ ID NO 31
<211> LENGTH: 215
<212> TYPE: PRT
<213> ORGANISM: Hepatitis C Virus

<400> SEQUENCE: 31

Phe Asn Ala Ser Gly Cys Pro Ala Arg Met Ala Ser Cys Arg Ser Ile
 1               5                  10                  15
```

```
Asp Ala Phe Asp Gln Gly Trp Gly Pro Ile Thr Tyr Ala Glu Ser His
            20                  25                  30

Ser Ser Asp Gln Arg Pro Tyr Cys Trp His Tyr Ala Pro Lys Pro Cys
        35                  40                  45

Gly Ile Val Pro Ala Ser Gln Val Cys Gly Pro Val Tyr Cys Phe Thr
    50                  55                  60

Pro Ser Pro Val Val Gly Thr Thr Asp His His Gly Val Pro Thr
65                  70                  75                  80

Tyr Ser Trp Gly Glu Asn Glu Thr Asp Val Leu Leu Leu Asn Asn Thr
                85                  90                  95

Arg Pro Pro Gln Gly Asn Trp Phe Gly Cys Thr Trp Met Asn Gly Thr
            100                 105                 110

Gly Phe Thr Lys Thr Cys Gly Gly Pro Pro Cys Asn Ile Gly Gly Val
        115                 120                 125

Gly Asn Asn Thr Leu Thr Cys Pro Thr Asp Cys Phe Arg Lys His Pro
130                 135                 140

Glu Ala Thr Tyr Thr Lys Cys Gly Ser Gly Pro Trp Leu Thr Pro Arg
145                 150                 155                 160

Cys Ile Val Asp Tyr Pro Tyr Arg Leu Trp His Tyr Pro Cys Thr Val
                165                 170                 175

Asn Phe Thr Ile Phe Lys Val Arg Met Tyr Val Gly Gly Met Glu His
            180                 185                 190

Arg Leu Asn Ala Ala Cys Asn Trp Thr Arg Gly Glu Arg Cys Asp Leu
        195                 200                 205

Glu Asp Arg Asp Arg Ser Glu
    210                 215

<210> SEQ ID NO 32
<211> LENGTH: 192
<212> TYPE: PRT
<213> ORGANISM: Hepatitis C Virus

<400> SEQUENCE: 32

Gly Pro Ile Thr Tyr Ala Glu Ser His Ser Ser Asp Gln Arg Pro Tyr
1               5                   10                  15

Cys Trp His Tyr Ala Pro Lys Pro Cys Gly Ile Val Pro Ala Ser Gln
            20                  25                  30

Val Cys Gly Pro Val Tyr Cys Phe Thr Pro Ser Pro Val Val Val Gly
        35                  40                  45

Thr Thr Asp His His Gly Val Pro Thr Tyr Ser Trp Gly Glu Asn Glu
    50                  55                  60

Thr Asp Val Leu Leu Leu Asn Asn Thr Arg Pro Pro Gln Gly Asn Trp
65                  70                  75                  80

Phe Gly Cys Thr Trp Met Asn Gly Thr Gly Phe Thr Lys Thr Cys Gly
                85                  90                  95

Gly Pro Pro Cys Asn Ile Gly Gly Val Gly Asn Asn Thr Leu Thr Cys
            100                 105                 110

Pro Thr Asp Cys Phe Arg Lys His Pro Glu Ala Thr Tyr Thr Lys Cys
        115                 120                 125

Gly Ser Gly Pro Trp Leu Thr Pro Arg Cys Ile Val Asp Tyr Pro Tyr
130                 135                 140

Arg Leu Trp His Tyr Pro Cys Thr Val Asn Phe Thr Ile Phe Lys Val
145                 150                 155                 160

Arg Met Tyr Val Gly Gly Met Glu His Arg Leu Asn Ala Ala Cys Asn
                165                 170                 175
```

Trp Thr Arg Gly Glu Arg Cys Asp Leu Glu Asp Arg Asp Arg Ser Glu
            180                 185                 190

<210> SEQ ID NO 33
<211> LENGTH: 261
<212> TYPE: PRT
<213> ORGANISM: Hepatitis C Virus

<400> SEQUENCE: 33

Thr Thr Tyr Thr Thr Gly Gly Ala Ala Ser Arg Thr Thr Gly Thr Phe
 1               5                  10                  15

Thr Ser Leu Phe Asn Ala Gly Ser Ser Gln Lys Ile Gln Leu Ile Asn
            20                  25                  30

Thr Asn Gly Ser Trp His Ile Asn Arg Thr Ala Leu Asn Cys Asn Asp
        35                  40                  45

Ser Leu Asn Thr Gly Phe Leu Ala Ala Leu Phe Tyr Val His Arg Phe
    50                  55                  60

Asn Ala Ser Gly Cys Pro Ala Arg Met Ala Ser Cys Arg Ser Ile Asp
65                  70                  75                  80

Ala Phe Asp Gln Gly Trp Gly Pro Ile Thr Tyr Ala Glu Ser His Ser
                85                  90                  95

Ser Asp Gln Arg Pro Tyr Cys Trp His Tyr Ala Pro Lys Pro Cys Gly
            100                 105                 110

Ile Val Pro Ala Ser Gln Val Cys Gly Pro Val Tyr Cys Phe Thr Pro
        115                 120                 125

Ser Pro Val Val Gly Thr Thr Asp His His Gly Val Pro Thr Tyr
    130                 135                 140

Ser Trp Gly Glu Asn Glu Thr Asp Val Leu Leu Leu Asn Asn Thr Arg
145                 150                 155                 160

Pro Pro Gln Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Val Gly
            180                 185                 190

Asn Asn Thr Leu Thr Cys Pro Thr Asp Cys Phe Arg Lys His Pro Glu
        195                 200                 205

Ala Thr Tyr Thr Lys Cys Gly Ser Gly Pro Trp Leu Thr Pro Arg Cys
    210                 215                 220

Ile Val Asp Tyr Pro Tyr Arg Leu Trp His Tyr Pro Cys Thr Val Asn
225                 230                 235                 240

Phe Thr Ile Phe Lys Val Arg Met Tyr Val Gly Gly Met Glu His Arg
                245                 250                 255

Leu Asn Ala Ala Cys
            260

<210> SEQ ID NO 34
<211> LENGTH: 196
<212> TYPE: PRT
<213> ORGANISM: Hepatitis C Virus

<400> SEQUENCE: 34

Thr Thr Tyr Thr Thr Gly Gly Ala Ala Ser Arg Thr Thr Gly Thr Phe
 1               5                  10                  15

Thr Ser Leu Phe Asn Ala Gly Ser Ser Gln Lys Ile Gln Leu Ile Asn
            20                  25                  30

Thr Asn Gly Ser Trp His Ile Asn Arg Thr Ala Leu Asn Cys Asn Asp
        35                  40                  45

```
Ser Leu Asn Thr Gly Phe Leu Ala Ala Leu Phe Tyr Val His Arg Phe
     50                  55                  60

Asn Ala Ser Gly Cys Pro Ala Arg Met Ala Ser Cys Arg Ser Ile Asp
 65                  70                  75                  80

Ala Phe Asp Gln Gly Trp Gly Pro Ile Thr Tyr Ala Glu Ser His Ser
                     85                  90                  95

Ser Asp Gln Arg Pro Tyr Cys Trp His Tyr Ala Pro Lys Pro Cys Gly
            100                 105                 110

Ile Val Pro Ala Ser Gln Val Cys Gly Pro Val Tyr Cys Phe Thr Pro
            115                 120                 125

Ser Pro Val Val Gly Thr Thr Asp His His Gly Val Pro Thr Tyr
    130                 135                 140

Ser Trp Gly Glu Asn Glu Thr Asp Val Leu Leu Asn Asn Thr Arg
145                 150                 155                 160

Pro Pro Gln Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Val Gly
                180                 185                 190

Asn Asn Thr Leu
        195

<210> SEQ ID NO 35
<211> LENGTH: 192
<212> TYPE: PRT
<213> ORGANISM: Hepatitis C Virus

<400> SEQUENCE: 35

Tyr Glu Val Arg Asn Val Ser Gly Val Thr His Val Thr Asn Asp Cys
  1               5                  10                  15

Ser Asn Ser Ser Ile Val Tyr Glu Ala Ala Asp Met Ile Met His Thr
             20                  25                  30

Pro Gly Cys Val Pro Cys Val Arg Glu Gly Asn Thr Ser Arg Cys Trp
         35                  40                  45

Val Ala Leu Thr Pro Thr Leu Ala Ala Arg Asn Ala Ser Val Pro Thr
 50                  55                  60

Ala Ala Ile Arg Arg His Ile Asp Leu Leu Val Gly Thr Ala Thr Phe
 65                  70                  75                  80

Cys Ser Ala Met Tyr Val Gly Asp Leu Cys Gly Ser Val Phe Leu Val
                 85                  90                  95

Ser Gln Leu Phe Thr Phe Ser Pro Arg Arg His His Thr Val Gln Asp
            100                 105                 110

Cys Asn Cys Ser Ile Tyr Pro Gly His Val Thr Gly His Arg Met Ala
            115                 120                 125

Trp Asp Met Met Met Asn Trp Ser Pro Thr Ala Ala Leu Val Val Ser
130                 135                 140

Gln Leu Leu Arg Ile Pro Gln Ala Val Met Asp Met Val Ala Gly Ala
145                 150                 155                 160

His Trp Gly Val Leu Ala Gly Leu Ala Tyr Tyr Ser Met Ala Gly Asn
                165                 170                 175

Trp Ala Lys Val Leu Ile Val Met Leu Leu Phe Ala Gly Val Asp Gly
                180                 185                 190
```

PREVENTION AND TREATMENT OF HCV INFECTION EMPLOYING ANTIBODIES DIRECTED AGAINST CONFORMATIONAL EPITOPES

CROSS REFERENCE TO RELATED APPLICATIONS

This application is a continuation-in-part of patent application U.S. Ser. No. 09/430,489, filed Oct. 29, 1999, now U.S. Pat. No. 6,692,908, which is a continuation-in-part of patent application U.S. Ser. No. 09/187,057, filed Nov. 5, 1998 abandoned. Each if these applications is incorporated herein by reference.

GOVERNMENT LICENSE RIGHTS

The U.S. government has a paid-up license in this invention and the right in limited circumstances to require the patent owner to license others on reasonable terms as provided for by the terms of grant no. DA60596 and HL33811 awarded by the National Institutes of Health (NIH).

INTRODUCTION

1. Technical Field

The field of this invention is related to the preparation of human monoclonal antibodies (HMAb) to structurally conserved epitopes of HCV. Such antibodies can be found in a high proportion of patients and are useful, for example, in the diagnosis and therapy of HCV infection, including being useful in the identification of patients expected to benefit from certain therapeutic strategies.

2. Background

Hepatitis C virus (HCV) is an enveloped virus the genetic information for which is encoded in a 9.5 kb positive strand RNA genome. A highly conserved noncoding region of 341 bp is localized at the 5'-end of this viral genome, which is followed by a long open-reading frame coding for a polyprotein of approximately 3,010 amino acids. Two putative envelope glycoproteins E1 (gp35) and E2 (gp72) have been identified with 5 or 6 and 11 N-linked glycosylation sites, respectively. A high level of genetic variability is associated with the envelope genes. This variability is highly accentuated at the 5'-end of the E2 gene, where two hypervariable regions termed HVR1 and HVR2, have been described. Antibodies to HVR1 appear to mediate virus neutralization in cell culture and chimpanzee protection studies (Farci et al., 1996 *Proc. Natl. Acad. Sci. USA* 93:15394–15399; Shimizu et al., 1994 *J. Virol.* 68:1494–1500; each of which is incorporated herein by reference). Unfortunately, antibodies to HVR1 tend to be isolate specific and over time drive the replication of new viral variants that the existing immune response does not recognize (Farci et al., 1994 *Proc. Natl. Acad. Sci. USA* 91:7792–7796; Weiner et al., 1992 *Proc. Natl. Acad. Sci. USA* 89:3468–3472; Kato et al., 1993 *J. Virol.* 67:3923–3930; each of which is incorporated herein by reference), although progress has been made at inducing a broader immune response to HVR1 related sequences (Puntoriero et al., 1998 *EMBO Journal* 17:3521–3533; incorporated herein by reference). HCV envelope antigens appear to be highly immunogenic when expressed in glycosylated forms (da Silva Cardoso et al., 1997 *Ann. Hematol.* 74:135–7; incorporated herein by reference). Preliminary data suggest the existence of conserved epitopes within the E2 protein (Lesniewski et al., 1995 *J. Med. Virol.* 45:415–22; incorporated herein by reference). The existence of neutralizing antibodies in serum from infected patients has been proposed.

Studies using HCV E1–E2 proteins expressed in mammalian cells have shown that infected individuals have an antibody response to HCV E2 composed in part to epitopes that are conformational in nature (Harada et al., 1994 *J. Gen. Virol.* 76:1223–1231; incorporated herein by reference). Studies involving the isolation of human monoclonal or recombinant antibodies to HCV E2 protein showed that a substantial fraction of these antibodies recognize conformational epitopes (da Silva Cordoso et al., 1998 *J. Med. Virol.* 55:28–34; Burioni et al., 1998 *Hepatology* 28:810–814; Habersetzer et al., 1998 *Virology* 249:32–41; each of which is incorporated herein by reference). As to biological function of these domains, investigators have employed surrogate assays to provide insights into virus neutralization since the virus cannot be grown, in vitro (Houghton, Hepatitis C viruses. In Fields, Knipe, Howley (eds) *Virology*. Lippincott-Raven, Philadelphia, pp. 1035–1058; incorporated herein by reference). One surrogate assay, the neutralization of binding (NOB) assay, evaluates the ability of a given antibody or serum to prevent the association of HCV E2 protein with a human T-cell line (Rosa et al., 1996 *Proc. Natl. Acad. Sci. USA* 93:1759–1763; incorporated herein by reference). The finding that serum antibodies obtained from chimpanzees protected by vaccination were strongly positive in the NOB assay provides support for the relevance of the assay as a measure of virus neutralization activity (Rosa et al., supra; Ishii et al., 1998 *Hepatology* 28:1117–1120; each of which is incorporated herein by reference).

The human tetraspannin cell surface protein CD81 (TAPA-1, for review see Levy et al., 1998 *Ann. Rev. Immunol.* 16:89–109; incorporated herein by reference) is the target protein bound by HCV E2 in the NOB assay (Pileri et al., 1998 *Science.* 282:938–941; incorporated herein by reference). Furthermore, human CD81 binds to free virions, and subsequently is a possible receptor for HCV (Pileri et al., supra). Using HCV 1a E2 proteins, several human monoclonal antibodies to HCV E2 protein have been reported to inhibit the interaction of HCV E2 with human cells (Burioni et al., 1998 *Hepatology* 28:810–814; Habersetzer et al., 1998 *Virology* 249:32–41; each of which is incorporated herein by reference). However, little is known about the conservation of the epitopes recognized by the NOB positive antibodies in HCV E2 proteins of different genotypes.

Other approaches to detection of and protection against HCV include the development of peptide mimetics. As an example, peptide mimetics of Hepatitis type A and C viral proteins have been created through production of randomly generated synthetic and phage-display peptide libraries for use in detection assays and vaccination therapies (Mattioli et al., 1995 *J. Virology* 69:5294–5299; Prezzi et al., 1996 *J. Immunol.* 156:4504–4513; each of which is incorporated herein by reference). However, effective antibody binding of these mimotopes has only been compared to linearly defined viral epitopes. The sequential recombinant fusing of several linearly defined immunodominant HCV epitopes has been described for use in diagnostic assays (Chein et al., 1999 *J. Clin. Microbiol.* 37:1393–1397; incorporated herein by reference). However, this multiple-epitope fusion antigen designed from linear epitopes was not created to function in the same capacity as a conformational mimetic: it was not designed to interfere with binding to a target receptor.

It is therefore of substantial interest to identify neutralizing antibodies in serum from infected patients which may be used in diagnosis and passive immunotherapy, where the antibodies would originate from a human cell, and provide for neutralization of a broad spectrum of genotypes, particularly in a particular geographical area. Both breadth of reactivity to multiple HCV genotypes and the ability to interfere with the binding of HCV virions to susceptible cells would be key attributes for a therapeutically useful neutralizing antibody. Also of interest is the design of peptide and non-peptide (organic) structural mimetics of HCV envelope proteins.

Relevant Literature

References providing background information concerning HCV include Abrignani 1997 Springer *Semin. Immunopathology* 19:47–55; Simmonds, 1995 *Hepatology* 21:570: 583; and Mahaney et al., 1994 *Hepatology* 20:1405–1411; each of which is incorporated herein by reference.

Da Silva Cardosa et al., 1998 *J. Med. Virology* 55:28–34 describe human monoclonal antibodies to HCV E1/E2. Habersetzer et al., 1998 *Virology* 249:32–41 describe human monoclonal antibodies capable of recognizing HCV E2 genotypes 1a and 1b. Burioni et al., 1998 report human recombinant Fabs for the HCV E2 protein. Deleersnyder et al., 1997 *J. of Virology* 71:697–704 describe an E2 reactive monoclonal antibody. Other references related to the use of antibodies to HCV include Burioni et al., 1998 *Hepatology* 28:810–814; Akatsuka, et al., 1993 *Hepatology* 18:503–510; DeLalla, et al., 1993 *J. Hepatol.* 18:163–167; Mondelli, et al., 1994 *J. Virol.* 68:4829–4836; Siemoneit, et al., 1994 *Hybridoma* 13:9–13; and Moradpour, et al., 1996 *J. Med. Virol.* 48:234–241; for producing human antibodies, Foung, et al., 1990 *J. Immunol. Methods* 70:83–90; Zimmerman, et al., 1990 *J. Immunol. Methods* 134:43–50; for producing modified antibodies using combinatorial libraries, Burton and Barbas, Dixon, F J (Ed.) *Advances in Immunology*, Vol. 57, Vi+391 p. Academic Press, Inc., San Diego, Calif., 191–280, 1994; Plaisant, et al., 1997 *Res. Virol.* 148–169; and Barbas and Burton, *Monoclonal Antibodies from Combinatorial Libraries. Cold Spring Harbor Laboratory Course Manual*, Cold Spring Harbor, N.Y., 1994. Each of the references cited in this paragraph is incorporated herein by reference.

An assay for antibodies binding to HCV E2 is described by Rosa et al., 1996 *Proc. Natl. Acad. Sci. USA* 93:1759–1763; incorporated herein by reference.

Vaccinia virus or baculovirus constructs having a portion of the HCV genome are described by Ralston et al., 1993 *J. Virology* 67:6733–6761 and Lanford et al., 1993 *Virology* 197:225–235; each of which is incorporated herein by reference.

SUMMARY OF THE INVENTION

One aspect of the present invention provides monoclonal antibodies, including human monoclonal antibodies, which bind to the dominant HCV types in major geographical areas. The dissociation constants for the antibodies to their epitopes are, for example, less than $10^{-7}$M, less than $10^{-8}$M, to less than $10^{-9}$M, and less than $10^{-10}$M. Specifically, a family of monoclonal antibodies binding to conformationally conserved epitopes of the HCV E2 protein is provided. Among the family are antibodies that bind to the dominant genotypes found in the United States, so as to be substantially pan-monoclonal antibodies in being able to bind to almost all cases of HCV infection, which have been diagnosed in the United States, as well as at least a substantial proportion of the cases in other geographic locales. The monoclonal antibodies find use in a variety of diagnostic assays. In addition, conformationally conserved expression of recombinant type 1 and type 2 HCV E2 proteins and fragments thereof are provided for use in assays, screening drugs, vaccines, diagnostic assays, and for other purposes. The inventive antibodies find use in passive immunotherapy strategies for reducing viral load of infected individuals and interfering with the infection of target cells. Antibodies recognizing conformationally dependent epitopes can also be used to provide a template for the rational design of peptide and conformationally-defined epitope mimetics (e.g., organic compounds, organometallic compounds, inorganic compounds, small molecules).

In a particularly preferred embodiment, the inventive antibodies are directed to conformational epitopes of the E2 or E1 protein of HCV. Conformational epitopes of E2 have been identified using a panel of monoclonal antibodies and a series of deletion constructs of E2. One group of antibodies has been found to bind to conformational epitopes between E2 amino acids 411–644 from HCV 1b. Antibodies of this group have been found to inhibit the interaction of E2 with CD81. Another group of antibodies has been found to bind to conformational epitopes between HCV 1b E2 amino acids 470–644. A third group of antibodies binds to conformational epitopes between HCV 1b E2 amino acids 470–644 but fails to inhibit the binding of E2 to CD81. A fourth group binds to conformational epitopes between HCV 1b E2 amino acids 644–661. In a particularly preferred embodiment, the conformational epitopes to which the antibodies are directed are conserved among HCV strains. The antibodies of the present invention may be combined with pharmaceutically acceptable excipients to provide pharmaceutical formulations.

Another aspect of the invention provides definition of conformational epitopes in HCV proteins, and further provided compositions and compounds containing such epitopes. For example, the present invention provides proteins, peptides, and small molecules comprising the conformational epitopes of HCV E2 protein. The peptides may be deletion constructs such as those in FIG. 23. The peptides may contain one or more conformational epitopes recognized by the antibodies of the present invention. In certain preferred embodiments, the proteins are strings of concatenated peptides at least one of which contains a conformational epitope of HCV. The peptides of the string may contain different conformational or linear epitopes of HCV or the peptides may contain the same epitope. The peptides of the string should preferably fold properly in order to display the conformational epitope substantially as it appears in nature. Such proteins and peptides may be used in formulating vaccines or used in diagnostic tests.

The present invention also provides a method for stratifying patients based on their immunological response to HCV and of identifying those patients likely to respond well to HCV immunotherapy. For example, a patient's serum may be used to test for the presence of antibodies directed against a particular epitope of HCV. If the patient does not have adequate levels of antibodies directed to such an epitope, human monoclonal antibodies directed against the epitope may be administered to the patient.

DEFINITIONS

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Antibody": The term antibody refers to an immunoglobulin, whether natural or wholly or partially synthetically produced. All derivatives and fragments thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

"Peptide": According to the present invention, a "peptide" comprises a string of at least three amino acids linked together by peptide bonds. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon—carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

FIG. 2 (SEQ ID NOS: 9–12) describes sequences amplified from the central region of the HCV E2 vaccinia virus clones. Shown are the sequences of the central fragment for HCV E2 vaccinia constructs Q1a, Q 1b, Q2a, and Q2b as compared to representative sequences of the appropriate HCV genotypes. Accession numbers for the representative sequences of each genotype are as follows HCV 1A=M62321, HCV 1B=D10750, HCV2A=D00944, HCV 2B=D10988. Phylogenetic analysis was performed with CLUSTALV and DNAPARS program of the PHYLIP package.

FIG. 3 (SEQ ID NOS: 1–8) is a comparison of sequences of HCV: 1a, Q1a-FR, -1b, 1Q1b-FR, 2a, Q2a-FR, -2b, -Q2b-FR, using the most parsimonious tree found.

FIG. 4 shows a graph of the reactivity of HCV sera with HCV E2 proteins of different genotypes. HCV E2 protein expressed by $6\times10^5$ HeLa cells infected with vaccinia virus Q1a ■, Q1b ▲, Q2a ▼, Q2b ♦, or non recombinant vaccinia virus VWA ○ was captured onto wells coated with 500 ng of GNA lectin. Wells were washed and blocked, and bound protein was incubated with increasing dilutions (x axis) of genotyped HCV sera or an HCV negative serum (indicated above the graph). Values are the mean absorbance of replicate wells. Error bars indicate one standard deviation from the mean.

FIG. 5 is a bar graph indicating the reactivity of sera from individuals infected with HCV genotype 2b with HCV E2 proteins of multiple genotypes. Twelve sera from individuals infected with HCV genotype 2b (x axis) were titrated against HCV E2 proteins of genotypes 1a (dark blue bars), 1b (magenta bars), 2a (yellow bars), and 2b (light blue bars). The dilution of the serum that resulted in a mean specific absorbance (mean absorbance obtained with HCV E2 containing extract subtracted from the mean specific absorbence obtained with the VWA extract) of 0.5 is indicated on the y axis. This value was calculated from titration curve data analogous to that presented in FIG. 4.

FIG. 6 depicts a schematic of a direct binding assay to assess for antibodies that recognize conformational epitopes of HCV E2 envelope proteins employed in the experiments described in FIGS. 7, 8, and 9. GNA lectin is coated onto a solid surface and then added E2-containing protein extracts are captured by the lectin. Test antibodies are allowed to bind to the captured E2, the excess unbound is removed, and bound antibody is detected with a labeled secondary antibody.

FIG. 7 is a bar graph of the reactivity of HCV HMAbs to HCV E2 captured by lectins. Proteins from cytoplasmic extracts of $6\times10^5$ cells infected with wild type (Bars labeled VWA) or HCV 1a E2 (HCV 1a) (bars labeled HCV) expressing vaccinia virus were applied to microtiter plates coated with 500 ng of *Galanthus nivalis* (GNA) or *Tiriticum*

*vulgaris* (WGA). Captured proteins were incubated with 5 µg/ml of the indicated HMAbs (x axis). R04 is an isotype-matched control. Bound HMAb was detected with anti-human antibody-alkaline phosphatase and appropriate substrate. Bars indicate the mean OD value of replicate wells. Error bars indicate one standard deviation from the mean.

Figure 8A:
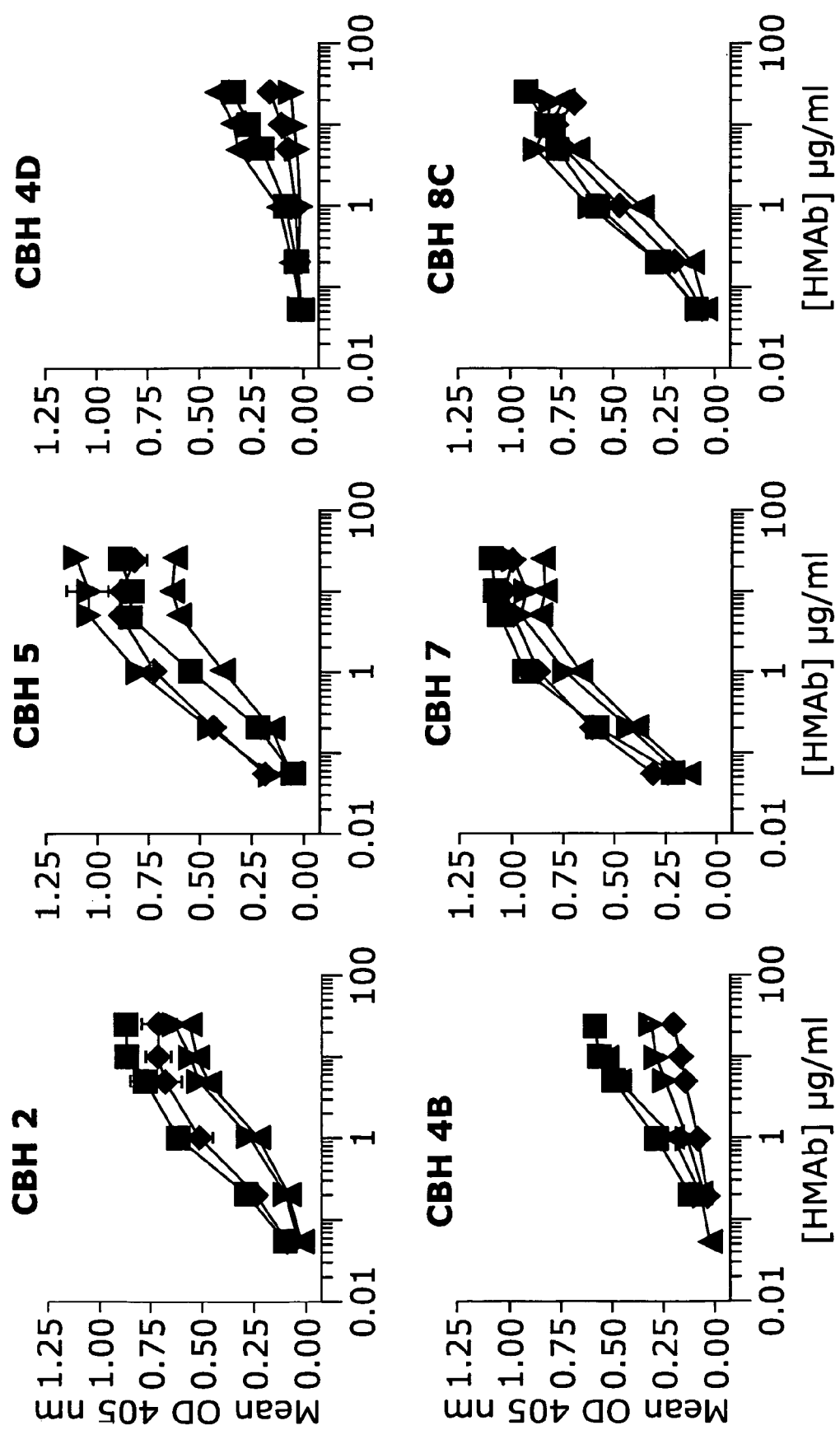
Figure 8B:
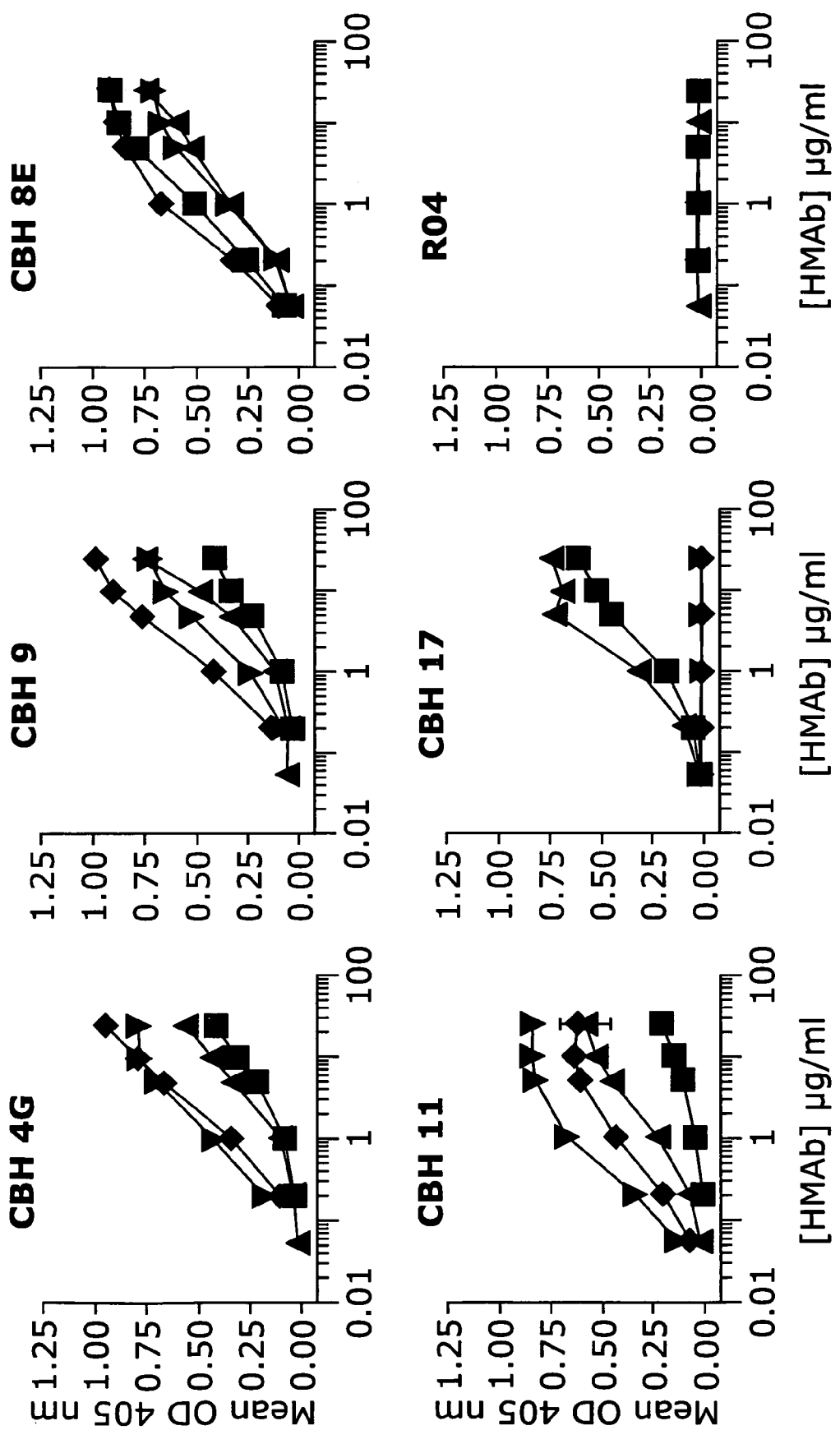

FIG. 8 shows graphs of HCV antibody reactivity with E2 protein of divergent HCV genotypes. HCV E2 proteins expressed by 6×10⁵ HeLa cells infected with vaccinia virus Q1a ■, Q1b ▲, Q2a ▼, Q2b ♦ was captured onto wells coated with 500 ng of GNA lectin. Wells were washed and blocked, and bound protein was incubated with the indicated HCV HMAbs (HMAb identified above each of FIGS. 9A–9J) and control HMAb (R04) FIG. 9K to a CMV protein (Ward, et al., 1995, *Proc Natl Acad Sci USA*. 92:6773–6777; incorporated herein by reference). Values are the mean specific binding (extracts of cells infected with vaccinia virus expressing HCV E2 protein—wt vaccinia extracts) of replicate wells. Reactivity of HCV and control HMAbs with proteins from wt vaccinia virus infected cells did not exceed an absorbance of 0.04. Error bars indicate one standard deviation from the mean.

Figure 9:
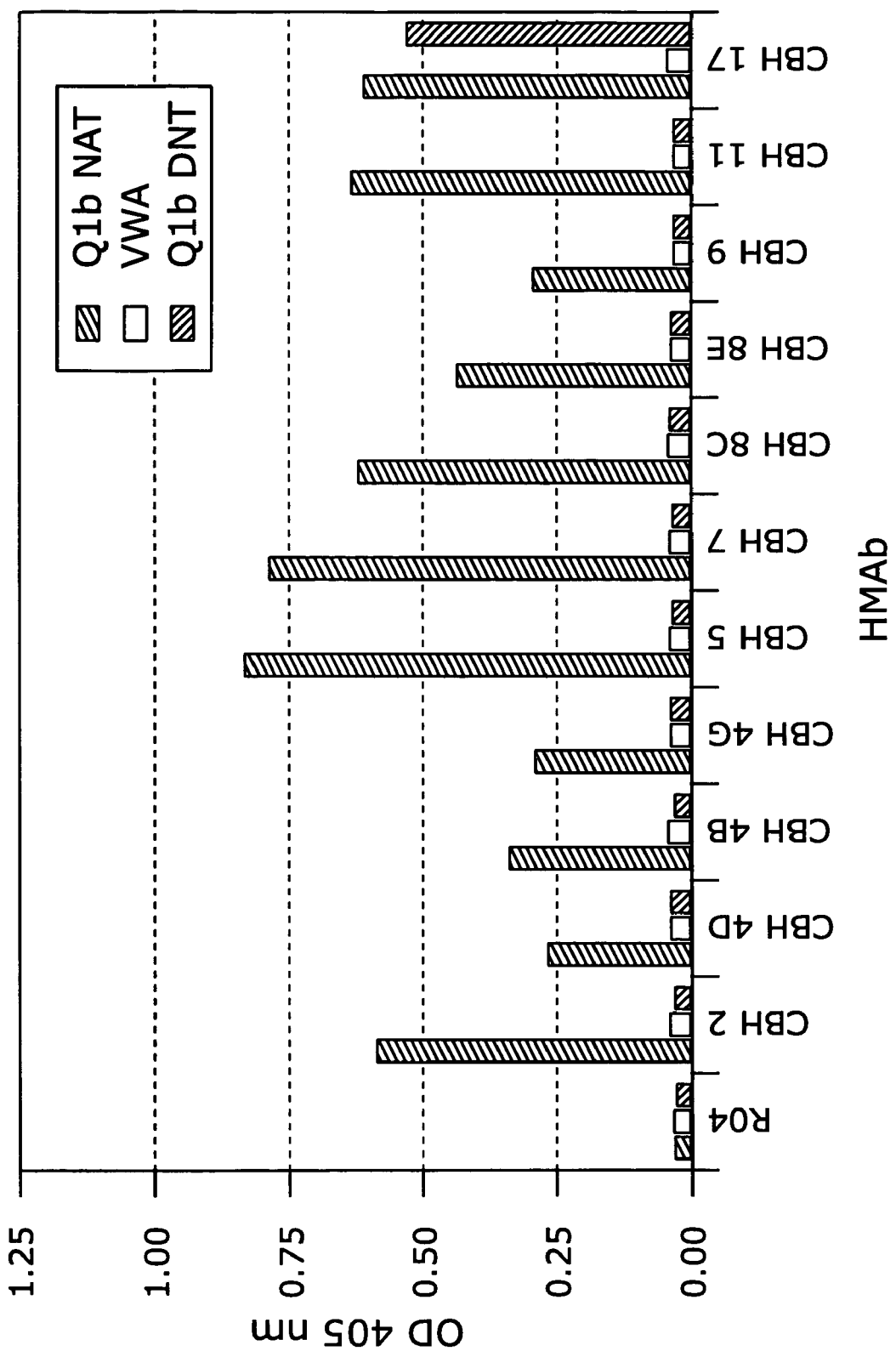

FIG. 9 is a bar graph showing the reactivity of HCV HMAbs with native (NAT) and denatured (DNT) HCV 1b E2 protein. Cytoplasmic extract derived from 6×10⁵ HeLa cells infected with vaccinia virus Q1b and VWA or VWA alone were either left untreated (blue bars) or denatured by incubation with 0.5% SDS and 5 mM dithiothreitol for 15 minutes at 56° C. (yellow bars). After treatment, proteins were diluted 1:5 in BLOTTO and captured onto wells coated with 500 ng of GNA lectin. Wells were washed and blocked, and bound protein was incubated with the indicated concentration of HCV HMAbs and control HMAb (R04). Bound antibody was detected with anti-human IgG alkaline phosphatase conjugate and PNPP. Color development was allowed to proceed for 45 minutes. Values for native and denatured HCV 1b are the mean signal obtained from replicate wells. Signals from single wells of native and denatured proteins derived from VWA infected HeLa cells were indistinguishable and also averaged (red bars). Error bars indicate one standard deviation from the mean.

Figure 10:
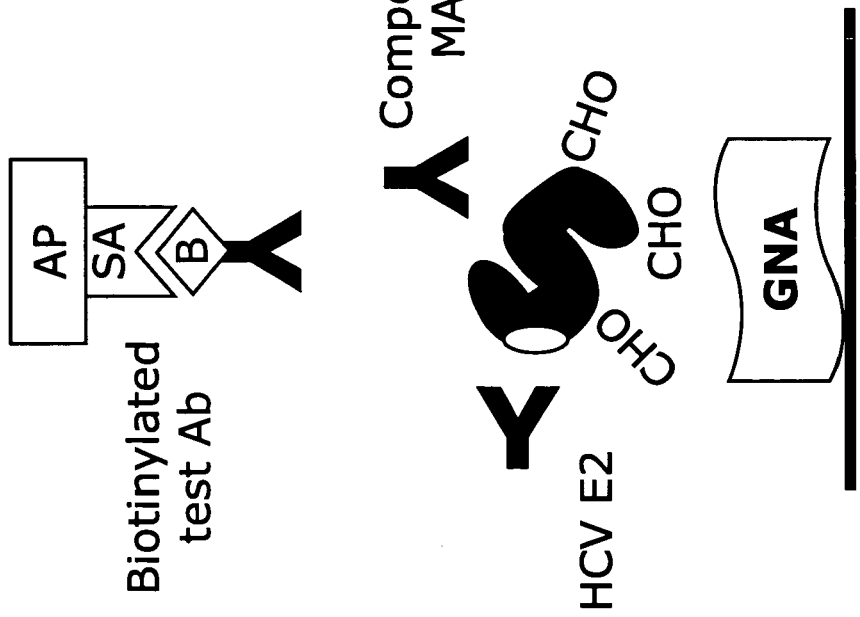
Figure 11:
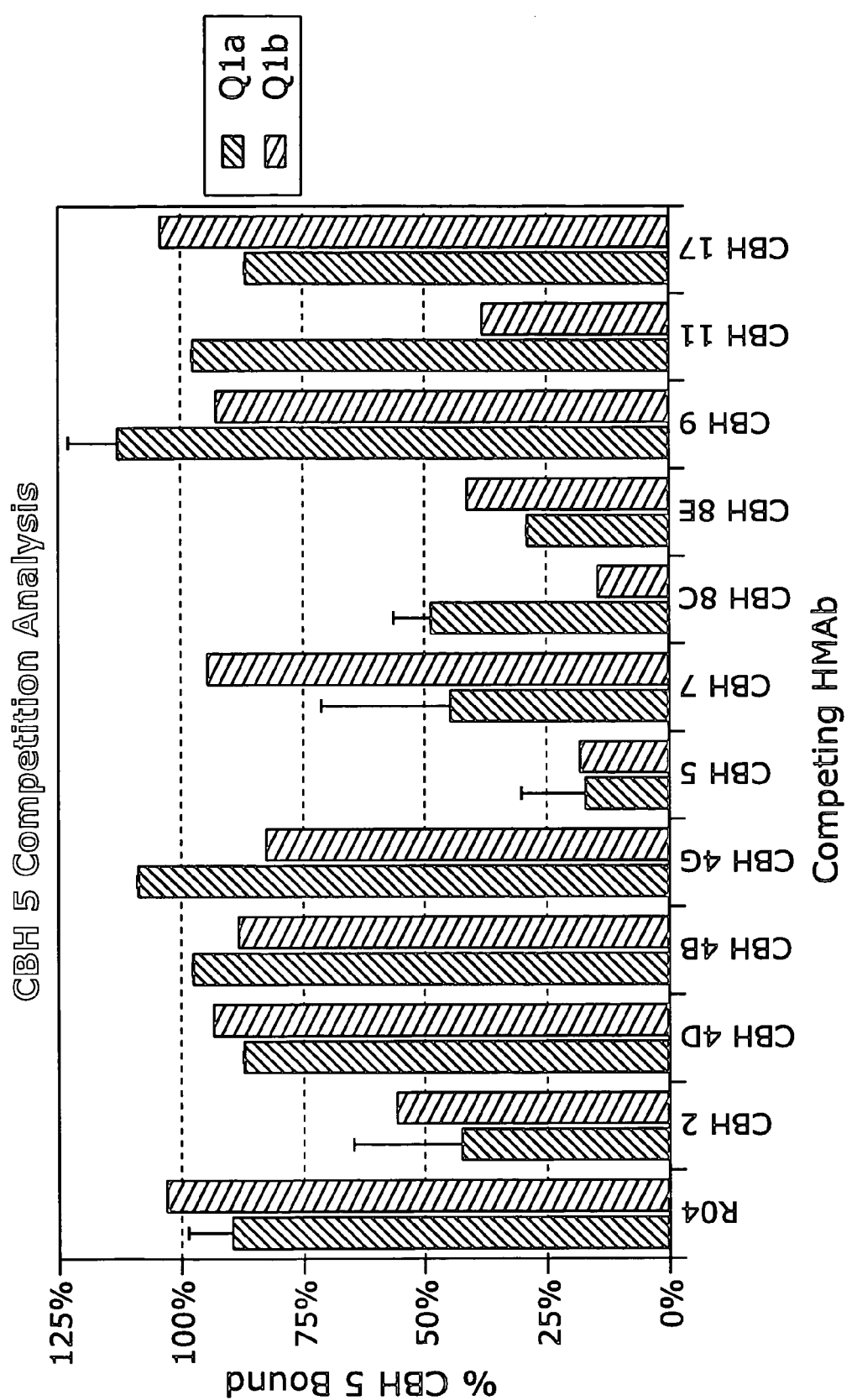
Figure 12:
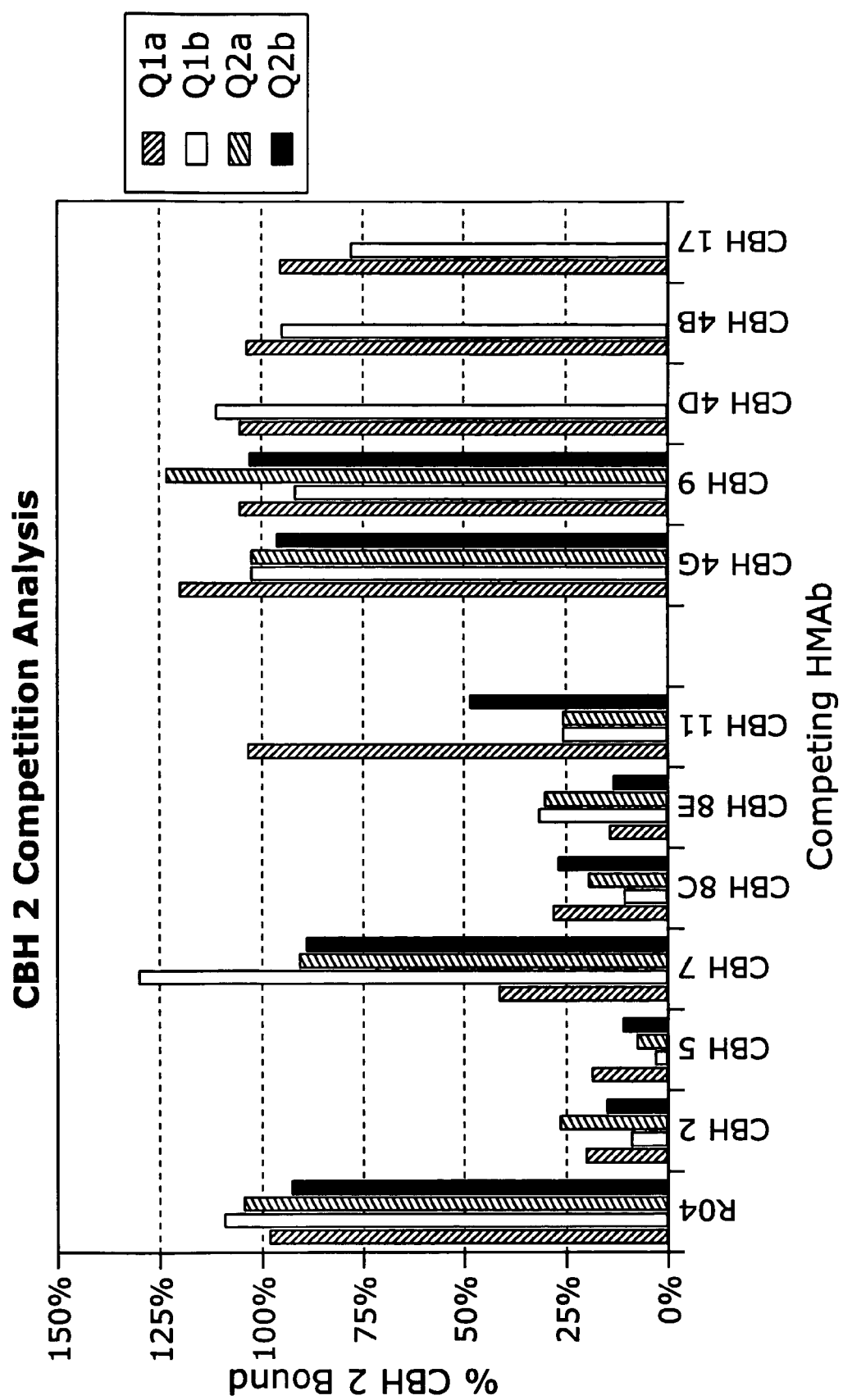
Figure 13:
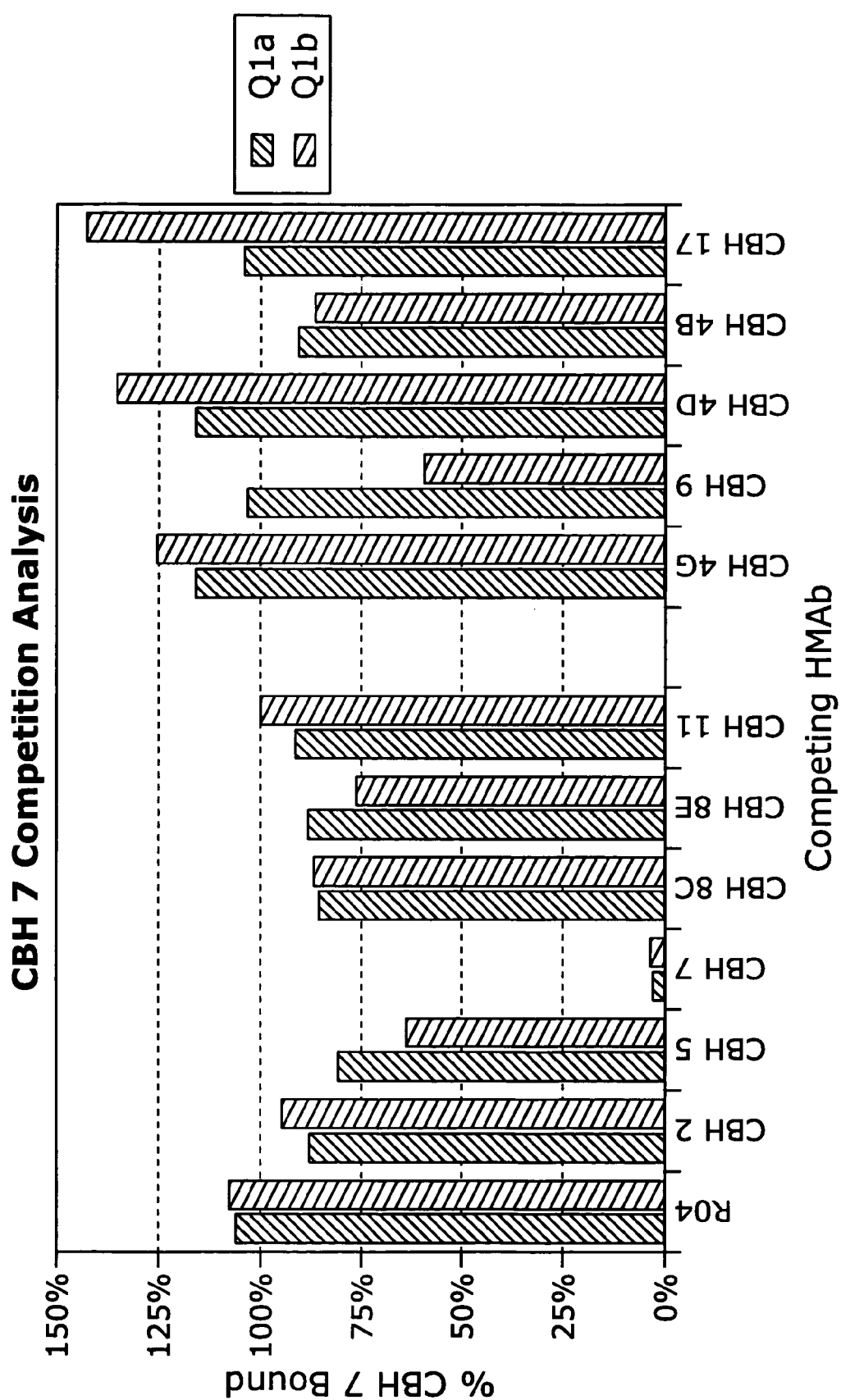

FIG. 10 depicts a schematic of the competition binding analysis employed in the experiments described in FIGS. 11, 12, and 13. GNA lectin is coated onto a solid surface and then added E2-containing protein extracts are captured by the lectin. Competing antibodies are allowed to bind to the captured E2 before removing unbound excess and adding labeled test antibody.

FIG. 11 is a bar graph of a competition analysis using HCV HMAb CBH-5. HCV E2 protein from cytoplasmic extracts of HeLa cells infected with vaccinia virus Q1a (blue bars) or Q1b (red bars) was captured with 500 ng of GNA. Bound HCV E2 was detected with 5 µg/ml of biotinylated CBH-5 in the presence of 25 µg/ml of the indicated HMAbs (x axis). Results are compared to binding of biotinylated CBH-5 in the absence of any competitor. Bars indicate the mean value obtained from replicate wells. Error bars indicate one standard deviation from the mean.

FIG. 12 is a competition analysis showing the ability of the HCV HMAbs to interfere with the binding of HMAb CBH-2 to HCV E2 proteins of multiple genotypes. HCV E2 protein from cytoplasmic extracts of HeLa cells infected with vaccinia virus Q1a (Blue bars), Q1b (red bars), Q2a (yellow bars), or Q2b (light blue bars) was captured with 500 ng of GNA lectin. The HMAbs CBH-4D, -4B, and -17 were only evaluated with HCV 1a or 1b E2 protein due to their limited reactivity to genotype 2 E2 proteins. Bound HCV E2 was detected with 2 µg/ml of biotinylated CBH-2 in the presence of 20 µg/ml of the indicated HMAbs (x axis). The bars indicate the binding observed in the presence of the indicated antibody relative to binding of biotinylated CBH-2 to HCV E2 in the absence of any competing antibody (y axis). R04 is a control HMAb that recognizes a cytomegalovirus protein. Bars indicate the mean value obtained from replicate wells. Error bars indicate one standard deviation from the mean.

FIG. 13 is a competition analysis showing that HCV HMAb CBH-7 recognizes a unique epitope. HCV E2 protein from cytoplasmic extracts of HeLa cells infected with vaccinia virus Q1a (blue bars) or Q1b (red bars) was captured with 500 ng of GNA lectin. Bound HCV E2 was detected with 2 µg/ml of biotinylated CBH-7 in the presence of 20 µg/ml of the indicated HMAbs (x axis). The bars indicate the binding observed in the presence of the indicated antibody relative to binding of biotinylated CBH-7 to HCV E2 in the absence of any competing antibody (y axis). R04 is a control HMAb that recognizes a cytomegalovirus protein. Bars indicate the mean value obtained from replicate wells. Error bars indicate one standard deviation from the mean.

Figure 1:
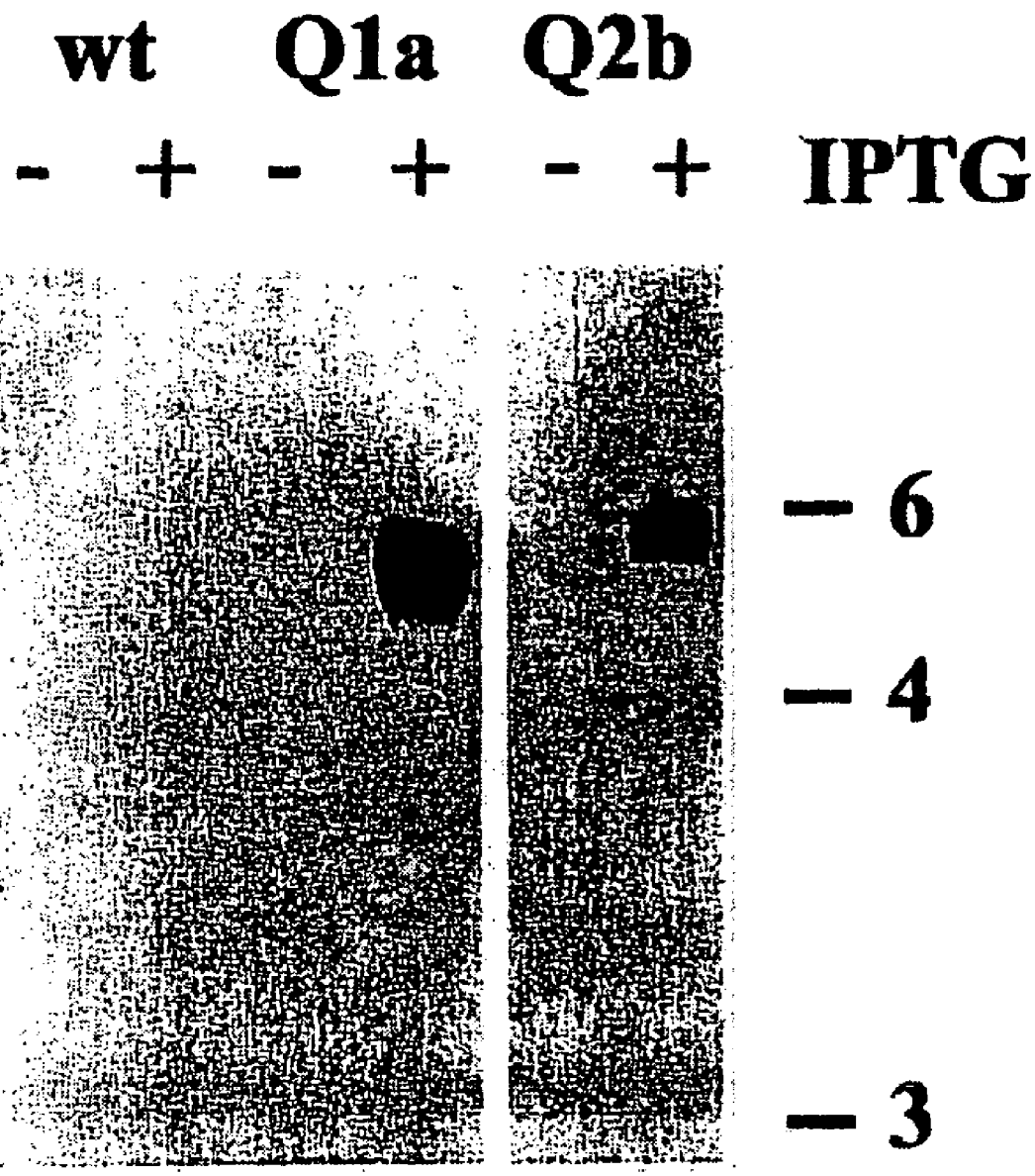
FIG. 1 is a Western blot indicating the expression of HCV E2 proteins by some of the vaccinia virus constructs described in this application. Cytoplasmic extracts were prepared from CV1 cells infected with wild type vaccinia virus and then transfected with pVOTE (wt) or recombinant pVOTE expressing HCV E2 of genotype 1a (Q1a) or 2b (Q2b). Cells were cultured for 24 hours in the presence (+) or absence (–) of the inducer IPTG. Extract corresponding to $2\times10^5$ cells was fractionated by SDS PAGE and blotted onto nitrocellulose. HCV E2 protein was revealed by incubation with 1/500 diluted ascites fluid of mMab E2G using the ECL detection system (Amersham). Migration of molecular weight standards is indicated at right.
Figure 14:
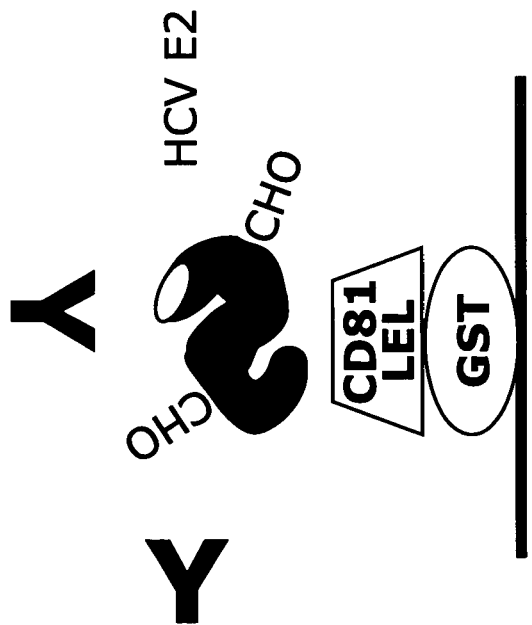

FIG. 14 depicts a schematic for assessing the ability of antibodies to block CD81 binding to E2 proteins as employed in the experiments described in FIG. 1. Recombinant CD81 is coated onto a solid surface. E2-containing protein extracts are then either added directly, or after preincubation with the test antibody. Bound test antibody-E2 complexes are detected using an appropriate labeled secondary antibody.

Figure 15:
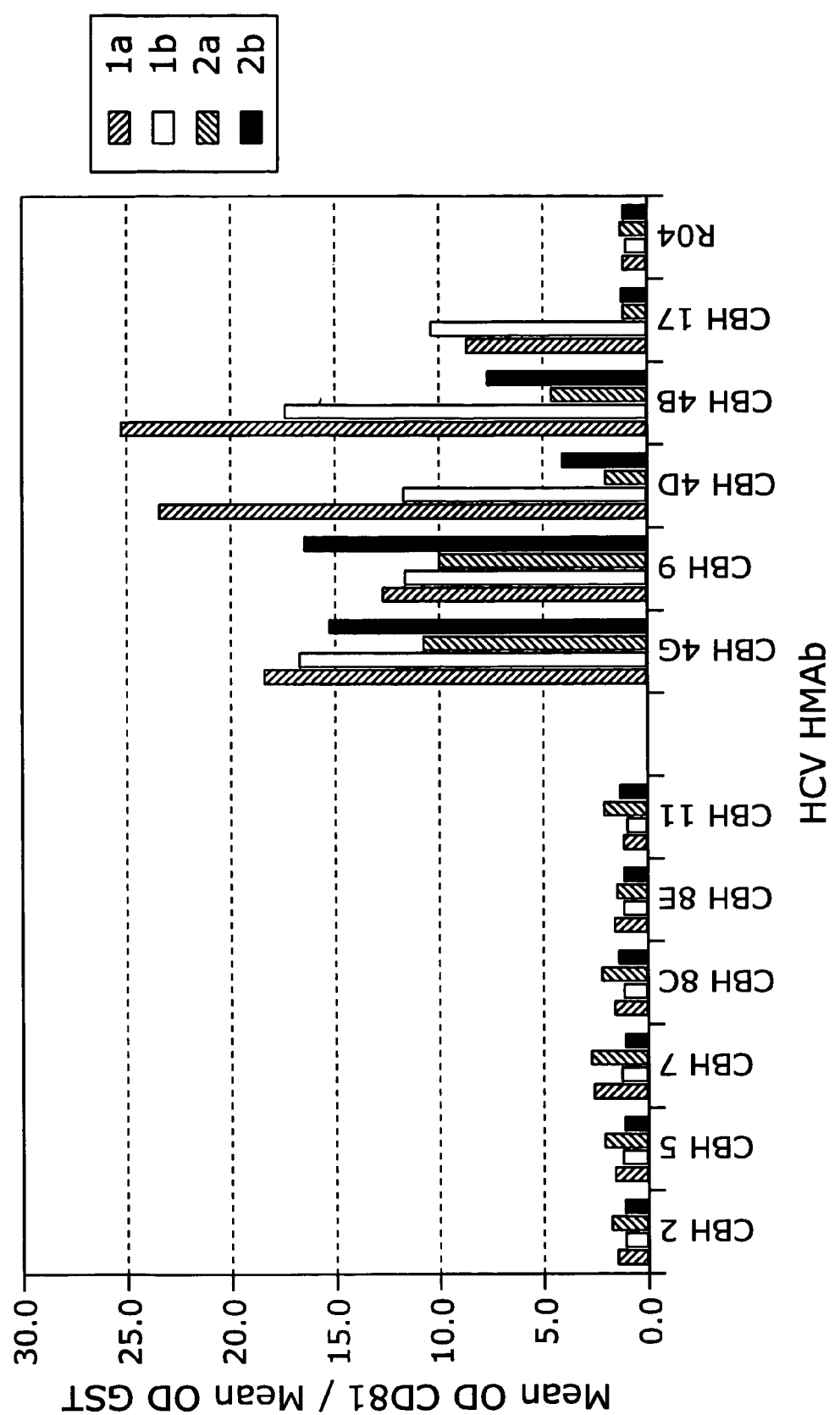

FIG. 15 is a bar graph that demonstrates that a subset of HCV HMAbs react with HCV E2 when bound to CD81-LEL. Extracts from BSC-1 cells infected with recombinant vaccinia virus expressing HCV E2 proteins were combined with 5 µg/ml of the indicated HMAbs (x axis) in a total volume of 100 µl and incubated in microtiter plate wells coated with 100 ng of a GST CD81-LEL fusion protein or non-recombinant GST overnight. Wells were washed and bound antibody was detected using an appropriate alkaline-phosphate conjugated secondary antibody and PNPP substrate as further described in Example 6. Values are the mean OD value of antibody captured by CD81 divided by the mean OD value for antibody captured by GST in the presence of 1a (purple bars), 1b (red bars), 2a (yellow bars), or 2b (green bars) E2 protein. OD values obtained from wells coated with GST ranged between 0.021 and 0.081.

Figure 16:
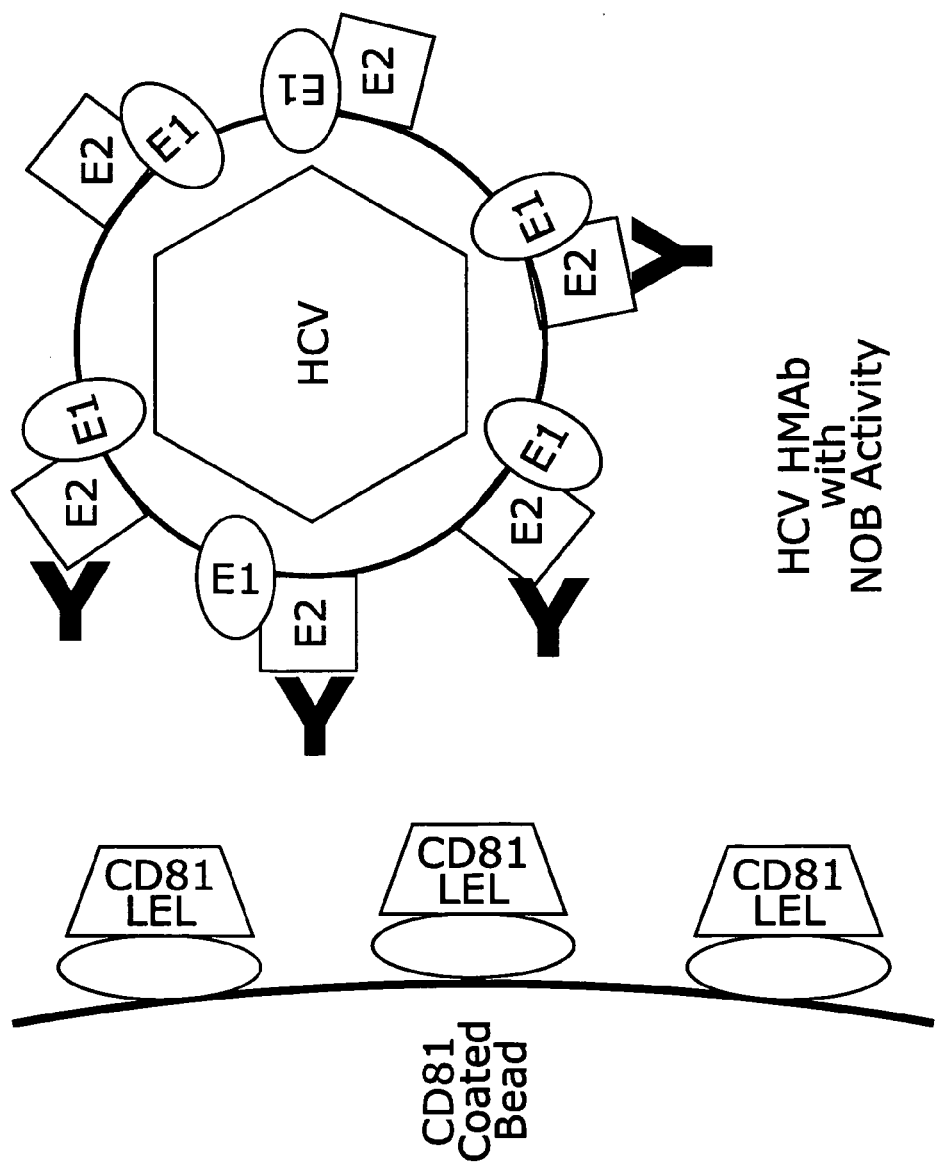
Figure 17:
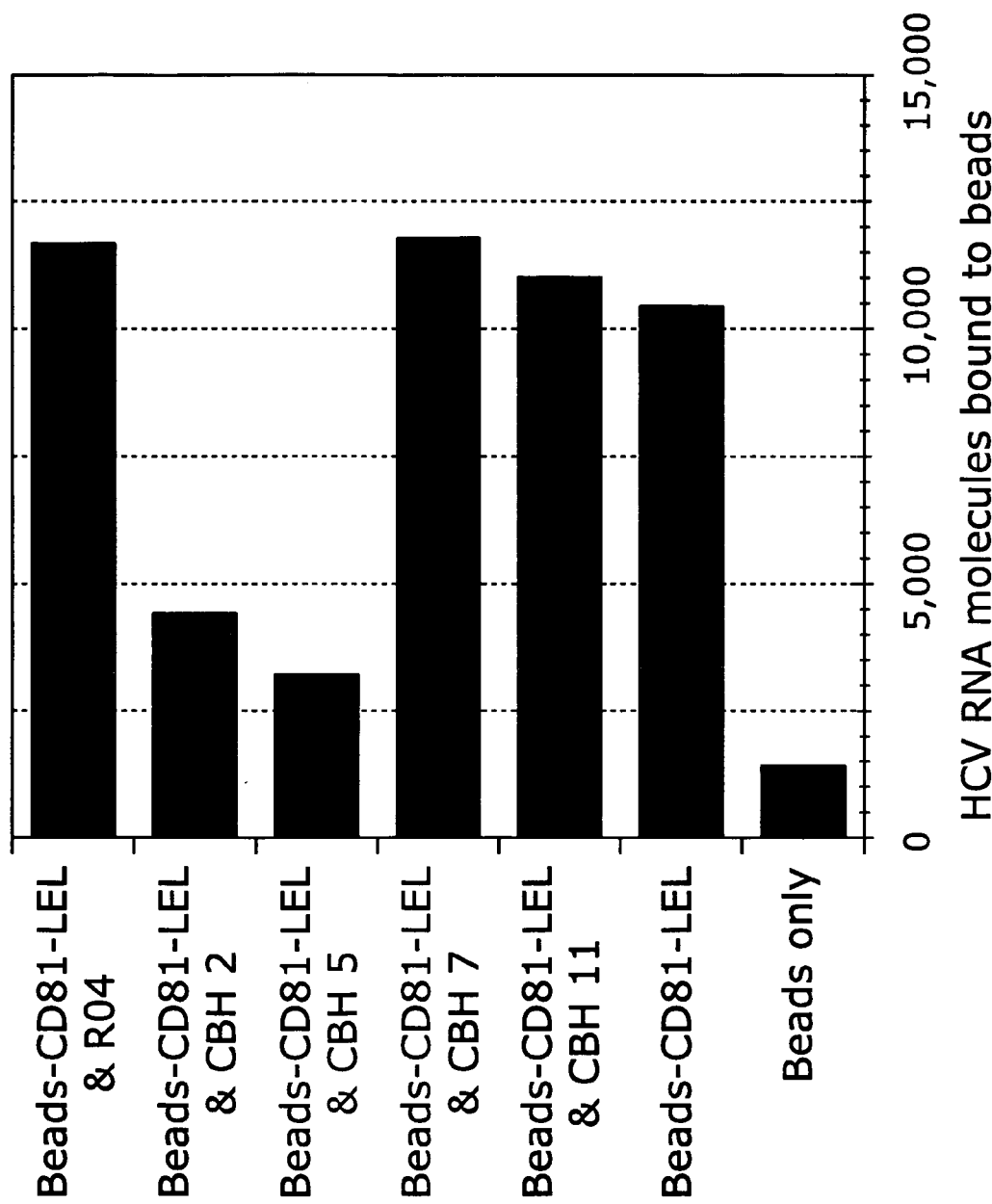

FIG. 16 depicts a schematic for assessing the ability of antibodies to block CD81 binding to HCV virions as employed in the experiments described in FIG. 17. Recombinant CD81 is coated onto a solid surface. HCV virions are preincubated with test antibodies, and then allowed to bind to immobilized CD81. Detection of bound HCV virions is measured by quantitative PCR.

FIG. 17 shows a bar graph demonstrating that HMAbs CBH-2 and CBH-5 inhibit binding of HCV virions to CD81. The number of HCV RNA molecules bound to polystyrene beads (x axis) after HCV 1a chimpanzee serum was combined with 10 µg of the indicated antibodies (y axis) and then allowed to bind to beads coated with CD81-LEL as described in Example 7.

Figure 18:
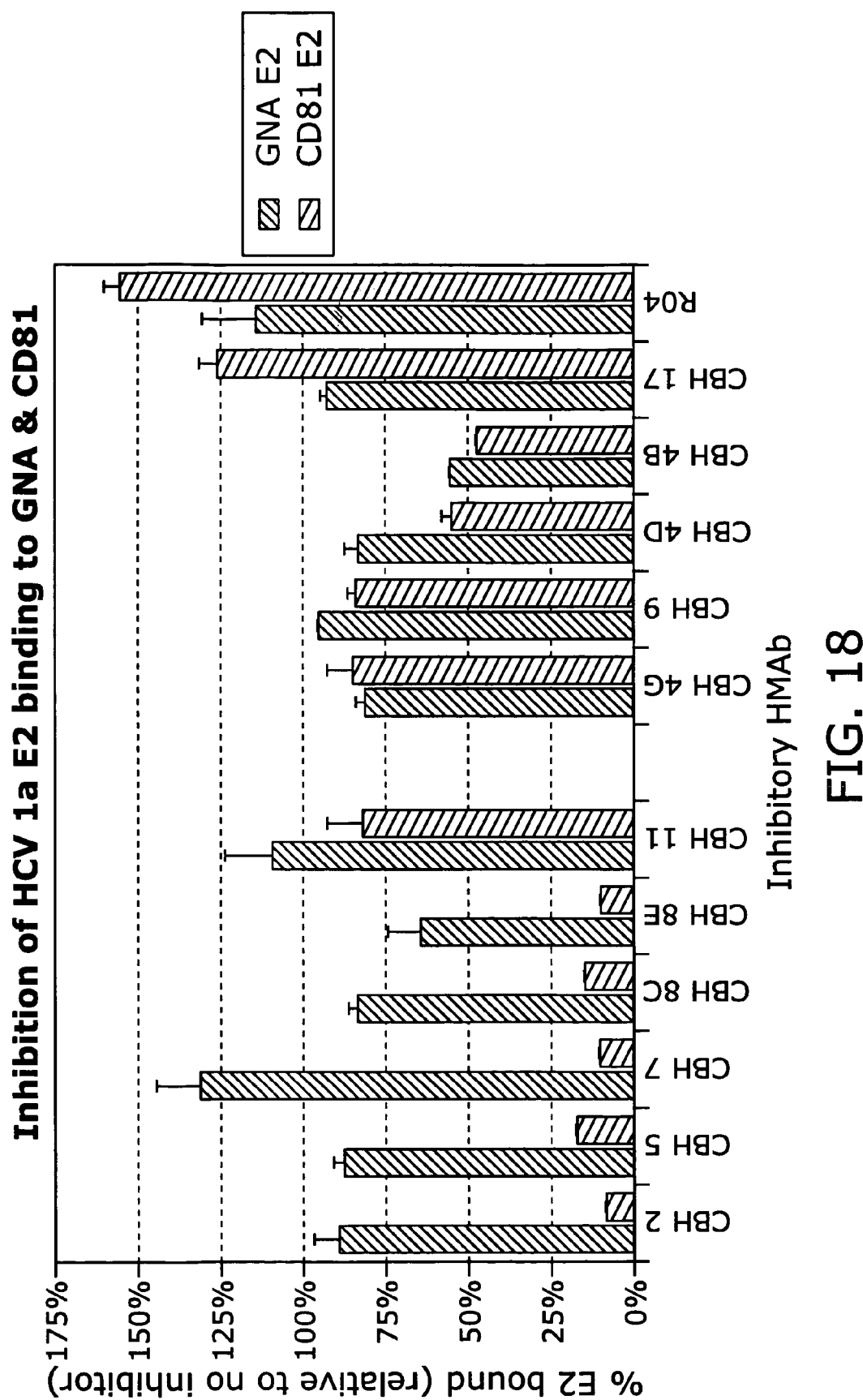

FIG. 18 is a bar graph that shows that HMAb CBH-4G can be employed to detect the presence of antibodies that inhibit binding of HCV E2 to CD81. HCV 1a E2 protein derived from extracts of BSC-1 cells infected with vaccinia virus Q1a was incubated with 4 µg/ml of a biotinylated preparation of HMAb CBH-4G for 20 minutes at 4° C. A 50 µl aliquot of the E2-CBH-4G complexes were then added to wells coated with either 500 ng of GNA (blue bars) or 100 ng of GST-CD81-LEL (red bars) to which 50 µl of a 40 µg/ml of the indicated antibodies (x axis) was added. R04 is a control HMAb that recognizes a cytomegalovirus protein. After an overnight incubation at 4° C. the wells were washed and bound biotinylated CBH-4G detected as described in Example 8. The bars indicate the mean signal obtained from duplicate wells in the presence of the indicated antibody relative to the signal obtained in the absence of any competing antibody. Error bars indicate one standard deviation from the mean.

Figure 19:
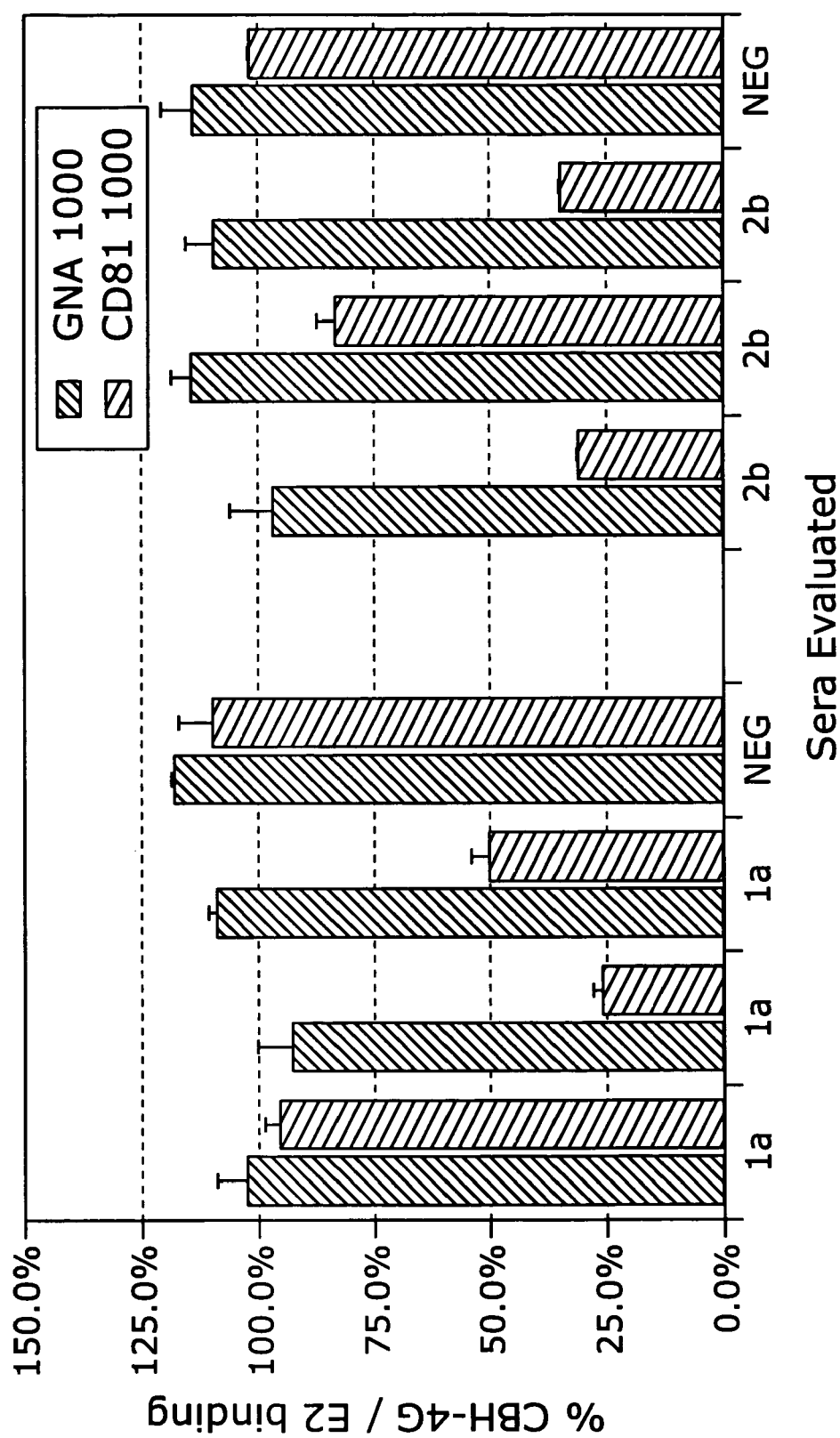

FIG. 19 is a bar graph that shows that HMAb CBH-4G can be employed to detect the presence of antibodies that inhibit binding of HCV E2 to CD81 in sera from HCV infected individuals. HCV 1a or 2b E2 protein derived from extracts of BSC-1 cells infected with vaccinia virus Q1a or Q2b was incubated with 4 µg/ml of a biotinylated preparation of HMAb CBH-4G for 20 minutes at 4° C. The four sera at left were tested with HCV 1a E2 protein, the four sera at right were tested with HCV 2b E2 protein. The E2-CBH-4G complexes were then added to wells coated with either 500 ng of GNA (blue bars) or 100 ng of GST-CD81-LEL (red bars) in the presence of a 1/500 dilution of the indicated sera from genotyped HCV infected (1a or 2b) or uninfected (NEG) individuals (x axis). After an overnight incubation at 4° C., the wells were washed, and bound biotinylated CBH-4G was detected as described in Example 8. The bars indicate the mean signal obtained from duplicate wells in the presence of the indicated serum (final dilution 1/1000) relative to the signal obtained in the absence of any competing serum. Error bars indicate one standard deviation from the mean.

FIG. 20 is a cartoon of the competition assay. Plates are first coated with GNA lectin which is used to capture full-length intracellular E2 onto microtiter plates by binding of CHO moieties to GNA lectin. Competing HMAb are contacted with the GNA-captured E2. Biotinylated test HMAb is added to the plates, and binding of the biotinylated test HMAb to E2 is detected using a streptavidin-AP conjugate. Inhibition of binding of test HMAb suggests epitopes within same antibody binding domain.

Figure 21A:
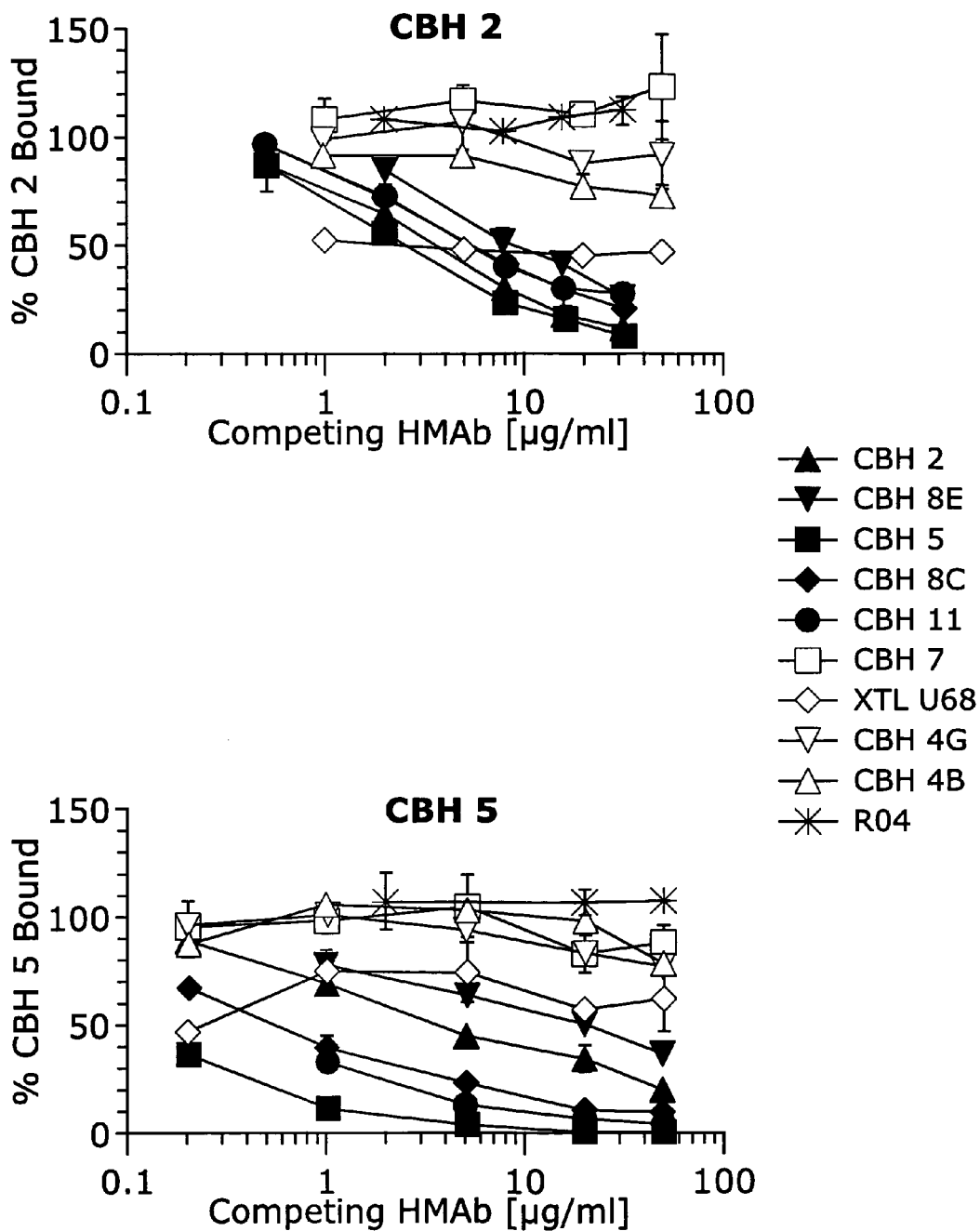
Figure 21B:
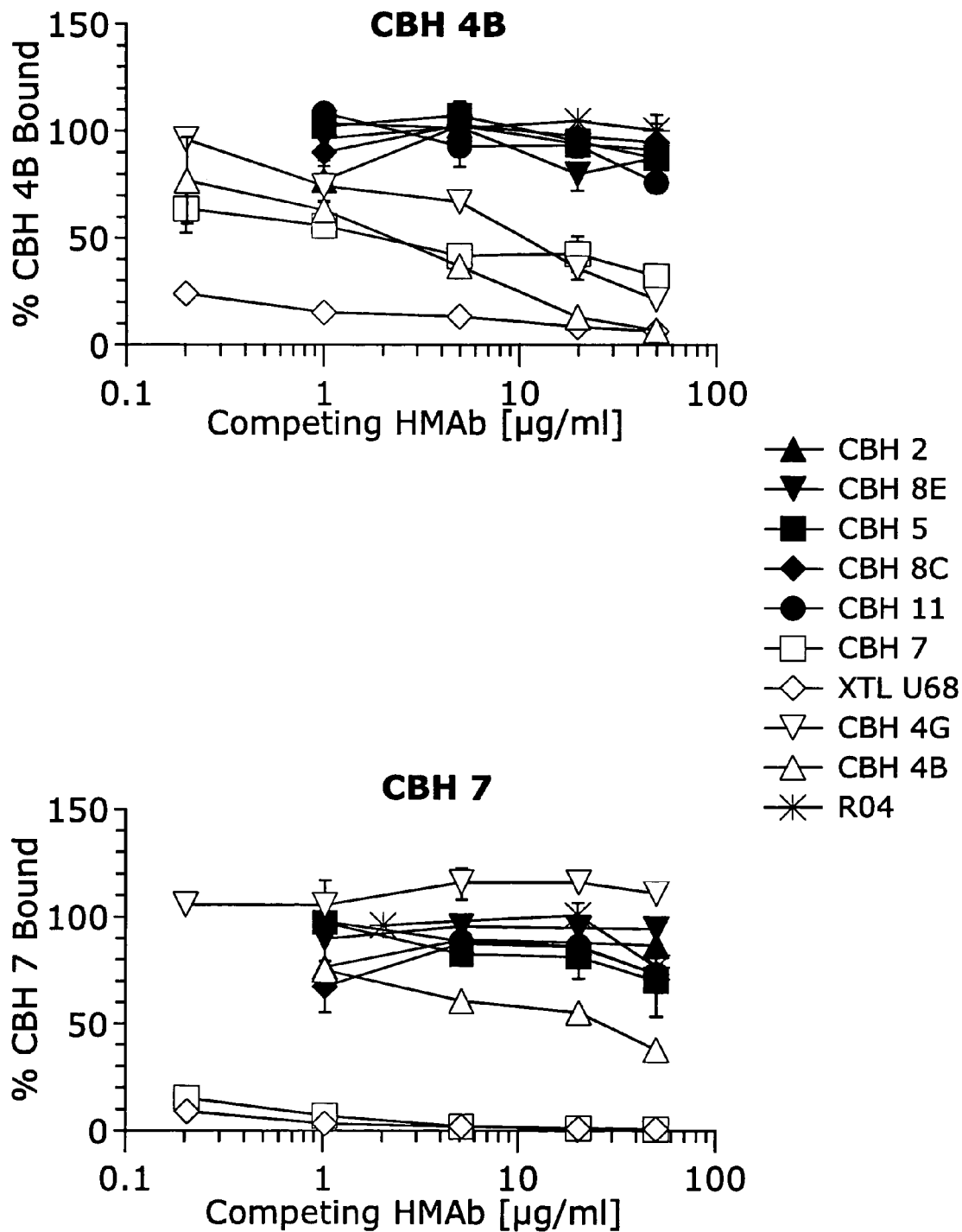

FIG. 21 shows competition analysis of four HCV human monoclonal antibodies. HCV Q1b E2 protein was captured onto GNA lectin coated microtiter plates. Biotinylated test antibody (indicated above each panel) at 2 µg/ml was added to wells containing the indicated concentration α-axis) of competing human monoclonal antibody. Bound biotinylated test antibody was detected using streptavidin alkaline phosphatase conjugate. Signal obtained in the presence of competing antibody was expressed as the percent of signal obtained by the biotinylated test antibody relative to the signal obtained in the absence of competing antibody (y-axis). The points indicate the mean value obtained from two replicate wells. The bars indicate one standard deviation from the mean. Competing antibodies are identified in the key at left.

FIG. 22 shows the results of a human monoclonal competition analysis. Results are the mean percent binding of test antibody relative to wells without any competing antibody. Results are the mean values obtained from 2–5 separate experiments. Both genotype 1a and 1b E2 proteins were tested. ND=not done.

FIG. 23 depicts HCV E2 deletion constructs described herein. The names of the E2 constructs are provided at left. Sequences derived from the vector pDisplay are indicated as solid black bars. The positions of the HA epitope and the c-myc epitope present in the pDisplay vector are also indicated. Sequences derived from HCV 1b E2 are indicated as white boxes. Sequences derived from HCV 1b E2 are indicated as light gray boxes. Numbering of the X-axis (below) is according to the polyprotein of the HCV-1 isolate.

Figure 24:
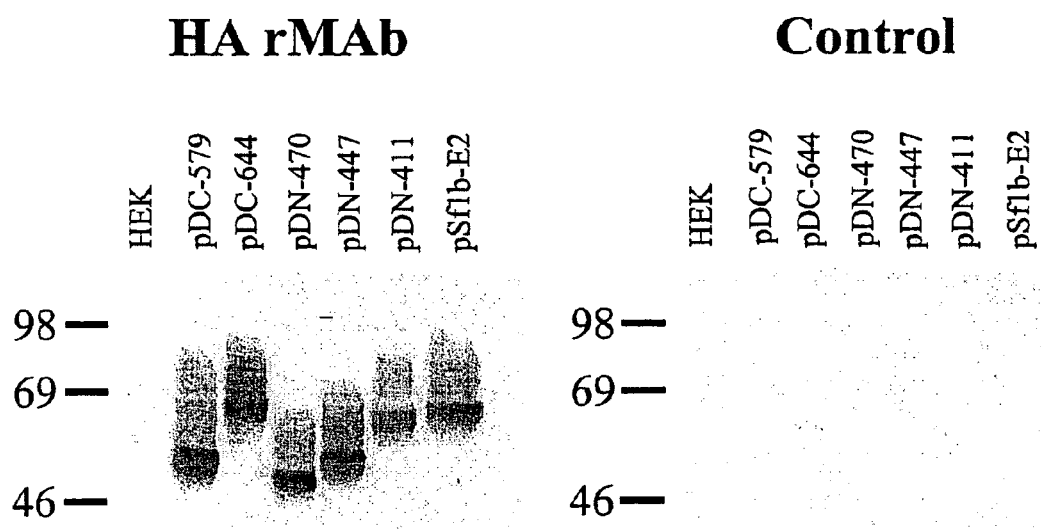

FIG. 24 shows Western blot analysis of HCV E2 deletion constructs indicating that the constructs are efficiently expressed. The indicated HCV E2 constructs (above lanes) were transfected into HEK-293 cells. Twenty-four hours after transfection cytoplasmic extracts were prepared and fractionated via SDS-PAGE. The fractionated proteins were transferred to nitrocellulose membranes and incubated with either rat monoclonal antibody to the HA epitope (HA rMAb) or a control HMAb to a CMV protein (control). Bound antibody was detected with the appropriate AP conjugated antisera. HEK=mock-transfected HEK-293 cells. The migration of molecular weight markers are indicated at left.

FIG. 25 shows reactivity of certain inventive human monoclonal antibodies with the various HCV E2 deletion constructs. HEK-293 cells were mock transfected (white bars) or transfected with the indicated HCV E2 constructs (see keys each graph). Twenty four hours post transfection cytoplasmic extracts were prepared and equivalent aliquots were captured onto GNA lectin coated microtiter plates as described above. The captured E2 proteins were then incubated with the indicated HCV HMAb (x-axis) and the amount of bound antibody was determined. Bars represent the mean-absorbance value obtained from duplicate wells. Error bars indicate one standard deviation from the mean.

Figure 26:
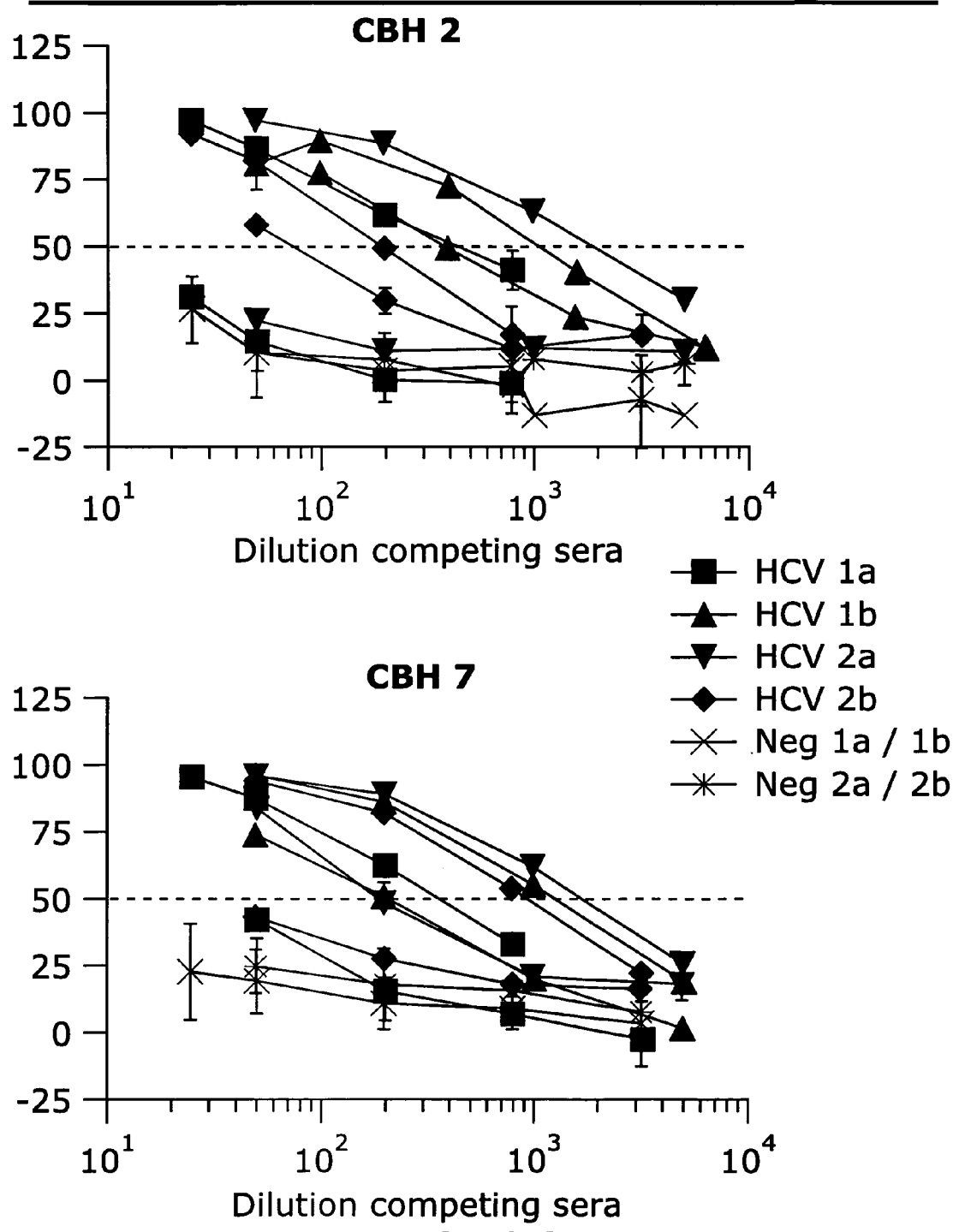

FIG. 26 shows graphs demonstrating that sera from HCV infected individuals have variable levels of antibodies that inhibit CBH-2 and CBH-7. Homologous HCV E2 proteins were captured onto wells and incubated with the increasing dilutions of HCV 1a, 1b, 2a, or 2b sera. Values are the specific inhibition of binding of biotinylated CBH-2 or CBH-7 obtained with individual sera. The mean percent inhibition (y-axis) obtained from duplicate determinations at a given dilution (x-axis) are plotted. The mean specific inhibition obtained for eight negative sera are also presented (genotypes of E2 proteins employed are indicated). Error bars on negative sera indicate one standard deviation from the mean.

Figure 27:
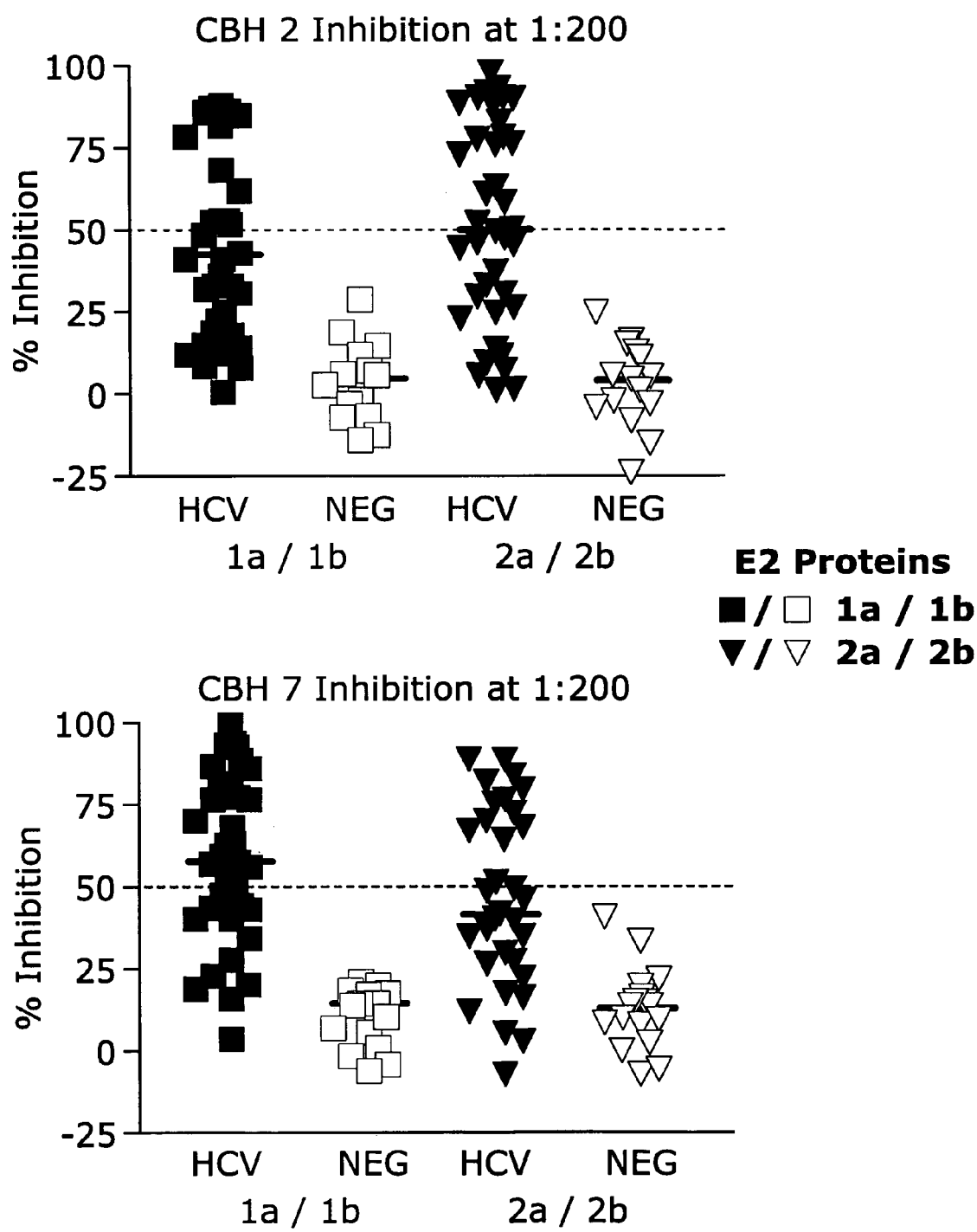

FIG. 27 shows scatterograms demonstrating that sera from HCV infected individuals have variable levels of antibodies that inhibit CBH-2 and CBH-7. Scattergram showing percentage of test HMAb inhibition. HCV sera of the indicated genotype (x-axis) or control sera (NEG) were diluted 1:200 and incubated with biotinylated test HMAb (indicated above graph) in wells coated with genotyped matched E2 proteins. Binding of test HMAb was detected using streptavidin-conjugated-AP. Results obtained were compared to binding of test HMAb in absence of competitor. Each symbol indicates results obtained with an individual serum. The line indicates the median percent inhibition. The dotted line indicates the cutoff for calling a serum positive for the presence of the test HMAb.

Figure 28:
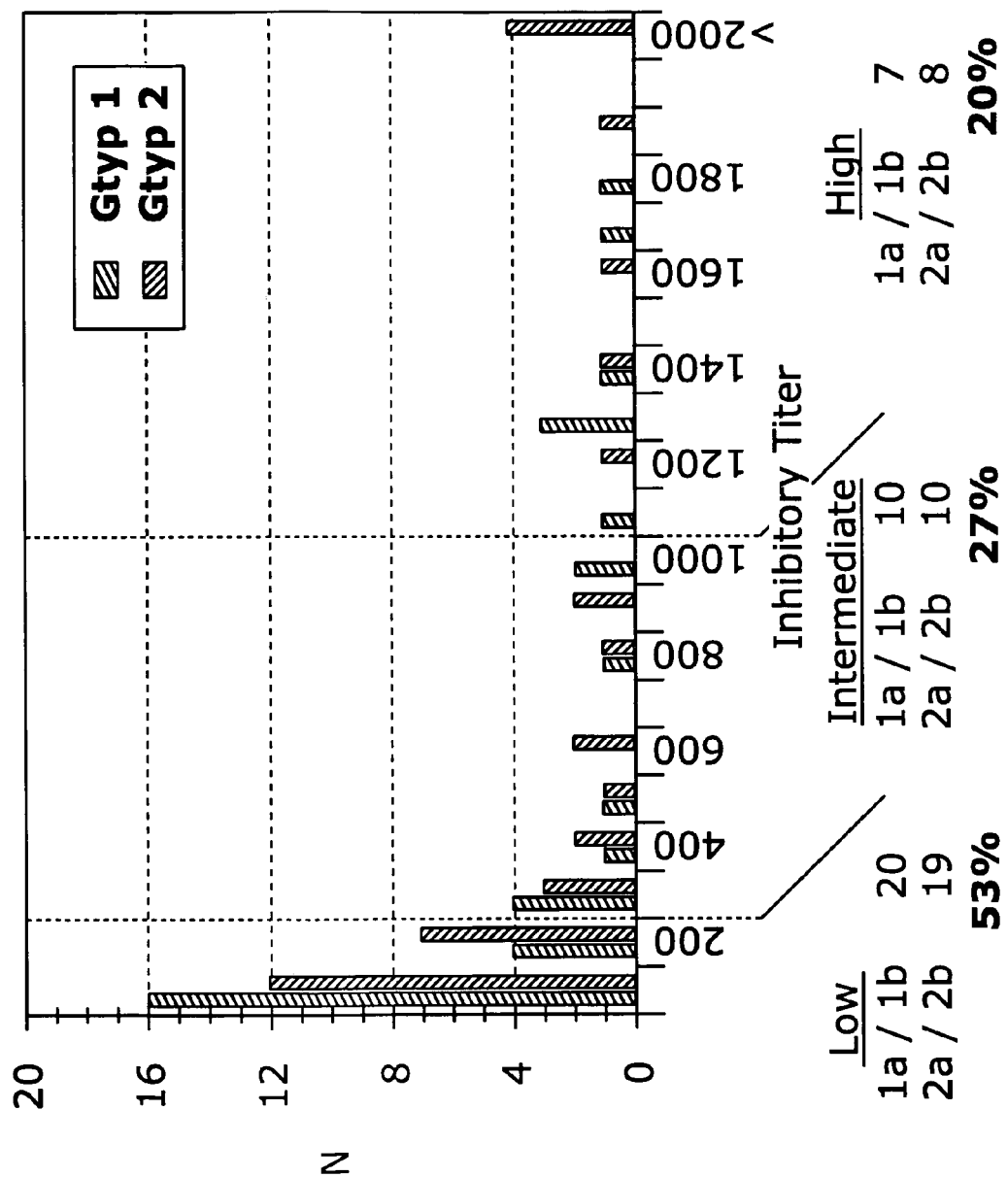

FIG. 28 is a histogram of CBH-2 inhibitory titers obtained from a panel of 74 individuals with chronic hepatitis. The CBH-2 inhibitory titers obtained with individual serum were segregated into 20 bins of 100 and 1 bind for all titers >2000. The bars indicate the number of sera having a CBH-2 inhibitory titer within a given bin. Numbers of HCV 1a/1b sera are indicated in black. Number of HCV 2a/2b sera are indicated in gray. The number of sera with low (<200), intermediate (200–1000), and high (>1000) inhibitory titers are indicated below the graph.

Figure 29:
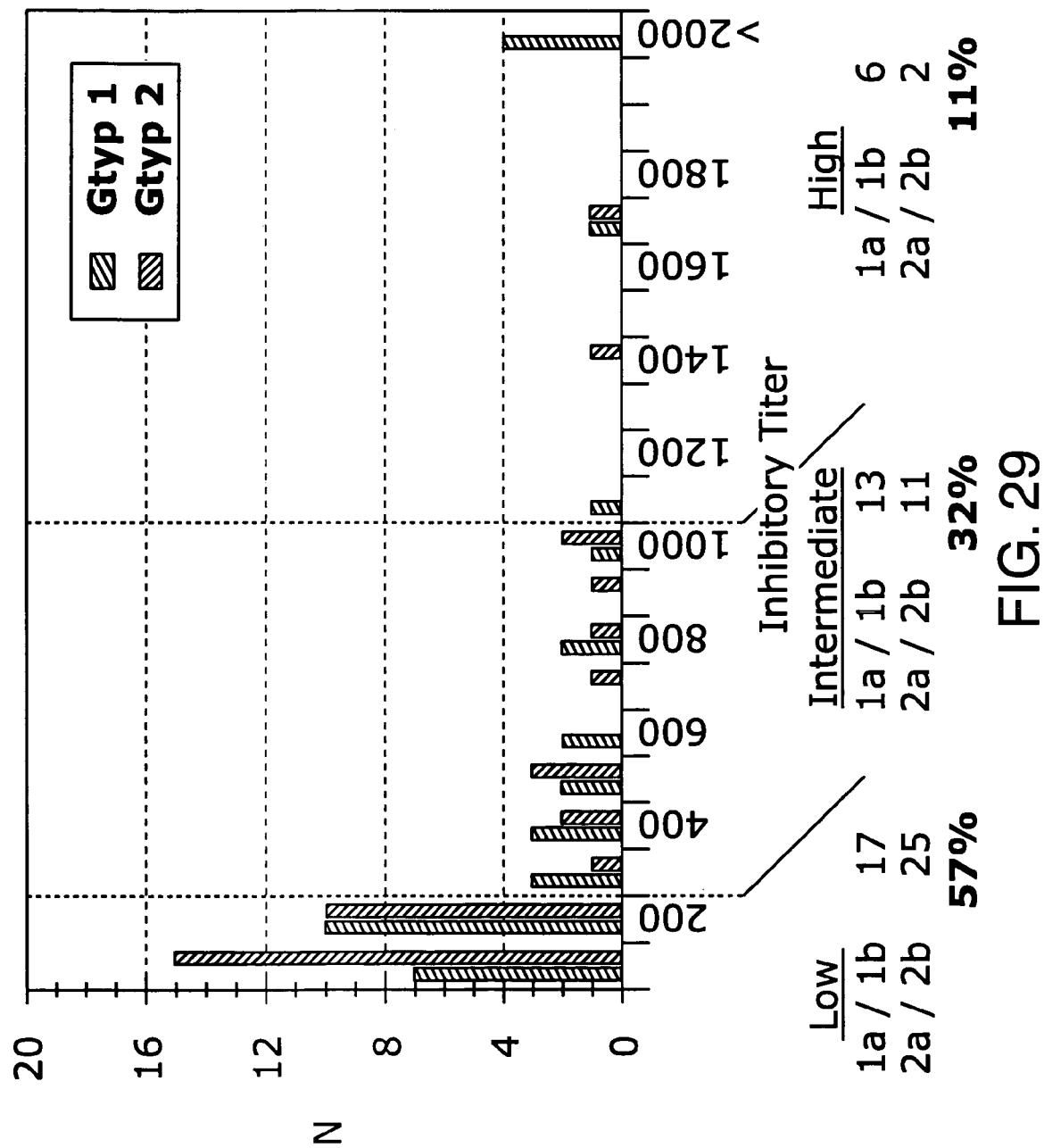

FIG. 29 is a histogram of CBH-7 inhibitory titers obtained from a panel of 74 individuals with chronic hepatitis. The CBH-7 inhibitory titers obtained with individual serum were segregated into 20 bins of 100 and 1 bin for all titers >2000. The bars indicate the number of sera having a CBH-7 inhibitory titer within a given bin. Numbers of HCV 1a/1b sera are indicated in black. Number of HCV 2a/2b sera are indicated in gray. The number of sera with low (<200), intermediate (200–1000), and high (>1000) inhibitory titers are indicated below the graph.

DETAILED DESCRIPTION OF CERTAIN PREFERRED EMBODIMENTS OF THE INVENTION

Monoclonal antibodies, particularly human monoclonal antibodies ("HMAbs"), are provided which bind to one or more hepatitis C virus genotypes, which antibodies find use for diagnosis and therapy. A panel of human monoclonal antibodies (HMAbs) from peripheral B-cells of an individual with asymptomatic HCV infection and having a high serum neutralization of binding titer were produced and characterized. Eleven HMAbs to HCV E2 have been produced. One group of antibodies binds to the genotypes of HCV types 1 and 2, while other antibodies bind to fewer than this group of genotypes. HCV types 1 and 2 together are the dominant virus types encountered in the western hemisphere and other geographic locations. The antibodies bind to conformational epitopes which are conserved across virus types and genotypes. The antibodies bind to HCV E2 proteins of genotypes 1a, 1b, 2a, and 2b and a subset of these antibodies inhibit the interaction of these E2 proteins with human CD81. By virtue of the variety of binding profiles of the antibodies, diagnostic assays may be employed which will detect a plurality of types and genotypes, so as to provide a pan-anti-HCV antibody for HCV encountered in the United States, while at the same time being able to dissect individual genotypes by subtractive analysis. In addition, the antibodies being human may be used for passive immunization, as protective therapy for individuals at risk for HCV or as a therapy for people who are seropositive for HCV.

The HMAbs of the invention offer several advantages over existing HMAbs against HCV. Because non-homologous primary amino acid sequences may still define immunologically identical tridimensional protein structures, HMAbs binding to structurally conserved epitopes can recognize multiple, sequentially divergent HCV genotypes in native conformation, whereas antibodies recognizing only linear or denatured epitopes may not. In particular, conformationally dependent anti-HCV E2 HMAbs may effectively interfere with the interaction of native HCV virus and its cellular target receptors. Using conformationally dependent HMAbs to actively interfere with the ability of native HCV virus to bind to target cell receptors such as CD81 has specific therapeutic application for reducing viral load in infected individuals, and preventing infection or re-infection of organs in non-infected individuals, particularly in recent organ transplant recipients. Certain subsets of the HMAbs interfere with E2-associated viral infection by mechanisms other than preventing direct interaction with CD81. This subset of antibodies interferes with viral infectivity by a number of possible mechanisms, including preventing E2 binding to co-receptor proteins, conformational changes in E1 and/or E2 proteins necessary for target cell binding, E1 and E2-mediated viral fusion to target cells, and uncoating of HCV virions. Because they bind distinct conformational epitopes, the subset of HMAbs that directly interferes with E2 binding to CD81 complements HMAbs in the subset that interfere with infectivity by other mechanisms for both therapeutic and diagnostic applications.

HMAbs which recognize conformationally-defined viral epitopes and interfere with virus/target receptor interaction, and viral conformational epitopes which bind to such HMAbs, may also serve as templates for rationally designing peptide and other structural mimics of the viral epitopes. Structural molecular mimics defined by these conformationally dependent anti-HCV HMAbs find use in their ability to block binding of the native virus to target receptors by binding to the target receptor themselves.

By producing human monoclonal antibodies, it is possible to directly analyze the human immune response to HCV. Importantly, by using human monoclonal antibodies, immune responses against the antibodies themselves as foreign antigens are minimal, whereas vigorous immune responses are generated against monoclonal antibodies produced from non-human sources, because they are recognized as foreign antigens. Selecting for HMAbs that recognize conserved viral conformational epitopes affords broader and more effective therapeutic application of these reagents for ameliorating or preventing HCV infection than antibodies able to bind only linear or denatured epitopes. All previous antibodies described as having the property of preventing HCV infection or uptake into target cells recognize a highly variable sequence of HCV E2 known as the hypervariable region. In contrast, the antibodies described above recognize conformational epitopes, the majority of which are highly conserved HCV E2 proteins of multiple different genotypes. Thus the antibodies described herein have the advantage that they are active against a much wider range of HCV isolates than previously described neutralizing antibodies. An additional advantage is that the high conservation of the epitopes recognized by the antibodies described herein indicates that these antibodies recognize sequences with functional and/or structural significance within the HCV E2 protein. Thus peptides or small molecules isolated with these antibodies have a high probability of being targeted to functional regions within HCV E2. This is not true for other HVC antibodies described to date.

Of the detection antibodies described, CBH-4G has essentially equal reactivity to HCV E2-CD81 complexes of multiple HCV genotypes, whereas CBH-4B recognizes HCV genotypes 1a and 1b. The level of interfering antibodies present in HCV antisera has also been shown to be quite low. Therefore they provide a straight forward means of assaying the level of neutralizing antibodies present in a sample in a microtiter plate format without resorting to multiple flow cytometric analyses.

Mouse/human heteromyeloma cell lines expressing monoclonal antibody CBH-4B and CBH-4G were deposited on Jun. 18, 2002 with the American Type Culture Collection (ATCC) (10801 University Blvd., Manassas, Va. 20110-2209) and assigned ATCC numbers PTA-4466 and PTA-4468, respectively. Also included in this deposit were other mouse/human heteromyeloma cell lines expressing antibodies CBH-2 (PTA-4465), CBH-4B (PTA-4466), CBH-4D (PTA-4467), CBH-4G (PTA-4468), CBH-5 (PTA-4469), CBH-7 (PTA 4470), CBH-8C (PTA-4471), CBH-11 (PTA-4472), and CBH-17 (PTA-4473), described herein below.

The overall strategy employed for the development of the subject HMAbs was as follows: (1) individuals with evidence of exposure to HCV were identified; (2) antigen specific B-cells from their peripheral blood were expanded and activated in vitro; (3) these cells were immortalized by electrofusion with a suitable mouse-human heteromyeloma; (4) relevant human antibody secreting hybridomas were identified; and (5) the relevant hybridomas were stabilized by cloning. This strategy resulted in the identification of HMAbs which are specific to the HCV E2 protein, a number of which bound to conformation epitopes of E2 of type 1 genotypes 1a and 1b and type 2 genotypes 2a and 2b, so as to recognize the primary genotypes encountered in the United States and elsewhere with a single antibody, while others bound to fewer of the indicated genotypes, so as to be useful in identifying an HCV type or genotype.

As an example, peripheral B cells from an individual with asymptomatic HCV infection and a high serum neutralization of binding titer were used to produce and characterize a panel of human monoclonal antibodies. The initial screening made use of a genotype 1a E2 protein having an amino acid sequence with 98% homology to the same region of the HCV-1 isolate (Lanford et al., 1993 *Virology* 197:225–235; incorporated herein by reference). This step biased the screening approach used to the selection of antibodies to epitopes conserved between genotypes 1a and 1b since the donor was infected with a 1b isolate. All of the HMAbs also reacted with E2 from a heterologous HCV 1b isolate, Q1b, that was 79% homologous with the HCV 1a isolate employed in the selection of HMAbs. Denaturation of recombinant E2 completely abrogated the reactivity of 10 of 11 HCV HMAbs. Thus, the majority of the HMAbs recognized conformational epitopes.

Five HMAbs, CBH-4D, -4B, -4G, -9, and -17, were negative in the NOB assay and reacted with HCV E2-CD81 complexes. Two of these antibodies, CBH-4G and CBH-9, reacted with HCV E2 proteins of genotypes 1a, 1b, 2a, and 2b in both the GNA and CD81 capture assays. The other three antibodies, CBH-4B, -4D, and -17, exhibited restricted reactivity to E2 proteins of genotypes 1a and 1b. HMAbs CBH-4B and CBH-4D have kappa and lambda lights chains, respectively, and probably recognize different epitopes. HMAb CBH-17 was the only antibody to recognize a denaturation insensitive epitope. Thus it is likely that each of the NOB negative antibodies recognizes a distinct epitope.

Six of the HMAbs recognizing conformational epitopes, CBH-2, -5, -7, -8C, -8E, and -11, were positive when tested with the neutralization of binding assay using HCV 1a E2 protein. Five of these antibodies HMAbs CBH-2, -5, -7, -8C, and -8E reacted with E2 proteins of all tested genotypes. The same six antibodies failed to bind to E2 of genotypes 1a, 1b, 2a, or 2b when complexed to CD81-LEL. Thus epitopes that partially or fully overlap the CD81 binding site within HCV E2 are both conformational in nature and highly conserved. A high degree of sequence conservation in the CD81 binding site is consistent with the proposition that the interaction between HCV E2 and CD81 is biologically relevant. Two of the four NOB positive antibodies tested, HMAbs CBH-2 and CBH-5 were able to prevent the binding of intact HCV virions to CD81. The HMAbs CBH-7 and CBH-11 did significantly inhibit binding of HCV virions to CD81, despite the antibodies having equivalent activity in the NOB assay. This may reflect the fact that HCV virions are thought to have E1–E2 complexes at their surface, and that not all of the epitopes present in E2 may be exposed in such complexes. Testing of the HMAbs with E1–E2 complexes may shed light on this issue. Alternatively, the differential results in the NOB and virion inhibition assays may reflect differences in the true affinity of the HMAbs for the E2 protein or E1–E2 complexes. In any event, a strong neutralization of binding activity in and of itself does not ensure that an antibody will bind to intact HCV virions. Thus it is probable that not all antibodies inhibiting the interaction of E2 protein with CD81-LEL in vitro will neutralize infectivity in vivo.

Five of these six NOB positive antibodies are to epitopes shared among the five HCV isolates used in this study. The other antibody CBH-11 exhibited differential reactivity to two 1a isolates and probably recognizes an epitope distinct from the other antibodies. Indeed the variable reactivity of CBH-11 to different 1a isolates may have contributed to its negative result in the virion binding experiment. Both the differential reactivity of CBH-2 and CBH-7 with HCV virions and competition experiments indicate that CBH-2 and CBH-7 recognize distinct epitopes. Competition experiments also suggest that the epitopes recognized by HMAbs CBH-5 and CBH-2 are distinct. It remains possible that CBH-2 and CBH-8E recognize the same or very similar epitopes, however. Determining the total number of unique epitopes will require sequencing of the antibody genes produced by the hybridomas as well as competition studies and testing with additional HCV isolates.

Competition analysis (FIG. 22) has been employed to define antibodies with similar binding sites in HCV E2. Seven HMAbs were biotinylated and the binding of the biotinylated antibodies to HCV E2 in the presence of increasing amounts of competing HCV HMAbs was determined. Antibodies that cross-competed significantly were grouped together. Regions of HCV E2 that contained the binding sites were localized using a series of HCV E2 deletion constructs (FIG. 23). Four competition groups were defined. Group I consisted of five HMAbs, CBH-2, -8E, -5, -8C, and -11. Antibodies from this group inhibit binding of HCV E2 to CD81 and recognize conserved epitopes localized to HCV E2 amino acids 411 to 644. Group II consists of HMAbs CBH-7 and XTL-U68, which recognize a highly conserved epitope located between HCV E2 amino acids 470–644. Antibodies from groups I and II exhibited minimal cross-competition. Group III consisted of three antibodies, CBH-4G, -4B, and -4D, that do not inhibit binding of HCV E2 to CD81 and recognize epitopes between HCV E2 amino acids 470 to 644. Group IV consisted of one antibody, CBH-17, that recognized an epitope located between HCV E2 amino acids 644 to 661. Antibodies in group I and II have been found to inhibit HCV replication in a small animal model and recognize two distinct conserved binding sites outside of the hypervariable region of E2. The low level of competition between antibodies of groups I and II should lead to additive virus neutralization activity and raises the possibility that these antibodies might act synergistically in vivo.

These results indicate that several conformational epitopes within HCV E2 are highly conserved among divergent HCV genotypes. The antibodies that recognize these epitopes are useful as reagents to better define the structure of HCV E2. Furthermore, the antibodies that inhibited binding of HCV virions to human CD81, CBH-2 and CBH-5, are prime candidates to mediate virus neutralization. The absence of a true in vitro model for virus neutralization, however, will require that the fundamental proof be obtained by the ability of selected HMAbs to prevent or modify HCV infection in appropriate animal models. If successful, broadly reactive neutralizing antibodies will likely have therapeutic utility. Analogous to the success achieved with hepatitis B immunoglobulin in liver transplantation (Dickson, 1998 *Liver Transpl. Surg.* 4(5 Suppl 1):S73–S78; Markowitz et al., 1998 *Hepatology* 28:585–589; each of which is incorporated herein by reference), one possible application is to suppress HCV infection in liver transplant recipients with broadly reactive neutralizing human monoclonal antibodies.

While human monoclonal antibodies are provided, other antibodies from other sources may recognize the same epitopes recognized by the human antibodies described herein, and may also be employed. Generally antibodies from murine sources, mice and rats, lagomorpha and domestic animals find use. One may produce antibodies having the conserved regions of these mammalian sources using genetic engineering and replacing the constant regions of the HMAbs provided herein or may use the proteins to be described below as immunogens for immunizing the animals and then immortalizing the resulting B cells and screening as described below for immortalized cells which produce monoclonal antibodies having analogous broad range binding specificity. By screening in competitive assays with the subject HMAbs, one can determine whether the non-human antibodies bind to the same epitope.

For diagnosis, the antibodies may be used in a variety of ways, for capturing and/or identifying circulating HCV virions, E2 protein or anti-E2. The antibodies may be used for immunotherapy, prophylactic or therapeutic. The antibodies may also be used for development of vaccines for HCV.

The antibodies are the IgG class, particularly $IgG_1$. The following are the designations for the antibodies and the HCV genotypes which the antibodies recognize. All of the HMAbs exhibited good affinity for HCV E2 proteins, with the antibodies exhibiting maximal signals at concentrations ranging between 1 to 20 μg/ml.

TABLE 1

HCV Genotypes bound by HMAbs

| Antibody | Genotypes bound |
|---|---|
| CBH-2 | 1a, 1b, 2a, 2b |
| CBH-4D | 1a, 1b |
| CBH-4B | 1a, 1b |
| CBH-4G | 1a, 1b, 2a, 2b |
| CBH-5 | 1a, 1b, 2a, 2b |
| CBH-7 | 1a, 1b, 2a, 2b |
| CBH-8C | 1a, 1b, 2a, 2b |
| CBH-8E | 1a, 1b, 2a, 2b |
| CBH-9 | 1a, 1b, 2a, 2b |
| CBH-11 | —, 1b, 2a, 2b |
| CBH-17 | 1a, 1b |

The antibodies may be used in their native form or may be truncated to provide Fab or $F(ab')_2$ fragments. The genes encoding the heavy and light chains may be isolated and modified in a number of different manners. Conveniently, using RT-PCR, the cDNA may be obtained for the genes in a convenient construction for further manipulation. The nucleotide sequences of the variable regions of the heavy and light chains may be isolated and joined, either directly or indirectly or through a chain of 3n nucleotides, where n is at least 1 and not more than about 60, usually not more than about 40, to provide a linker of amino acids between the two variable regions. The length of the chain can be determined empirically to provide the optimum affinity and other properties, e.g., linkage through mercapto, carboxy, or amino groups, for chelation, bonding to a surface or other molecule, or the like. In addition, the genes, intact or portions thereof, including at least the variable regions, may be fused to other sequences to provide for each of attachment to a surface, toxins for cytotoxicity, labels or tags for identification, sequences for affinity isolation, and the like.

Where labels are polypeptides, the sequence can be directly fused to a gene of one of the antibody chains. In any case, sequences may be provided which provide a site for linking a label, such as cysteines for forming thioethers with maleimide groups, polyhistidine/cysteines or polyhistidines/aspartic acids for chelating metals, which may be bonded to a variety of molecules, polylysines for reacting with aldehydes in reductive animation reactions, etc. Labels may include enzymes, chelating groups, ligands for binding to a ligand binding proteins, e.g., biotin and streptavidin, digoxigenin and antidigoxigenin, etc., green fluorescent protein, and the like. The biotinylation sequence of *E. coli* biotin carboxylase carrier protein (BCCP) can be used for in vivo biotinylation of proteins expressed in *E. coli* or introduced in a lysate of *E. coli*. A sequence of six histidines or a sequence of alternating histidines and aspartic acids that are suitable for allowing binding of the antibody to a column containing immobilized divalent cations can be used. Sequences encoding high affinity epitopes may be employed, such as the FLAG epitope DYKDDDDK (SEQ ID NO: 13), the T7 tag sequence MASMTGGQMG (SEQ ID NO: 14), the S-tag sequence KETAAAKFERQHMDS (SEQ ID NO: 15), or any other sequence that confers high affinity binding to its correlative binding member or a protein reagent. Fusion proteins, besides the ones indicated above, include glutathione-S-transferase, luciferase, ligands to cell surface receptors found on hepatocytes, T-cells or other desirable cellular target, and the like. Such fusions are usually joined via a linker sequence of 3–50 amino acids that promotes the bi-functionality of the protein. These molecules can be linked to the antibodies via cleavable arms (protease sites) or other means. The antibodies may be chemically linked or fused to various toxins, such as diphtheria toxin, ricin, abrin, ribosome inactivating proteins, apoptosis signaling proteins, pore forming proteins, e.g., perforin, and the like. Alternatively, the antibodies may be linked to chelated toxic heavy metals or radioactive isotopes, particularly technetium, radioactive iodine or the like. The antibodies may be chemically linked to fluorophores or chemiluminescent molecules. Chemical coupling may involve biotinylation using the activated carboxylic acid group or biotin-C11-hydroxysuccinimide ester, which will react with cysteines; coupling through the use of CNBr activation of various beads (sepharose, agarose, magnetic, polystyrene, etc.) or surfaces to link the antibodies, and the like; any number of other methods generally involving bridging the antibody to a useful chemical moiety, usually accomplished by modifying lysine or other basic residues or through use of reagents specific for free sulfhydryl groups.

Using the genes for the heavy and light chain variable regions, particularly the hypervariable regions of the variable region may be mutated in accordance with known ways to enhance the binding affinity of the antibody or to broaden reactivity. One may use in vitro selection to identify the optimum binding antibodies using phage display methodologies, random or directed mutagenesis of sequences, or other similar methodologies. Alternatively, one may use an alanine or glycine walk of the hypervariable regions to identify essential amino acids and then vary the amino acids at those or other sites to identify improved binding of the epitope. Other techniques known in the art may be employed to provide the mutagenized antibodies.

Instead of using the hybridomas as a source of the antibodies, the genes may be isolated and introduced into an appropriate mammalian host cell, e.g., CHO, HeLa, CV1, or the like. Suitable expression plasmids are exemplified by pcDNA3.1 Zeo, pIND(SP1), pREP8 (all available from Invitrogen, Carlsbad, Calif.), and the like. The antibody genes may be expressed via viral or retroviral vectors, which may be exemplified by MLV based vectors, vaccinia virus based vectors, etc. Similarly, the antibody genes may be expressed using the pCOMB series of vectors on the surface of M13 phage, as two independent chains which may be renatured to form the intact antibody. Alternatively, the antibodies may be expressed as a single chain, including at least the variable regions. The genes may be used for gene therapy by introducing the genes into appropriate cells, such as lymphocytes, muscle cells, fibroblasts, and the like, where the antibodies may be expressed and secreted, either constitutively or inductively, to provide a continuous or intermittent source of the antibodies over a predetermined period of time, based on the lifetime of the host cell. The genes in conjunction with a marker gene, e.g., antibiotic resistance, may be introduced in cell cultures of cells taken from a subject, the modified cells selected by means of the marker and the marked cells returned to the host. The DNA may be introduced into the cells using various plasmid DNA, naked DNA, DNA virus constructs, such as adenovirus, adeno associated virus, or vaccinia virus or RNA viruses such as Vesicular stomatitis virus, sindbis virus, and semiliki forest virus to name but a few. The DNA would have a construct having a promoter for which transcription factors are present in the subject cells or can be induced or introduced and the genes under the transcriptional control of such promoter. Other regulatory sequences may also be present, such as leaders for secretion, enhancers, RNA stabilizing sequences, and the like.

For diagnostic purposes, the antibodies may be used in a wide variety of formats for detecting the E2 protein, discerning HCV genotypes, detecting virions and antibodies, see for example U.S. Pat. No. 5,695,390, incorporated herein by reference. The antibodies may be used individually or in combination with other of the subject group or other antibodies or with lectins which bind to the glycosyl groups present on E2, the virion envelope proteins, or other proteins with which HCV E2 complexes, e.g., HCV E1. For diagnostic purposes, a wide variety of labels may be employed, which for the most part have been mentioned previously. These include, but are not limited to, fluorophores, chemiluminescers, radioisotopes, enzymes, particles, e.g., colloidal carbon and gold, latex particles, etc., ligands for which there are high affinity receptors, and prolabels, which can be activated to provide a detectable signal.

In one embodiment, a surface is coated with a protein which will bind to HCV antigens as free or circulating proteins or as part of an intact or partially intact virion. One may use antibodies of the subject invention which bind to both type 1 and 2 HCV, or lectins, such as Galanthus nivalis lectin. The assay involves contacting the surface with a medium, which may contain free or virion involved protein, where the medium may be the sample or a solution of known E2 of one or more genotypes. After incubation and washing to remove non-specifically bound protein, the assay may proceed in various manners depending upon what is being assayed. Where a blood sample suspected of being seropositive is being assayed, the sample is applied to the layer of E2 protein, incubated, and washed, and the presence of human antibodies bound to the protein layer determined. One may use labeled anti-(human antibodies) (other than against the isotype of the subject antibodies, where the subject antibodies have been initially used). In assays for antibodies in seropositive subjects, the subject antibodies may be used as controls with the same reagent used to detect any human anti-HCV in the sera of such subjects. The specificity of the antibodies in the sample can be confirmed by using the subject antibodies which are differentially labeled from the anti-(human antibodies) and determine whether they are blocked by the antibodies in the sample.

Where the sample is assayed for HCV E2 protein, detection employs labeled subject antibodies, the selection depending upon whether one is interested in genotyping or detection of E2 protein. After washing away non-specifically bound antibody, the presence of the labeled antibodies is determined by detecting the presence of the label in accordance with known techniques. Alternatively, where the subject antibodies are bound to the surface, a labeled lectin for E2 may be employed to detect the presence of the E2 protein.

The subject antibodies can be used to measure the reactivity of other antibodies, including antibodies in sera, monoclonal antibodies, antibodies expressed as a result of genetic engineering. Desirably, intact virions are used, rather than HCV proteins, although conformationally conserved envelope proteins may also find use. For virion capture, see, for example, Kimura et al., 1998 *J. Med. Virology* 56:25–32; Morita et al., 1996 *Hapato-Gastroenterology* 43:582–585; Sata et al., 1993 *Virology* 196:354–357; and Hijikata et al., 1993 *J. Virology* 67:1953–1958, each of which is incorporated herein by reference. One protocol is to coat a solid support with a lectin, e.g., GNA, and then contact the surface with a medium, e.g., serum of a seropositive patient, comprising intact HCV virions. Additives which might destroy the virions should be avoided, e.g., detergents. After incubating the medium and washing to remove non-specifically bound components of the medium, the virions may be contacted with the antibodies of the subject invention and the antibodies of the sample. This may be performed concurrently or consecutively, where the sample is added first. An amount of the subject antibody is used which is sensitive to displacement by another antibody. Such amount may be determined empirically, and one may wish to use different amounts of the subject antibody in a series of tests. By knowing the signal which is obtained in the absence and presence of the sample, one can determine the reactivity or binding affinity of the antibodies in the sample. Various techniques may be used to determine the amount of a subject antibody bound to the virions. Where the subject antibodies are labeled, e.g., biotin or digoxigenin, streptavidin or anti (digoxigenin) labeled with a fluorophore or enzyme whose substrate produces a detectable signal can serve to determine the amount of the subject antibodies.

Where the receptor (antibody or lectin) is labeled with a DNA sequence, either directly or indirectly (indirectly intends a ligand-nucleic acid sequence conjugate which can bind to empty sites of the receptor bound to the virion), by using primers homologous to the label sequence and standard conditions of the PCR, the sequence may be expanded. The DNA may then be detected in a separate hybridization reaction or by agarose gel electrophoresis. Alternatively, the Taqman approach may be used, using an internal labeled oligonucleotide probe homologous to the amplified sequence, having a light emitting label, fluorophore or luminescer, at one end and a quenching moiety at the other end. As the fragment is amplified, the 5'-3' exonuclease activity of the Taq polymerase degrades the hybridizing oligonucleotide freeing the fluorophore from the quencher, so that the fluorophore may now be detected by irradiation of the medium with light of an appropriate wavelength.

One may also use a labeled oligonucleotide probe appropriate for performing cycling probe technology. An oligonucleotide is constructed of about 15–20 deoxynucleotides homologous to the label and having a TM≦45° C., a sequence of about 5 or more ribonucleotides homologous to the label and having a TM≦45° C. The intact oligonucleotide will have a TM>60° C. The oligonucleotide is further modified as described above with a light emitting label and a quencher label. After adding an excess of the oligonucleotide construct to the bound label and allowing it to hybridize to the bound label at a temperature of about 55° C., RNase H, active at 55° C. is added to degrade the ribonucleotides. Upon denaturation the light emitting label will be released and free of the quencher, and upon irradiation or activation its light emission determined.

Alternatively, transcription mediated amplification (TMA) may be employed. In this case, the bound oligonucleotide label contains a promoter recognized by T7 polymerase or other convenient polymerase. Addition of T7 or other appropriate polymerase and rNTPs under appropriate conditions results in the transcription of the bound oligonucleotide to oligoribonucleotides, which can then be detected by any convenient means, e.g., electrophoresis.

Labeled subject antibodies may be used in assaying for the presence of HCV from biopsy material. Labeled antibody may be incubated with immobilized biopsy material, such as a liver slice, with a solution of one or more of the subject labeled antibodies. After washing away non-specifically bound antibodies, the presence of the antibodies bound to the cells of the biopsied tissue may be detected in accordance with the nature of the label.

Conformationally conserved E2 genotype proteins 1a, 1b, 2a, and 2b, the latter two being novel expression compositions are provided as proteins expressed from vaccinia virus constructs. Their preparation is described in the experimental section. The proteins are obtained free of amino acids of E1 proteins, although they can be prepared from genes encoding both E1 and E2, where the resulting fusion protein is processed to provide the two proteins which are no longer covalently joined, but may exist as a complex. The proteins may be isolated from a lysate or from the medium where the construct allows for secretion. The protein may be readily purified using affinity chromatography, HPLC or non-denaturing gel electrophoresis. The proteins may be obtained in purities exceeding 95 wt. %, usually at least 99 wt. %. The proteins may be used in assays for genotyping sera from HCV infected patients, in screening monoclonal antibodies for affinity and specificity, for evaluating drugs where the proteins are the target of the drugs, for immunizing mammalian hosts for the production of antisera and monoclonal antibodies, and the like. Their use in diagnostic assays has already been discussed.

The antibodies may be used to identify the structural epitopes on E2 proteins that they bind. Two basic approaches may be employed using the monoclonal antibodies for identifying conformational epitopes. In the first, natural variants or mutation analysis of HCV isolates may be used to identify regions, and ultimately individual amino acids that are involved in the epitopes recognized by the monoclonal antibodies (Schwartz et al., 1999 *J. Mol. Biol.* 287:983–999; incorporated herein by reference). The antibodies are screened against a number of different HCV E2 isolates, identifying isolates that are selectively non reactive with individual antibodies. For example, HMBAb CBH-11 reactivity with HCV E2 protein Q1a is reduced compared to its reactivity with HCV E2 Q2a (FIG. 9). "Chimeric" E2 envelope proteins are then be constructed in which portions of the chimera are derived from E2 proteins from one HCV genotype and other portions are derived from E2 proteins of another HCV genotype. These chimeric E2 proteins are constructed by PCR amplifying overlapping fragments, and/or by using restriction sites common to both E2 proteins. An alternative method is DNA shuffling as pioneered by the biotechnology company Maxy-Gen. By surveying the observed binding reactivities of different chimeric E2 proteins with different monoclonal antibodies, amino acid regions in the E2 proteins critical in forming conformational eptopes are identified. Once the critical regions are identified, individual amino acids that differ between the different genotypes are mutated to compose a reactive E2 sequence. Mutants that restore full reactivity identify amino acids that are involved in forming the epitope.

A second basic approach to defining a conformational epitope is to synthesize a series of overlapping peptides 10–15 residues in length that encode the desired sequence of HCV E2. The peptides are then screened against the antibodies using high concentrations of antibody (often 100 μg/ml or higher). Individual regions that comprise the full conformational epitope often retain residual binding activity with the antibody that can be detected. Once these regions are identified, they can be confirmed using mutational studies involving the 10–15 residues of the peptide, either in the context of the peptide or by substituting into a conformationally intact HCV E2 protein. A variation of this methodology is described in (Reineke et al., 1999 *Nature Biotechnology,* 17:271–275; incorporated herein by reference).

The subject antibodies also may be used for screening for mimotopes. Mimotopes may be prepared using phage display, and the peptides screened with the subject antibodies (Livnah et al., 1996 *Science* 273:464–471; Prezzi et al., 1996 *J. Immunol.* 156:4504–4513; each of which is incorporated herein by reference). Antibodies that recognize conformationally conserved HCV epitopes may be used as templates for the rational design of peptide or non-peptide structural mimics of the conformational epitope or mimotopes.

The generation of mimotopes is biologically significant. By mimicking the structure of the conformationally defined viral epitope, the mimotope can interfere with the ability of the virus to bind its target receptor by binding to the receptor itself. For example, analysis of a solved crystal structure defining the interface between a monoclonal antibody and tumor necrosis factor (TNF) enabled the rational design of a non-peptide mimetic capable of antagonizing the biological function of TNF by binding to the TNF receptor (Takasaki et al., 1997 *Nat. Biotech.* 15:1266–1270; incorporated herein by reference). Computational techniques that may be employed to rationally deduce protein folding from a primary amino acid sequence for use in designing a peptide structural mimetic are reviewed in Teichmann et al., 1999 *Curr. Opin. Struct. Biol.* 9:390–399; incorporated herein by reference. The practical application of computer programs for use in structurally modeling conformationally conserved epitopes is described by Schwartz et al., 1999 *J. Mol. Biol.* 287:983–999; incorporated herein by reference. An alternative method for rationally creating a peptide structural mimic of an antibody epitope involves systematic permutations of synthetic peptides designed to be a linear representation of a discontinuous antibody binding site (Reineke et al., 1999 *Nat. Biotech.* 17:271–275; incorporated herein by reference).

Peptides, or other small molecules having specific affinity for a monoclonal antibody and competitive with an epitope of a conformationally intact E2 protein, by itself or complexed with E1, may be used as vaccines, in diagnostic assays, for immunization for the production of antibodies to a specific HCV epitope, in competitive assays for defining genotype, and the like. See, for example, Puntoriero et al., 1998 *EMBO J.* 17:3521–3533; Meola et al., 1995, *J. Immunol.* 154:3162–3172; Tafi et al., 1997 *Biol. Chem.* 378: 495–502.

Another approach to effectively create structural mimetics of conformationally conserved HCV epitopes is to produce anti-idiotypic antibodies to the conformationally dependent anti-HCV HMAbs. Anti-idiotypics may effectively block the binding of native virus with its target receptor (Chanh et al., 1987 *Proc. Natl. Acad. Sci. USA* 84:3891–3895; Kopecky et al., 1999 *Intervirol.* 42:9–16; Xue et al., 1993 *J. Gen. Virol.* 74:73–79; each of which is incorporated herein by reference). Anti-idiotypic antibodies recognizing the conformational binding sites of any one of the anti-HCV HMAbs CBH-2, 5, 4B, 4D, 4G, 7, 8C, 8E, 9, or 11 could prevent viral infectivity by interfering with E2 binding to a target cellular protein, or even by interfering with virion attachment to the target cell.

The subject antibodies find use for prophylactic therapy or for treating HCV infection, by reducing viral load, by inhibiting binding of the virus to its target proteins, by inhibiting virus mediated fusion with a target cell, and by interfering with conformational changes in the viral envelope proteins necessary for cell infectivity. The composition used can be a monoclonal antibody directed to a single conformational epitope, or a mixture of complementary monoclonal antibodies that recognize distinct conformational epitopes on one or more viral envelope proteins, thereby simultaneously interfering with multiple mechanisms in the infectious process.

For reducing viral load of a body component, particularly a body component of a patient infected with HCV, patient blood is passed through a device comprising the antibodies bound to a surface for capturing the HCV. See, for example, U.S. Pat. Nos. 5,698,390 and 4,692,411; each of which is incorporated herein by reference. Various other devices found in the literature can be used with the subject antibodies to achieve a similar result. A body component can be a biological fluid, a tissue, an organ, such as the liver, and the like.

The antibodies also may be used for passive immunization therapies or other in vivo therapies. See, for example, Piazzi et al., 1997 *Arch Intern Med.* 157:1537–1544; Farci et al., 1996 *Proc. Natl. Acad. Sci. USA.* 93:15394–15399; al-Hemsi et al., 1996 *Clin. Transplant.* 10:668–675; Krawczynski et al., 1996 *J. Infect. Dis.* 173:822–828; each of which is incorporated herein by reference. For such therapeutic use, the antibodies may be formulated in any convenient way for injection or intravenous administration. Various media may be used such as phosphate buffered saline, saline, or the like. The amount of the antibodies may be varied depending on the level of infection, the affinity of the antibodies, the manner of administration, the frequency of administration, the response of the patient, the use of other therapeutics, and the like. Generally the amount of antibody administered will be in the range of about 0.1 to 5 mg/kg. See, for example, Andrus et al., 1998 *J. Infect. Dis.* 177: 889–97 and Kreil et al., 1988 *J. Virology* 72:3076–3081; each of which is incorporated herein by reference.

The chimpanzee is an accepted animal model for screening HCV vaccines and therapeutics. See, for example, Farci et al., 1996 *Proc. Natl. Acad. Sci. USA* 93:15394–15399; Farci et al., 1994 *Proc. Natl. Acad. Sci USA* 91:7792–7796; Farci et al., 1992 *Science* 258:135–140; Krawczynski et al., 1996 *J. Infect. Dis.* 173:822–828; Bassett et al., *J. Virology* 72:2589–2599; each of which is incorporated herein by reference. The effectiveness of the antibodies can be determined by monitoring for the presence and titer of HCV RNA using quantitative PCR methods. A successful reduction of viral load, or prevention of infection in a test animal or subject is reflected as a reduction or elimination of HCV RNA in serum. Enzymatic tests such as measurement of alanine aminotransferase and/or use of sequential punch needle liver biopsies also is used to test effectiveness, where improvement in the rating of either would indicate a reduction in viral-induced liver damage.

Vaccines

In formulating vaccines to HCV, any agent which mimics at least one conformational epitope of the HCV E2 protein may be used. For example, the agent may be a peptide, protein, small molecule, mimotope, organic compound, organometallic compound, or inorganic compound, etc. In a preferred embodiment, the epitopes represented in the vaccine include those against which antibodies known to prevent infection are directed. In another preferred embodiment, the epitopes represented in the vaccine include ones that are conserved among different genotypes of the virus or among different strains of the virus. In a particularly preferred embodiment of the present invention, peptides or proteins which contain the conformationally-defined epitopes of E2 of HCV are used in the formulation of a vaccine to prevent an infection by HCV or to treat an HCV infection. The peptides or proteins are preferably less than 100 amino acids in length, and more preferably less than 50 amino acids in length. In a particularly preferred embodiment, the peptides to be used in formulating a vaccine are peptide fragments of the E2 protein of HCV. Preferably the peptide folds in a manner similar to its fold in the native E2 protein thus preserving the three-dimensional structure of the conformational epitope.

The vaccine may also contain proteins that represent concatenated peptides that have the conformational epitope to which antibodies are desired. Several different peptides making up the multimer may be used so that each peptide contains a different epitope, or the same peptide may be used more than once in the multimer.

Peptides of the invention may be synthesized using any method known in the art including Merrifield solid phase chemistry. The peptides may also be obtained by cleavage of E2 protein and purification. The peptides may be made recombinantly and produced in *E. Coli*, yeast (e.g., *S. cerevisiae*), insect cells (e.g., Sf9 cells), or mammalian cells (e.g., CHO cells) using any available techniques in the art (Sambrook et al. *Molecular Cloning: A Laboratory Manual,* 2nd Ed., 1989; Miller & Calos, eds., *Gene Transfer vectors for Mammalian Cells,* 1987; Ausubel et al., eds., *Current Protocols in Molecular Biology,* 1987; each of which is incorporated herein by reference). The peptides may be modified to increase their immunogencity, solubility in aqueous solution, or to increase their propensity to fold correctly. For example, peptides may be glycosylated, farnesylated, hydroxylated, reduced, oxidized, etc.

In a particularly preferred embodiment, the peptide comprises amino acids 411 through 644 of the E2 protein of HCV genotype 1b. In another embodiment, the peptide comprises amino acids 470 through 644 of the E2 protein of HCV genotype 1b. In yet another embodiment, the peptide comprises amino acids 644 through 661 of the E2 protein of HCV genotype 1b. As would be appreciated by one of ordinary skill in this art, analogous amino acid sequences of E2 proteins from other genotypes of HCV may be used.

Analogous sequences may be determined by aligning multiple sequences of the E2 protein from different strains or genotypes of HCV. Homologous sequences which preserve the desired epitope may also be used in the formulation of vaccines. Preferably, the sequences are at least 50% homologous to the native sequence from HCV 1b E2 protein, more preferably at least 60% homologous, and most preferably at least 70% homologous.

In a particularly preferred embodiment, the peptide or collection of peptides is mixed with an adjuvant and optionally other pharmaceutically acceptable excipients before administration to an individual.

Adjuvants

Compositions utilized in the practice of the present invention may include, or may be administered as part of a protocol that includes one or more adjuvants or cytokines. Any adjuvant may be used in accordance with the present invention. A large number of adjuvant compounds is known; a useful compendium of many such compounds is prepared by the National Institutes of Health and can be found on the world wide web (http:/www.niaid.nih.gov/daids/vaccine/pdf/compendium.pdf, incorporated herein by reference; see also Allison *Dev. Biol. Stand.* 92:3–11, 1998; Unkeless et al. *Annu. Rev. Immunol.* 6:251–281, 1998; and Phillips et al. *Vaccine* 10:151–158, 1992, each of which is incorporated herein by reference). Hundreds of different adjuvants are known in the art and could be employed in the practice of the present invention.

Administration

Those of ordinary skill in the art will appreciate that antibodies or vaccines to be administered to individuals according to the present invention may be administered via any of a variety of routes, protocols, and dosing regimens. Known routes of administration include, for example, intravenous (IV), intraperitoneal (IP), intragastric (IG), subcutaneous (SQ), intramuscular (IM), oral (PO), rectal (PR), intrathecal, vaginal, intranasal, transdermal, intradermal, etc. Intravenous, intramuscular, transdermal, intradermal, intranasal, and oral deliveries are generally preferred.

Pharmaceutical Compositions

Pharmaceutical compositions for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of an agent, it is often desirable to slow the absorption of the drug from subcutaneous or intramuscular injection. This may be accomplished by the use of a liquid suspension of crystalline or amorphous material with poor water solubility. The rate of absorption of the agent then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of agent to polymer and the nature of the particular polymer employed, the rate of release of the agent can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of an inventive pharmaceutical composition include ointments, pastes, creams, lotions, gels, powders, solutions, sprays, inhalants, or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the compounds of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Treatment of Patients

The present invention also provides a method of stratifying and optionally treating patients infected with HCV. In a particularly preferred embodiment, the treatment regimen is particularly suited for an individual. A patient to be treated is provided, and a sample of serum is taken from the patient. The serum is then analyzed for the presence of particular antibodies such as neutralizing antibodies or antibodies that bind to a particular region or epitope of a protein of HCV. Any method known in the art including those described in this application may be used to determine the presence of the antibodies to be detected (e.g., ELISA, competition assay). Based on the level of antibodies in the patient's serum, a treatment can be designed for the patient. For example, a patient who does not have antibodies known to interfere with the binding of virions to their natural receptor may be treated with monoclonal antibodies of this type. In one particularly preferred embodiment, the sera from the HCV-infected patient is considered positive for the presence of a competing antibody if 50% or greater inhibition of E2 binding was obtained at a dilution of 1/200 or greater of the patient's serum, more preferably of 1/500 or greater, and most preferably of 1/1000 or greater.

One of the advantages of this method is that the treatment is tailored to the particular individual being treated. Only those antibodies that are needed and not produced naturally by the patient are administered. This avoids or reduces the risk of adverse reactions from administering therapeutics that are not needed. This method would also eliminate the expense of treating patients who would not benefit from such treatment. For example, if a patient were already producing an antibody to a particular epitope of E2, there would be no need to administer a human monoclonal antibody directed against the epitope exogenously.

In another particularly preferred embodiment, the treatment may include administering a vaccine designed to induce the production of antibodies that have been found to be lacking in the patient. In a particularly preferred embodiment, the vaccine contains an epiptope or mimotope thereof, to which antibodies are not being produced naturally in the individual. The administration of such a vaccine would induce the patient's immune system to start producing a set of antibodies directed against the administered epitope.

EXAMPLES

Example 1

Production of HCV E2 Proteins from Multiple Genotypes in Vaccinia Virus

To analyze the reactivity of HCV sera and test the breadth of HCV-HMAbs reactivity, the complete coding sequence of HCV were cloned from isolates of HCV genotypes 1a, 1b, 2a, and 2b, were PCR amplified from HCV positive sera and expressed with vaccinia virus using the pVOTE (Ward et al., 1995 *Proc. Natl. Acad. Sci. USA* 92:6773–6777; incorporated herein by reference) transfer vector (constructs Q1a, Q1b, Q2a, and Q2b for HCV genotypes 1a, 1b, 2a, and 2b, respectively). Genotype selection was based on its divergence and frequency among HCV infected individuals in the United States (Mahaney et al., 1994 *Hepatology* 20:1405–1411; incorporated herein by reference). Oligonucleotide primers were designed to amplify fragments that expressed the final 39 amino acids of E1, all of E2/p7, and the N-terminal 98 amino acids of NS2. See Table 2. SEQ ID NOS: 18–27).

Accordingly, aliquots of plasma from individuals PCR positive for HCV RNA were obtained and genotyped using the InnoLipa HCV genotyping assay performed according to manufacturer's instructions (Innogenetics, Ghent, Belgium). RNA was prepared from 125 µl of plasma from individuals infected with HCV genotypes 1a, 1b, 2a, and 2b using the Puerescript RNA kit, according to manufacturer's instructions (Gentra Systems, Minneapolis, Minn.). RNA pellets were re-suspended in 25 µl of RNAse free $H_2O$ and 10 µl was subjected to reverse transcriptase PCR. Reverse transcription reactions were performed using MMLV reverse transcriptase employing the reverse HCV specific primer HCV E2-R1 5'-CGC GCA CrA AGT AsG GyA CT-3' (SEQ ID NO: 16). Reverse transcription was for 60 minutes at 40° C. Reverse transcribed cDNA was denatured by a 5 minute incubation at 98° C. followed by cooling to 4° C. and the addition of PCR mix containing 0.15 mM dNTPs, 3 µl 10× PCR buffer, 3 units of Amplitaq polymerase, and the forward primer HCV E2-F1 5'-CGC ATG GCi TGG GAy ATG ATG-3' (SEQ ID NO: 17). Amplification was for 30 cycles of 94° C. for 1 minute, 55° C. for 3 minutes, and 72° C. for 3 minutes. Between to and 8 µl of amplified product was then subjected to a second round of PCR amplification with using the forward primer appropriate for cloning each genotype and an internal reverse primer INT-Reverse (Table 2, SEQ ID NOS: 18–27) or the reverse primer appropriate for each genotype and INT-Forward. PCR amplifications were for 30 cycles of 94° C. for 1 minute, 60° C. for 2.5 minutes, and 72° C. for 2 minutes. Appropriately sized bands (~820 nucleotides for the genotype specific forward primer and INT-Reverse and ~1080 nucleotides for INT forward and the genotype specific reverse primer) and were excised from ethidium-bromide stained agarose gels and purified using a commercially available resin (Qiagen, Valencia, Calif.). Approximately 50 ng of each band were combined and re-amplified with the forward and reverse primers appropriate for each genotype (Table 2). PCR amplifications were for 30 cycles of 94° C. for 1 minute, 55° C. for 2.5 minutes, and 72° C. for 2 minutes. The amplified products were then excised from ethidium bromide stained agarose gels, purified, and digested with the appropriate restriction enzymes. This 3 step amplification procedure resulted in a much higher yield of full-length insert than standard two-step procedures. The digested DNAs were then ligated into a similarly digested pVOTE 1 or pVOTE 2 vector (Ward et al., 1995 *Proc. Natl. Acad. Sci. USA* 92:6773–6777; incorporated herein by reference). The ligated plasmids were transfected into competent *E. coli* and insert-containing clones were identified and propagated using standard methods (Sambrook J., Fritsch E. and Maniatis T. *Molecular Cloning: A Laboratory Manual. Cold Spring Harbor Press*, Cold Spring Harbor, N.Y., 1989; incorporated herein by reference). The clones obtained were designated Q1a, Q1b, Q2a, and Q2b for constructs expressing full length E2 and p7 of HCV genotypes 1a, 1b, 2a and 2b, respectively.

TABLE 2

Primers* employed in cloning HCV E2 protein

| Gtyp | Forward Primer | SEQ ID NO. |
|---|---|---|
| 1a | CG AGG CIT <u>CAT ATG</u> ATC GCT GGT GCT TGG<br>Nde I | 18 |
| 1b | CG CAT ATG <u>GAG CTC</u> GCG GGG GCC CAC TGG GGA GT<br>Sac I | 20 |
| 2a | C GCT CGA <u>GCC ATG G</u>TT GGC GGG GCT CAT TGG GGC<br>Nco I | 22 |
| 2b | C GCT CGA <u>GCC ATG G</u>TT TTC GGC GGC CAT TGG GTG<br>Nco I | 24 |
| INT | TG GTT CGG BTG YWC ITG GAT GAA | 26 |

| Gtyp | Reverse Primer | SEQ ID NO. |
|---|---|---|
| 1a | CG GAA TCC <u>CTG CAG</u> CTA CAA ACT GGC TTG AAG AAT CCA<br>Pst I | 19 |

TABLE 2-continued

Primers* employed in cloning HCV E2 protein

| | | |
|---|---|---|
| 1b | GC TCT AGA <u>CTG CAG</u> CTA TAT GCC AGC CTG GAG CAC CAT<br>  Pst I | 21 |
| 2a | TC GAA TTC <u>GGA TCC</u> TAC AAA GCA CCT TTT AGG AGA TAA GC<br>  BamH I | 23 |
| 2b | TC GAA TTC <u>GGA TCC</u> TAC AGA GAC GCT TTA AGG AGG TAG GC<br>  BamH I | 25 |
| INT | TAA TGC CAi ARC CKR TAi GGG TAG TC | 27 |

*Inner nested primers employed in cloning of vaccinia virus E2 constructs. The restriction sites employed in the cloning are underlined. The primers contained additional restriction sites in their 5' ends. The primers contain other restriction sites. Gtyp = HCV genotype. The primers INT-F and INT-R contain degenerate nucleotides and were used for all genotypes. PCR amplification conditions are described in Example 1.

Expression of intact E2 protein by vaccinia virus constructs Q1a and Q2b was verified in a transient expression assay. CV-1 cells were infected with 5 plaque forming units (pfu) of wild type vaccinia virus strain VWA (Ward et al. supra) and then transfected with pVOTE plasmid using Transfectam (Promega, Madison, Wis.), according to the manufacturer's instructions. Cells were cultured in media supplemented with 1 mM Isopropyl-B-D-thiogalactopyranoside (IPTG) to induce expression of HCV proteins (Ward et al. supra). Forty eight hours after transfection the cells were harvested by washing cultured cells with PBS and resuspending the cells in lysis buffer (150 mM NaCl, 20 mM Tris (pH 7.5), 0.5% deoxycholate, 1.0% Nonidet-P40, 1 mM EDTA) to which the protease inhibitors Pefbloc (Boehringer Mannheim, Indianapolis, Ind.), Aprotinin, Leupeptin, and Pepstatin were added to final concentrations of 0.5 mg/ml, 2 µg/ml, 2 µg/ml, and 1 µg/ml, respectively. One hundred microliters of lysis buffer was added for every 3×10$^6$ cells harvested. Nuclei were the pelleted by centrifugation at 18,000×g at 4° C. for 10 minutes and the supernatant was either used directly or stored at 4° C. for not more than two days prior to use.

For Western blot analysis, 10 µl of lysis buffer extract was combined with 10 µl of 2× SDS sample buffer (20% glycerol, 10% β-mercaptoethanol, 4.8% SDS, 0.125 mM Tris (pH 6.8), heated to 95° C. for 5 minutes, and fractionated by sodium dodecyl sulfate-polyacrylamide gel electrophoresis (SDS-PAGE) (Laemmli et al., 1970 *Nature* 227:680–685; incorporated herein by reference) employing 12% polyacrylamide gels. The fractionated proteins were then electrotransferred to nitrocellulose and incubated overnight with murine monoclonal antibody (mMab) 2C8 that recognizes Western blotted HCV E2 (available from Dr. H. Greenberg, Stanford University). mMAb 2C8 was diluted 1:500 in BLOTTO (2.5% non fat dry milk, 2.5% normal goat serum, 0.1% Tween-20 (Sigma, St. Louis, Mo.), 0.02% sodium azide in TBS: 150 mM NaCl, 20 mM Tris, pH 7.5). Purified HCV or control antibodies or HMAb-containing culture media diluted to an IgG concentration of 5 µl/ml in BLOTTO. The blots were washed 3 times with TBS, and bound antibody was detected with the ECL Western blot kit, according to manufacturer's instructions (Amersham, Arlington Heights, Ill.).

The constructs Q1a and Q2b produced an approximately 70 kdal protein that was immunoreactive with mMAb 2C8 (FIG. 1). As expected with the pVOTE system (Ward et al., 1995 *Proc. Natl. Acad. Sci. USA* 92:6773–6777; incorporated herein by reference) the expression of the HCV E2 proteins was highly dependent on the presence of the inducer IPTG. Expressed protein was also detected from all 4 constructs by IFA with a panel of 10 genotyped HCV sera (data not shown). None of the constructs were reactive with HCV-negative sera nor did any of the HCV antisera react with cells infected with wild type vaccinia virus.

The genotypes of the cloned E2 proteins were confirmed by DNA sequencing of either a 160 bp internal fragment (nts. 2009 to 2168 of HCV-1) from the center of HCV E2 from each of the four clones. See FIG. 2 (SEQ ID NOS: 9–12), or the entire insert (construct Q1b) employing dye terminator methodologies and an automated DNA sequencer (Applied Biosystems, Foster City Calif.). The inserts were highly homologous to the appropriate sequences of HCV E2 available in various databases with no frame shift or termination mutations. See FIG. 3 (SEQ ID NOS: 1–8). Thus, this is good evidence that HCV E2 of all 4 genotypes was accurately expressed by the pVOTE constructs. Plasmids that produced intact HCV were then used to generate recombinant vaccinia virus by homologous recombination into the hemaglutinin locus of the vaccinia virus strain VWA (Ward et al., supra as described Moss and Earl, In F. Ausubel and R Brent and R Kingston (ed.), *Current Protocols in Molecular Biology*, Vol. 2, John Wiley & Sons, New York, N.Y., 1994; each of which is incorporated herein by reference). Recombinant vaccinia viruses were identified via infection of BSC-1 cells followed by selection for guanine phosphoribosyl transferase containing virus with media containing mycophenolic acid, xanthine, and hypoxanthine, using standard methods (Moss et al., supra). Purified viral stock was obtained for each recombinant virus and titers measured using BSC-1 cells ranged between 5–10×10$^8$ pfu/ml.

Example 2

Antibody Screening of Potential HCV Positive B-Cell Donors

Since HCV cannot be reliably propagated in vitro, it is necessary to use recombinant envelope proteins expressed in eukaryotic cells to identify individuals with strong titers to HCV proteins. In such screening it is necessary to use methods that preserve the native structure of the envelope proteins thus allowing the detection of antibodies to conformational epitopes. In the identification of sera for the generation of HCV HMAbs an indirect immunofluorescent assay (IFA) was employed. This assay uses acetone-fixed cells and is analogous to methods used in the production of neutralizing HMAbs to conformational epitopes on human T-lymphotropic virus envelope protein (Hadlock et al., 1997 *J. Virology* 71:5828–5840; incorporated herein by reference). For HCV, acetone-fixed cells expressing HCV E2 envelope proteins were used. At various points the E2 proteins were expressed using recombinant baculovirus in Sf9 cells, recombinant vaccinia virus in HeLa cells, as described above, or in Chinese hamster ovary (CHO) cells using a commercially available vector (pDisplay, In Vitrogen, Carlsbad, Calif.). Since insect derived cells may not express viral envelope proteins in a truly native conformation (Rosa et al. supra; Arp et al., 1996 *J. Virology*, 70:7349–7359; each of which is incorporated herein by reference) the use of vaccinia virus or mammalian cell expression systems is preferred. The fluorescence observed with a given serum was scored visually via fluorescence microscopy, and in some cases increasing dilutions of the sera were evaluated to obtain an end point dilution titer of the potential donor sera.

To confirm results obtained with immunofluorescence a microtiter plate assay for evaluating the reactivity of sera to HCV E2 was developed. Monolayers of HeLa cells were grown to 80% confluence and infected with 5 pfu/cell of VWA and 5 pfu/cell of recombinant vaccinia virus or 5 pfu of VWA only. HCV recombinant viruses were mixed with wild type vaccinia with an intact hemaglutinin gene to minimize the vaccinia virus induced cytopathic effect observed with hemaglutinin minus virus (Seki et al., 1990 *Virology* 175:372–384; incorporated herein by reference). Twenty-four hours after infection cells were harvested. Extracts were prepared by washing the cells with PBS and then resuspending $30 \times 10^6$ cells in 1 ml of lysis buffer (150 mM NaCl, 20 mM Tris (pH 7.5), 0.5% deoxycholate, 1.0% Nonidete-P40, 1 mM EDTA, 0.5 mg/ml Pefablock (Boehringer Mannheim, Indianapolis, Ind.), 2 µg/ml Aprotinin, 2 µg/ml Leupeptin, and 1 µg/ml Pepstatin). Nuclei were pelleted by centrifugation at 18,000×g at 4° C. for 10 minutes. Extracts were stored at 4° C. and used for ELISA within 24 hours of preparation. Microtiter plates (Maxisorp, Nalge Nunc International, Rochester, N.Y.) were prepared by coating individual wells with 500 ng of purified *Galanthus nivalis*, lectin (obtained from SIGMA, St. Louis, Mo.) in 100 µl of PBS for 1 hour at 37° C. Wells were then washed with TBS (150 mM NAC1, 20 mM Tris-HCL, pH 7.5), and blocked by incubation for 1 hour at room temperature with 150 µL BLOTTO (TBS plus 0.1% Tween-20, 2.5% normal goat sera, 2.5% non fat dry milk). Plates were washed two times with TBS followed by the addition of 20 µl of extract from vaccinia virus infected HeLa cells 1:5 with BLOTTO. After incubation for 1.5 hours at room temperature, plates were washed three times with TBS followed by addition of HCV sera at various dilutions in 95 µl of BLOTTO supplemented with 5 µL of soluble extract from HeLa cells infected with vaccinia virus VWA. The inclusion of the soluble extract served to suppress reactivity to vaccinia virus proteins that might also be captured by GNA lectin. Plates were incubated for 1.5 hours, wells were washed three times with TBS and 100 µl of anti-human alkaline-phosphatase conjugate (Promega, Madison, Wis.) diluted 1/5000 in BLOTTO was added. After incubation for 1 hour at RT, the plates were then washed four times with TBS followed by incubation with a 1 mg/ml solution of p-nitrophenyl phosphate (PNPP). Substrate development was allowed to proceed for 30 to 45 minutes, then the absorbance of the wells at 405 nm was determined using a multiwell plate reader (Du Pont Co., Wilmington, Del.).

Figure 4A:
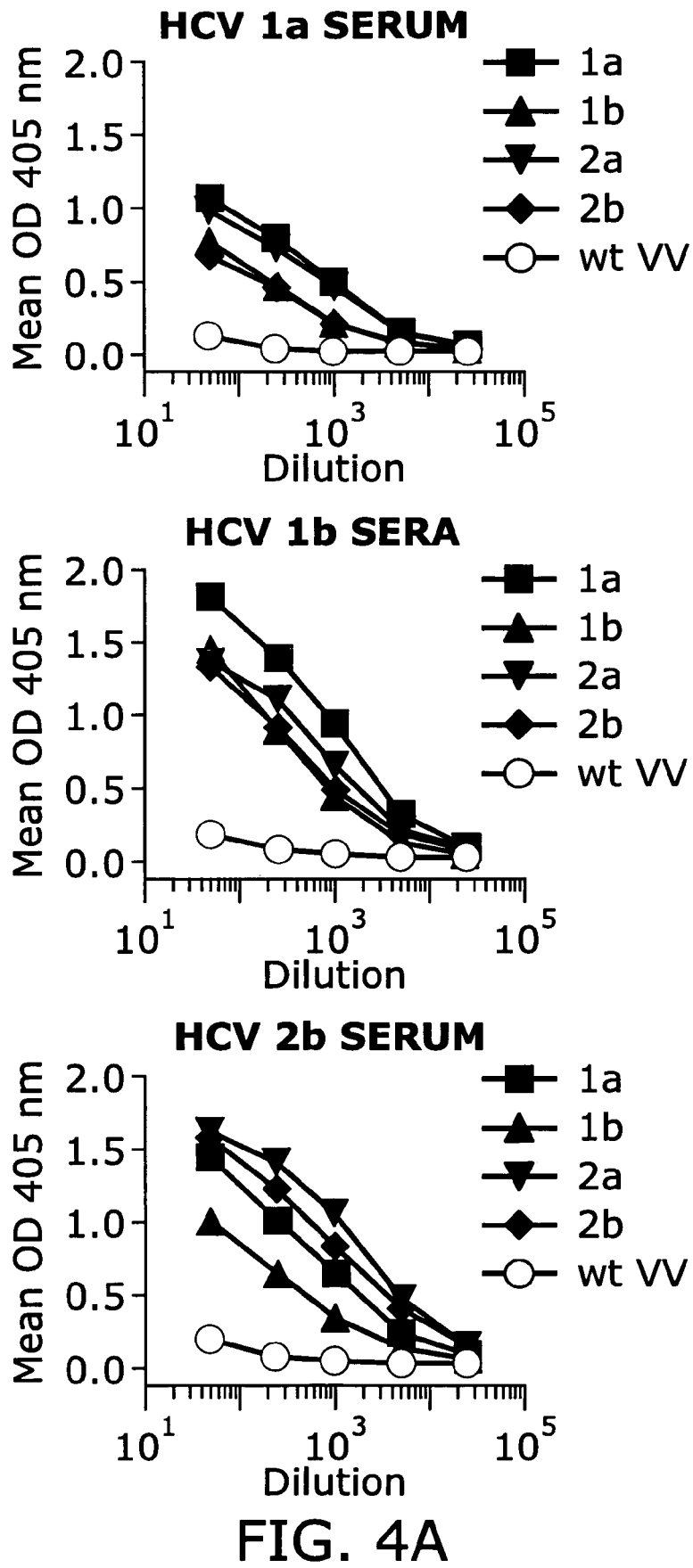
Figure 4B:
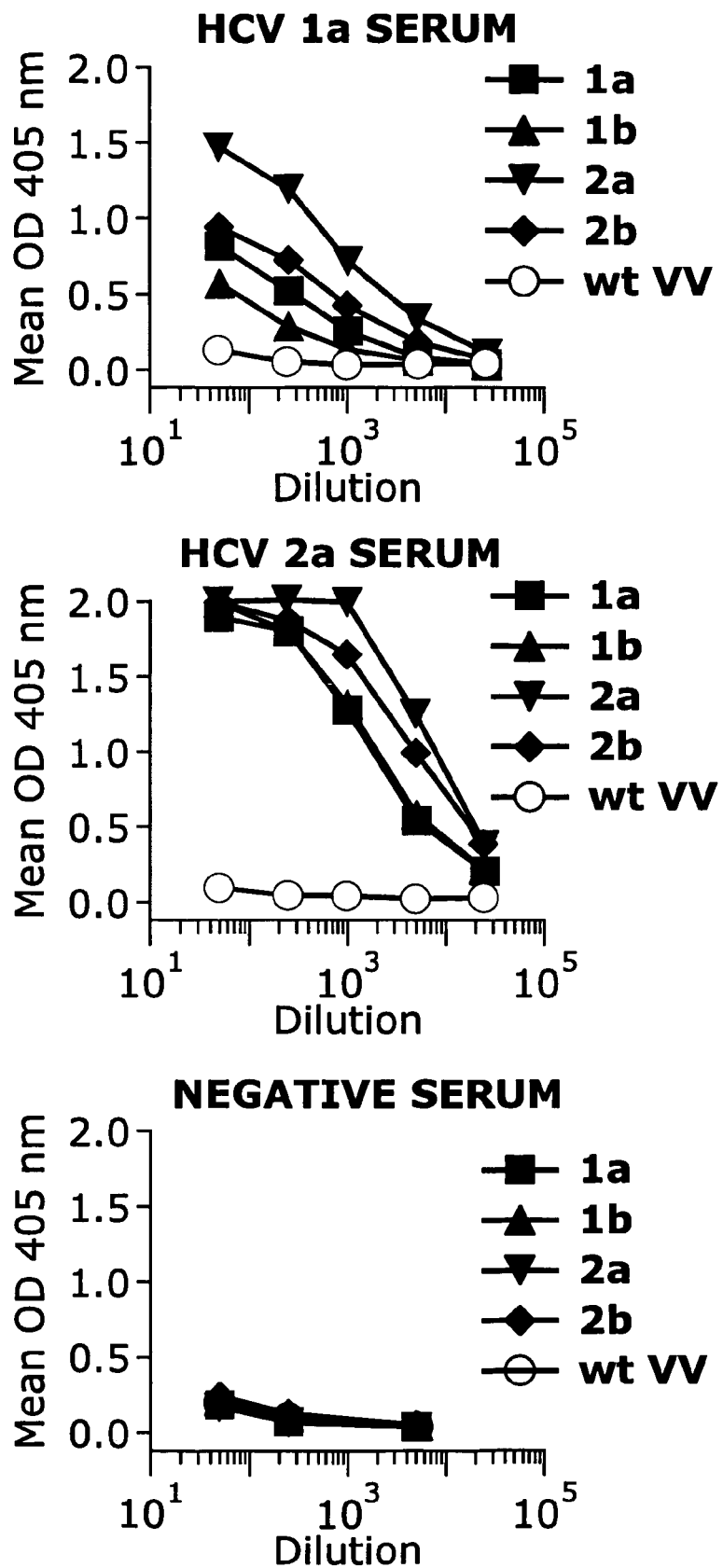

Typical results are presented in FIG. 4. In this experiment five genotyped HCV sera and one serum from an HCV negative blood donor were titrated against HCV E2 proteins of genotypes 1a, 1b, 2a, and 2b, as well as proteins captured from extracts infected with non-recombinant vaccinia virus VWA. Minimal reactivity to the HCV E2 was observed with a serum from an uninfected individual (Graph labeled Negative Serum). Additionally all five sera from HCV infected individuals exhibited little or no reactivity to proteins captured from extracts infected with wild type vaccinia virus (thin black lines, all graphs). It can be appreciated that a wide variation in seroreactivity to HCV E2 proteins was obtained with the five sera tested, with the HCV 2a individual exhibiting the highest overall reactivity.

Figure 5:
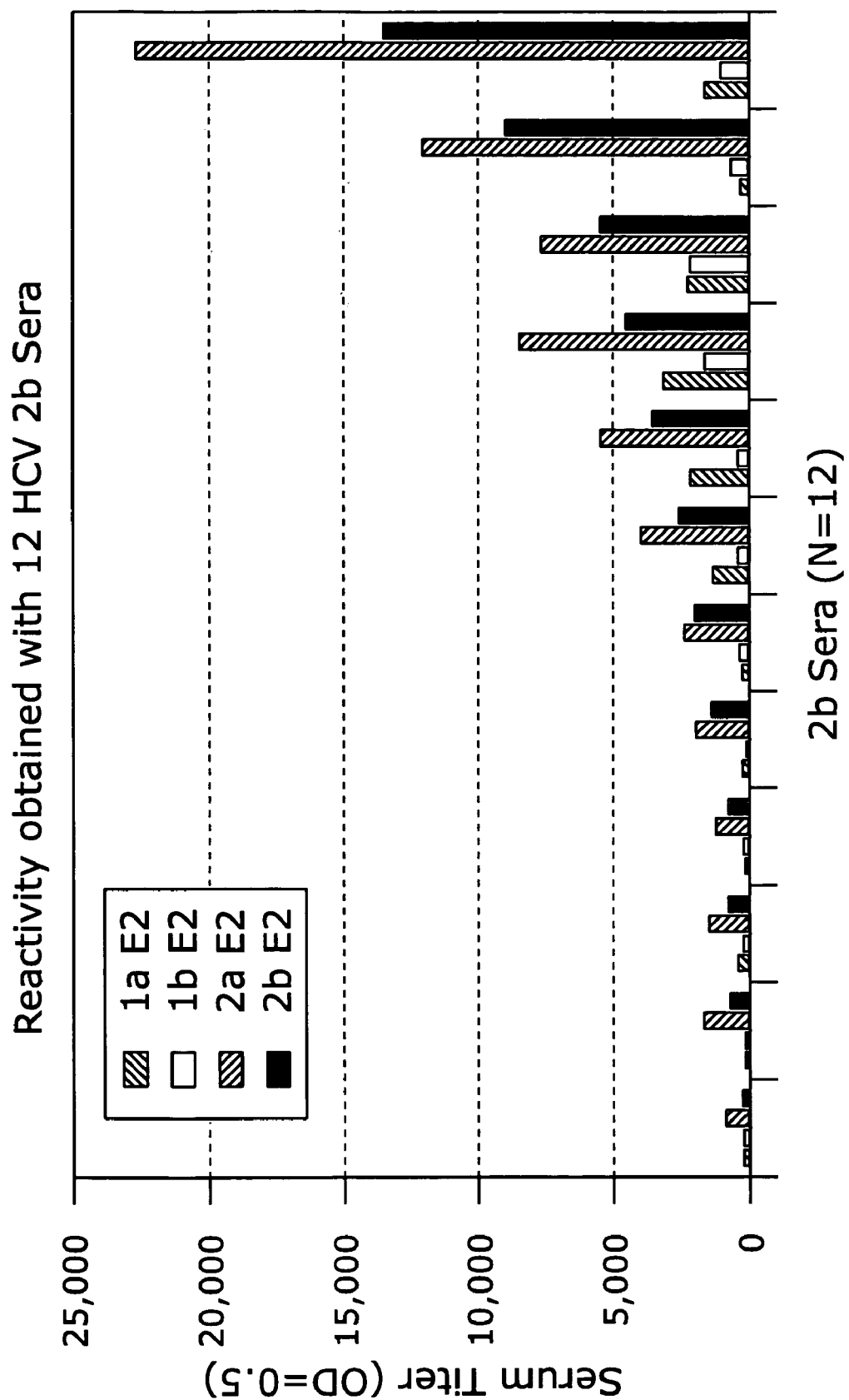

The results obtained with 12 sera from individuals infected with HCV genotype 2b are presented in FIG. 5. In this graph the dilution of sera that resulted in a specific OD of 0.5 for all four of the HCV E2 proteins is compared (Specific OD is the OD obtained from wells coated with extract of HCV E2 construct—OD of wells coated with extract of non-recombinant vaccinia virus). For all 12 sera, reactivity to HCV 2b or 2a E2 protein was significantly greater than that obtained with HCV 1a or 1b E2 protein. This indicates the superiority of HCV genotype 2 E2 proteins for the detection of antibodies recognizing the HCV envelope in individuals infected with HCV genotype 2a or 2b. Also, the individuals presented on the right side of the graph would be more promising donors for the isolation of HCV HMAbs specific for epitopes present in genotype 2a or 2b E2 proteins.

The donor employed to generate the HCV HMAbs was identified as HCV seropositive with the first generation HCV screening assay during a course of autologous donation. Alanine aminotransferase (ALT) testing of the donated units resulted in 6 out of 7 of the donations being within the normal range (<45 IU). One donation had an ALT value of 49, which is just over the normal cutoff. Otherwise the donor exhibited no outward symptoms of hepatitis. This individual was later confirmed to be HCV positive by PCR using the Roche amplicor HCV assay (Roche Diagnostics, Branchburg, N.J.) and was determined to be infected with HCV of the 1b genotype by the InnoLipa probe assay (Innogentics, Ghent, Belgium). This individual was found to have a high titer of antibodies capable of recognizing HCV E2 using IFA. Testing with the neutralization of binding assay (see below) also indicated this donor had a high titer of potentially neutralizing antibodies. Peripheral blood B-cells were isolated from this individual and successfully used to generate HCV antibody secreting human hybridomas (described below).

Example 3

Production of Antigen-Specific Human Monoclonal Antibodies

Peripheral B-cells were purified from donor T-cells by T-cell rosetting as described (Foung et al., 1984 *J. Immunol. Methods* 134:35–42; incorporated herein by reference) which disclosure is incorporated by reference. Individual cultures of $1 \times 10^4$ B-cells were EBV-activated in microtiter plates. HCV specific antibodies were detected with an immunofluorescence assay (IFA). Cells infected with recombinant vaccinia virus expressing HCV E2 proteins, recombinant baculovirus expressing HCV E2, and/or mammalian cell lines that have been engineered to express HCV E2 from their DNA were fixed onto HTC supercured 24-spot slides. The cells were fixed with 100% acetone for 10 minutes at room temperature. Fixed cells were incubated with undiluted culture media from EBV activated B cells or hybridomas for 30 minutes at 37° C. and washed for 5 minutes with phosphate buffered saline (PBS), pH 7.4. Slides were then incubated for 30 minutes at 37° C. with 0.001% solution of Evan's blue counterstain and fluorescein isothiocyanate (FITC) conjugated goat-anti-human IgG (Zymed, South San Francisco, Calif.). Bound antibody was revealed by fluorescence microscopy.

Out of 540 cultures, 99 wells showing significant immunofluorescence to HCV E2 were identified (yield ~18%) and 30 of the EBV-activated cultures with different immunofluorescence patterns were selected for electrofusion to mouse-human heteromyelomas as described (Found et al., 1990 *J. Immunol. Methods* 134:35–42; Zimmerman, et al., 1990 *J. Immunol. Methods* 134:43–50; Perkins et al., 1991 *Hum. Antibod. Hybridomas* 2:155–159; each of which is incorporated herein by reference). Out of 12 fusions (some fusions contained more than one positive EBV activated culture), 182 out of 456 initial hybridoma cultures exhibited reactivity with HCV E2 by IFA (yield 40% overall). Six additional fusions were performed on two of the original EBV-activated cultures that showed reactivity to HCV-E2 by Western blot. Hybridomas secreting HCV E2 antibodies reactive by Western blot (in addition to being IFA reactive) were isolated from two of the fusions. Overall, 30 human hybridomas were frozen. Limiting dilution clones were isolated from 12 parent hybridomas and HCV-HMAbs from 11 of the hybridomas were produced in bulk for subsequent studies. eight of the HCV HMAbs were $IgG_1$ with kappa light chains and two were $IgG_1$ with lambda light chains. HMAb CBH-9 was $IgG_1$ but it is not known whether it uses a lambda or kappa light chain. PCR and DNA sequence analysis of 10 of the HMAbs (the lone exception was HMAb CBH-9) confirmed that all of the HMAbs expressed distinct heavy and light chains. The fusion partners, IgG subtypes, and results obtained in IFA with the hybridomas are described in Table 3.

Example 4

HCV E2 ELISA

Figure 6:
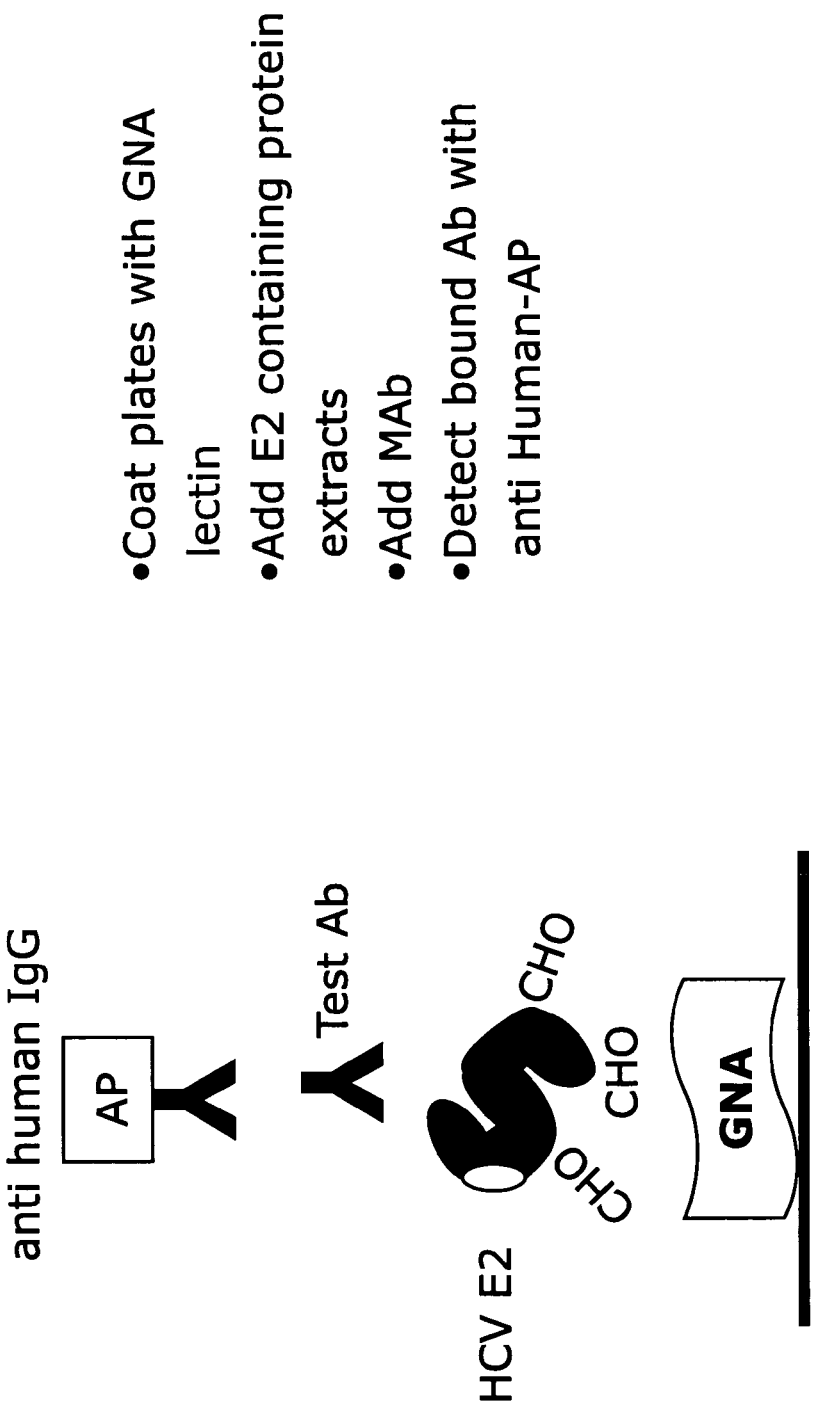

Previous studies indicated that the HCV E2 protein is highly glycosylated and can be bound by any one of several lectins including *Galanthus nivalis* (GNA), *Tiriticum vulgaris* (WGA), and *Ricinus communis* (Ralston et al, 1993, supra; da Silva Cardosa, 1998, supra; Sato et al., 1993 *Virology* 196:354–357; each of which is incorporate herein by reference). Therefore, the utility of the two lectins GNA and WGA as reagents was evaluated for capturing HCV E2 protein onto a microtiter plate. A schematic of this assay is depicted in FIG. 6.

Monolayers of HeLa cells were grown to 80% confluence and infected with 5 pfu/cell of VWA and 5 pfu/cell of recombinant vaccinia virus or 5 pfu of VWA only. HCV recombinant viruses were mixed with wild type vaccinia with an intact hemaglutinin gene to minimize the vaccinia virus induced cytopathic effect observed with hemaglutinin minus virus (Seki et al. 1990, *Virology* 175:372–384; incorporated herein by reference). Twenty-four hours after infection cells were harvested. Extracts were prepared by washing the cells with PBS and then resuspending $30 \times 10^6$ cells in 1 ml of lysis buffer (150 mM NaCl, 20 mM Tris pH 7.5, 0.5% deoxycholate, 1.0% Nonidet-P40, 1 mM EDTA, 0.5 mg/ml Pefabloc (Boehringer Mannheim, Indianapolis, Ind.), 2 µg/ml Aprotinin, 2 µg/ml Leupeptin, and 1 µg/ml Pepstatin). Nuclei were pelleted by centrifugation at 18,000×g at 4° C. for 10 minutes. Extracts were stored at 4° C. and used for ELISA within 24 hours of preparation.

TABLE 3

Characteristics and IFA reactivity of HCV HMAbs

| Antibody[a] | Hetero Myeloma | Subtype Heavy | Subtype Light | Immunofluorescence 1a | 1b | 2a | 2b |
|---|---|---|---|---|---|---|---|
| CBH-2 | $K_6H_6/B_5$ | IgG1 | Kappa | ++ | ++ | ++ | ++ |
| CBH-4D | $K_6H_6/B_5$ | IgG1 | Lambda | + | + | – | – |
| CBH-4B | $K_6H_6/B_5$ | IgG1 | Kappa | ++ | ++ | +/– | – |
| CBH-4G | $K_6H_6/B_5$ | IgG1 | Kappa | + | + | +/– | +/– |
| CBH-5 | H73C11 | IgG1 | Kappa | ++ | ++ | ++ | ++ |
| CBH-7 | $K_6H_6/B_5$ | IgG1 | Kappa | ++ | ++ | ++ | ++ |
| CBH-8C | $K_6H_6/B_5$ | IgG1 | Kappa | ++ | ++ | ++ | ++ |
| CBH-8E | $K_6H_6/B_5$ | IgG1 | Kappa | ++ | ++ | ++ | ++ |
| CBH-9 | H73C11 | IgG1 | Unknown | + | + | +/– | +/– |
| CBH-11 | $K_6H_6/B_5$ | IgG1 | Kappa | + | ++ | ++ | ++ |
| CBH-17 | $K_6H_6/B_5$ | IgG1 | Lambda | + | ++ | – | – |
| R04 | | IgG1 | Lambda | – | – | – | – |

[a]Reactivity by IFA of HCV HMAbs with HeLa cells infected with recombinant vaccinia virus expressing HCV E2 of the indicated genotype. Reactivity was scored ++ strongly positive; + positive; +/– weakly positive; – negative. The heavy and light chain subtypes of the antibodies are provided. R04 is an isotype matched control antibody. Antibodies were tested at 10 µg/ml.

Microtiter plates (Maxisorp, Nalge Nunc International, Rochester, N.Y.) were prepared by coating individual wells with 500 ng of purified lectin in 100 µl of PBS for 1 hour at 37° C. Wells were then washed with TBS (150 mM NAC1, 20 mM Tris-HCL, pH 7.5), and blocked by incubation for 1 hour at room temperature with 150 µL BLOTTO (TBS plus 0.1% Tween-20, 2.5% normal goat sera, 2.5% non fat dry milk). Plates were washed two times with TBS followed by the addition of 20 µl of extract from vaccinia virus infected HeLa cells 1:5 with BLOTTO. After incubation for 1.5 hours at room temperature, plates were washed three times within TBS followed by addition of unlabeled antibodies at various concentrations in 100 µl of BLOTTO. Plates were incubated for 1.5 hours, wells were washed three times with TBS and 100 µl of anti-human alkaline phosphatase conjugate (Promega, Madison, Wis.) diluted 1/5000 in BLOTTO was added. After incubation for 1 hour at RT, the plates were then washed four times with TBS followed by incubation with a 1 mg/ml solution of p-nitrophenyl phosphate (PNPP). Substrate development was allowed to proceed for 30 to 45 minutes, then the absorbance of the wells at 405 nm was determined using a multiwell plate reader (Du Pont Co., Wilmington, Del.).

Figure 7:
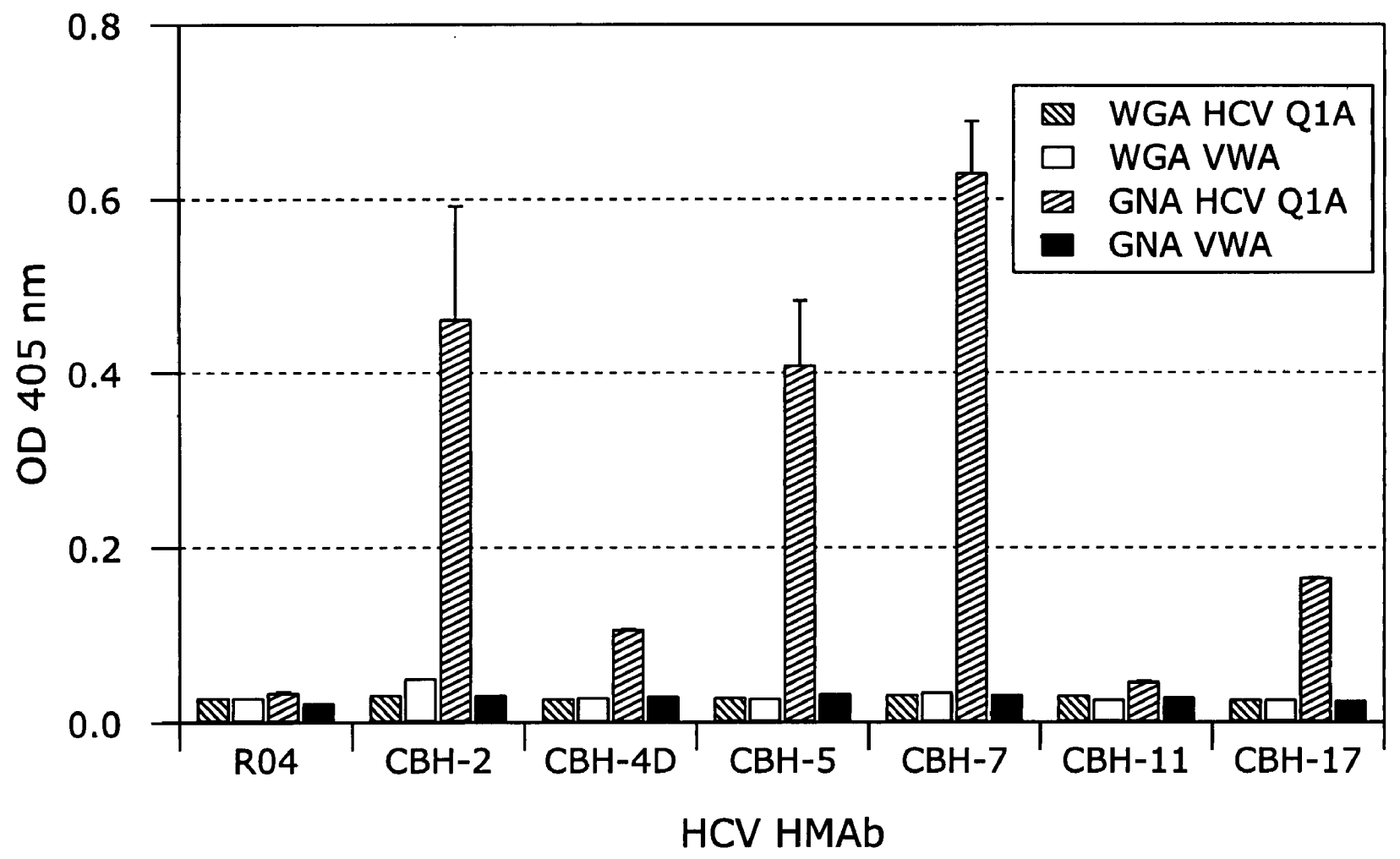

HCV1a E2 produced by recombinant Q1a vaccinia virus was employed as a source of HCV E2 and six HCV HMAbs were employed as detection reagents (FIG. 7). No reactivity was observed to proteins captured with either lectin with a control monoclonal and only background levels of reactivity were observed for all HCV HMAbs with proteins captured by WGA. In contrast, HCV HMAbs CBH-2, CBH-5, CBH-7 all exhibited strong reactivity to proteins captured by GNA. Additionally HCV HMAbs CBH-17 and CBH-4D had lower levels of reactivity with GNA captured proteins. This suggests that HCV HMAb CBH-11 does not recognize this particular E2. However it is clear that the GNA capture ELISA is extremely useful for analyzing the reactivity of HMAbs with HCV E2.

Therefore the reactivity of the HCV HMAbs was then evaluated with recombinant vaccinia virus expressing E2 proteins of divergent genotypes (FIG. 8). All 11 HCV HMabs bound to two or more of the HCV E2 constructs and no specific signal was obtained with a control HMAb (Panel marked R04). The HMAbs with the highest relative affinity and levels of reactivity to E2 proteins of all four genotypes were CBH-7 and CBH-8C followed by HMAbs CBH-5, -2, and -8E. HMAbs CBH-4G and CBH-9 exhibited significantly greater reactivity to HCV E2 proteins of genotypes 2a and 2b, while HMAb CBH-11 was markedly less reactive with Q1a E2 protein. HMAb CBH-17, and to a lesser extent CBH-4D and CBH-4B, exhibited preferential binding to E2 proteins of genotype 1a and 1b relative to E2 proteins of genotypes 2a or 2b. These variations were not a result of varying efficiencies of capture of the different E2 proteins since the maximum signals obtained with the different E2 proteins since the maximum signals obtained with the different E2 proteins were very comparable in all experiments. These results were consistent with the results obtained in IFA with the same constructs (See Table 3, above). Seven antibodies, CBH-2, -4G, -5, -7, -8C, -8E, and -9, exhibited significant reactivity with all tested HCV E2 constructs and can be considered broadly reactive.

The reactivity of all tested HMAbs with at least two HCV genotypes suggested that the epitopes recognized by the HCV HMAbs would be highly conserved (See FIG. 9). It was of interest to determine whether the epitopes recognized by the HMAbs would be conformational or linear in nature. This was addressed directly by comparing the reactivity of the HCV HMAbs to both native and denatured HCV E2 proteins (See FIG. 9). As expected all 11 HCV HMAbs recognize HCV 1b E2. Treatment of HCV E2 by heating to 56° C. in the presence of 0.5% SDS and 5 mM dithiothreitol results in complete abrogation of reactivity for 10 of the 11 HCV HMAbs. The sole exception is HMAb CBH-17, which retains approximately 90% of its reactivity with the denatured E2 protein. Western Blot analysis of the HMAb CBH-17 confirmed it was weakly reactive with HCV envelope proteins expressed by vQ1a, or vQ1b (data not shown). No reactivity with Western blotted vQ1a was observed with any of the remaining 10 HMAbs (data not shown). Thus 10 of the 11 HCV HMAbs recognize conformational epitopes.

Lastly, competition analyses were employed to define which HCV HMAbs recognize the same (or very spatially close) epitopes. A schematic of this assay is depicted in FIG. 10. The HCV HMAbs CBH-5, CBH-2, and CBH-7 were biotinylated using standard methods and the reactivity of the biotinylated HMAbs to HCV type 1 or type 2 E2 in the presence of an excess of selected HMAbs was compared to those seen in samples without any added antibody. As seen in FIG. 11, the control HMAb R04 and the HCV HMAbs CBH-4D, -4B, -4G, -7, -9, and -17 all exhibited essentially no inhibition of HMAb CBH-5 binding. In contrast HMAb CBH-5 was inhibited 85% by an excess of itself and approximately 75% by HMAb CBH-8E. HMAb CBH-5 was inhibited more variably by HMAbs CBH-8C and CBH-11 and only inhibited to approximately 50% by HMAb CBH-2. In particular, the competition seen with HMAb CBH-2 is relatively equivocal, and it is not clear whether CBH-2 recognizes the same epitope as CBH-5 at a reduced affinity, or recognizes a separate spatially close epitope.

Analysis of the antibody competition with HMAb CBH-2 (FIG. 12), indicated that HMAb CBH-2 binding was inhibited to greater than 75% by itself and HMAbs CBH-5, -8C, and -8E. In contrast, CBH-7 inhibited binding to only Q1a proteins by 60%, and CBH-11 inhibited binding only to Q1b and Q2a proteins. As with HMAb CBH-5, no competition was observed with HMAbs CBH-4G, -4D, -4B, -9, or -17. Analysis of competition results with HMAb CBH-7 (FIG. 13) indicate that the only HMAb that significantly inhibited binding of CBH-7 was itself. These data demonstrate that among the broadly reactive HMAbs, CBH-2, -5, -11, and -7 all recognize distinct epitopes. The possibility remains that CBH-2, -8C, and -8E may recognize either the same epitope or two distinct epitopes. Additionally CBH-9, and CBH-4G may recognize the same epitope or two distinct epitopes, but their failure to compete with CBH-2, -5 etc. ensures that they do not recognize the same epitope(s) as the other broadly reactive HMAbs. Thus, minimally the broadly reactive HMAbs recognize five distinct epitopes.

Example 5

Assessment of HMAb Activity in the Neutralization of Binding Assay

The neutralization of binding (NOB) assays tests whether a given antibody or serum can prevent the binding of HCV E2 protein to a putative receptor, expressed on human T cell lines. The NOB assays was performed using methods and HCV E2 proteins previously described (Rosa et al., supra; Ishii et al., supra). Briefly, 1 µg of the HCV E2 1a protein produced in mammalian cells (Rosa et al., supra) was mixed with serial dilution of antibodies (from 0.1 to 300 µg/ml) and incubated for 30 min. at 37° C. Molt-4 cells ($10^5$) were added to the mixture and incubated on ice for 1 hour. After washing, the amount of HCV-E2 bound to Molt-4 cells was assessed by flow cytometry as described previously (Rosa et al., supra). The NOB titer is defined as the serum dilution that shows 50% neutralization of E2 binding.

The ability of HMAbs to inhibit binding of HCV 1a E2 to CD81 expressing target cells was assessed with the neutralization of binding (NOB) assay (Rosa et al., supra). HMAbs CBH-4D, 4B, 4G, and 17 did not block the binding of E2 to target cells at concentrations of less than 25 µg/ml. HMAbs CBH-2, -5, -7, -8C, -8E, and -11 achieved 50% inhibition at concentrations of 1 to 10 µg/ml in multiple experiments (Table 4).

Example 6

Effect of HCV HMAbs on E2 Binding to CD81: Microtiter Plate Assays

Recently, the human tetraspannin protein CD 81 has been identified as a potential receptor for HCV and the cellular target protein for HCV E2 in the NOB assay. The binding site for HCV E2 within CD81 has been localized to the large extracellular loop, CD81-LEL (Pileri et al., 1998 *Science* 282:938–941; incorporated herein by reference), previously referred to as extracellular loop 2 or LEL. To prevent confusion between E2 and LEL we have opted to refer to this region as the Large Extracellular Loop (LEL). The large extracellular loop of human CD81 (CD81-LEL) was expressed as a fusion protein with glutathione-S-transferase employing the pGEX vector (GST-2T). Construction and purification of the protein were as described (Flint et al., 1999 *J. Virology* 73:6235–6244; incorporated herein by reference). This CD81-LEL-GST fusion protein was used to determine which HMAbs could recognize CD81-HCV E2 complexes. A schematic of this assay is provided in FIG. 14. Microtiter plate wells were coated with 100 ng of purified CD81-LEL or non-recombinant GST diluted in PBS. After 2 hours at 37° C., wells were washed one time with TBS and blocked by incubation with 150 μl of BLOTTO for 1 hour at RT. Extract from BSC 1 cells infected with HCV E2 expressing vaccinia virus was combined with test antibody in 100 μl of BLOTTO in coated plates that were incubated overnight with gentle agitation at 4° C. Wells were then washed three times with TBS followed by adding appropriate alkaline-phosphate conjugated secondary antibody and PNPP substrate as described in Example 4.

To confirm the NOB results using E2 proteins of multiple genotypes, we assessed whether the HCV HMAbs could inhibit the interaction of HCV E2 with CD81. Microtiter plates were first coated with purified CD81-LEL glutathione-S-transferase fusion protein to which an excess HCV E2 was added in the presence of the HCV HMAbs. Because HCV E2 binds specifically to human CD81 but not CD81 proteins of most other primates (*Rosa* et al., supra), the E2 proteins were produced in the green monkey kidney cell line BSC-1 to minimize the effect of endogenous CD81. Both anti-HCV and control antibodies were not captured by purified non-recombinant glutathione-S-transferase. Nor were the HCV or control antibodies captured by CD81 when combined with extracts of BSC-1 cells infected with wild type vaccinia virus (data not shown).

The NOB negative HMAb CBH-4G was captured onto CD81 coated plates to equivalent extents with E2 proteins of all four genotypes tested. The HMAbs CBH-4B, -4D and -17, were captured to variable extents onto CD81 coated plates by HCV 1a or 1B E2 proteins but not HCV 2A or 2B E2 proteins, consistent with the reactivity of these HMAbs with GNA captured E2 protein (FIG. 15). Titration analysis of the four NOB negative HMAbs confirmed that they all bound to HCV1b E2 protein with 50% of maximum binding be obtained at concentrations between 1 and 10 μg/ml (Table 4). None of the NOB positive antibodies, CBH-2, -5, -7, -8C, -8E, and -11 were captured by CD81 and E2 proteins of any of the our genotypes tested (FIG. 15). Similar results were obtained when the HCV antibodies were added to wells on which HCV 1b E2 protein was already bound to CD81-LEL (data not shown) indicating that the results obtained were independent of each other of addition of the E2 protein and the HCV HMAbs. Titration analysis of HMAbs CBH-2 and 7, which are strongly reactive with GNA captured E2 but negative with CD81 bound E2, confirmed that these antibodies did not bind to CD81-LEL E2 complex at concentrations of up to 25 μg/ml (data not shown). Thus, six HMAbs inhibited the binding of HCV E2 of multiple genotypes to CD81-LEL.

TABLE 4

Inhibition of HCV E2-CD81 Binding by Anti-HCV HMAbs

| HMAb | NOB 1a[a] | CD81 1b E2[b] |
|---|---|---|
| CBH 2 | 5 μg/ml | – |
| CBH 5 | 2 μg/ml | – |
| CBH 7 | 7 μg/ml | – |
| CBH 8C | 10 μg/ml | – |
| CBH 8E | 8 μg/ml | – |
| CBH 11 | 3 μg/ml | – |
| CBH 4G | – | 3 μg/ml |
| CBH 9 | – | 1 μg/ml |
| CBH 4B | – | 0.4 μg/ml |

TABLE 4-continued

Inhibition of HCV E2-CD81 Binding by Anti-HCV HMAbs

| HMAb | NOB 1a[a] | CD81 1b E2[b] |
|---|---|---|
| CBH 4D | – | 2 μg/ml |
| CBH 17 | – | 3 μg/ml |
| R04 | – | – |

[a]HMAb reactivity in representative NOB assays are presented as μg/ml of antibody that results in 50% inhibition of E2 binding to CD81 expressing T cells. Antibodies were tested at concentrations that ranged from 0.1 to 300 μg/ml. (–) = negative.
[b]HMAb reactivity is presented as the concentration of antibody (in μg/ml) that results in 50% of maximum binding to E2 captured by GNA or E2 captured by a CD81-LEL. (–) = negative.

Example 7

Effect of HCV HMAbs on HCV virion binding to CD81

The virion-CD81 binding assay was performed as previously described (Pileri et al., 1998 *Science* 282:938–941; incorporated herein by reference). Briefly ¼" polystyrene beads (Pierce, Rockford Ill.) were coated overnight with 50 μg/ml of purified recombinant LEL-TRX protein (Pileri et al., supra) in a citrate buffer pH 4.0 at room temperature and then blocked for one hour with 2% BSA in 50 mM Tris.C1 pH 8, 1 mM, EDTA, 100 mM NaCl (TEN) buffer. Serum containing $5 \times 10^5$ HCV RNA genomes was diluted in 200 μl TEN buffer with 10 μg of purified monoclonal antibodies and incubated for one hour at 4° C. The diluted serum was then added to the coated beads and incubated at 37° C. for 1–2 hours. After removal of supernatant, each bead was washed five times with 15 ml TEN buffer and bound virus was extracted using a commercially available kit (Qiagen, Basel, Switzerland). Polymerase china reaction mediated evaluation of the RNA copy number was performed using a Perkin Elmer ABI 7700 sequence detection system, as described (Pileri et al., supra).

Several of the HCV HMAbs that blocked recombinant E2 binding to CD81 were tested for the ability to interfere with the binding of HCV virions (including E1 and E2 protein expressed in a lipid bilayer) binding to CD81. Because of the lack of HCV culture assays in vitro, we took advantage of a PCR assay developed to demonstrate binding of envelope associated HCV RNA to CD81 (Pileri et al., supra). A schematic of this assay is depicted in FIG. 16. Briefly, the major extracellular loop of CD81 is attached to polystyrene beads and incubated with infectious plasma containing a known amount of HCV 1a RNA molecules. After washing the amount of bead associated virus was measured by quantitative RT-PCR. The four NOB positive HMAbs with the highest apparent activity, HMAbs CBH-2, CBH-5, CBH-7, and CBH-11, were evaluated. No inhibition of virus binding was observed with a control antibody or with the NOB positive antibodies CBH-7 or CBH-11. In contrast, pre-incubation of infectious plasma with 10 μg/ml of HMAbs CBH-2 and CBH-5 inhibited HCV binding to CD81 (FIG. 17). These results support the view that these antibodies could bind HCV virions and may have a neutralizing effect in vivo.

Combining all of the results obtained in the above assays it is possible to construct a preliminary epitope assessment of the 11 HMAbs described herein. This is presented in Table 5. The epitope recognized by HMAb CBH-8C is separated from that recognized by HMAbs CBH-2 and/or CBH-8E by virtue of the very similar titrations obtained with CBH-8C with all four genotypes of HCV E2. CBH-2 and CBH-8E have the property of repeatedly exhibiting somewhat less reactivity with genotype 1b and 2b relative to values obtained with genotypes 2a and 1a. The assessment of the other distinct epitopes is very straightforward given the results obtained. However, it remains possible that additional experiments will serve to segregate the epitopes recognized by CBH-4G and CBH-9 and/or the epitopes recognized by CBH-8E and CBH-2.

Example 8

Microtiter Plate Assay for HCV Neutralizing Antibodies

To assist in the treatment and management of individuals with HCV infection, it would be desirable to know whether they have a potent anti-viral immune response. Although several assays that can measure neutralizing antibody titers have been described, including the neutralization of binding assay described above and ex vivo neutralization prior to inoculation of chimpanzees these assays are all cumbersome and are not suited to testing large numbers of samples. Therefore we employed HMAb CBH-4G which is equivalently reactive to HCV E2-CD81 complexes with E2 proteins of multiple genotypes in an inhibition assay to determine the level of neutralizing of binding like antibodies in human sera. Individual wells of microtiter plates were coated with either 500 ng of purified GNA lectin or 100 ng of GST-CD81-LEL fusion protein for one hour at 37° C. Wells were then washed one time with TBS and blocked for one hour with 150 µl of BLOTTO at room temperature. The wells are then washed one time with TBS, and various dilutions of test sera or monoclonal antibodies were added to the appropriate wells in a total volume of 50 µl. At the same time 15 µl of HCV E2 protein containing extract was combined with 4 µg/ml of a biotinylated preparation of HMAb CBH-4G in a total volume of 50 µl of BLOTTO for each well. After incubation for 20 minutes at 4° C. the E2 CBH-4G mixture was added to microtiter plate wells already containing the test antibody. The entire plate was then incubated overnight at 4° C. with gentle agitation. The next morning the contents of the wells were discarded and the wells washed three times with TBS. This was followed by the addition of 100 µl of strepavidin conjugated alkaline phosphatase (Amersham-Pharmacia, Piscataway N.J.) diluted 1/1000 in PBS plus 0.1% Tween-20 (Sigma, St Louis Mo.). The plates were then incubated for one hour at room temperature after which time the wells were washed four times with TBS and bound biotinylated antibody detected by incubation with PNPP substrate as described in examples 2 and 4 above.

The results obtained when the panel of 11 HCV HMAbs was used as test antibodies are presented in FIG. 18. In this experiment the ability of a 20 µg/ml concentration of the HCV HMAbs to inhibit the binding of HCV genotype 1a E2 protein to human CD81-LEL was evaluated. Inhibition of binding observed in CD81-LEL coated wells are compared to results obtained with the same antibody in GNA lectin coated wells. Inhibition observed of E2 binding in GNA coated wells reflect inhibition of the interaction between the CBH-4G detection antibody and the competing antibody. Inhibition observed specifically in the CD81-LEL coated wells reflects inhibition of the interaction between CD81 and E2. None of the 11 HCV HMAbs or the control antibody, R04 exhibited more than 50% inhibition of CBH-4G binding to E2 captured by GNA. In contrast five of the six HCV HMAbs previously shown to be neutralization of binding positive strongly inhibited binding of CBH-4G-E2 complex to CD81-LEL. The lone exception was HMAb CBH-11, which does not efficiently recognize the Q1a isolate of genotype 1a E2 protein. The HMAbs CBH-4b, -4G, -4D, -9 and -17, which recognize CD81-LEL-E2 complexes all minimally effected binding of CBH-4G bound E2 to CD81-LEL. Thus HMAb CBH-4G can effectively discriminate between antibodies that can or cannot inhibit the interaction of HCV E2 with CD81.

TABLE 5

Preliminary epitope analysis of HCV HMAbs

| Epitope | Type[1] | HMAb | Inhibits E2-CD81[2] | Binds to HCV Virion | Comp w CBH 2 | 1a | 1b | 2a | 2b |
|---|---|---|---|---|---|---|---|---|---|
| 1 | CONF | CBH 2 | + | + | + | + | + | + | + |
|   |   | CBH 8Ec | + | ND | + | + | + | + | + |
| 2 | CONF | CBH 5 | + | + | +/−[3] | + | + | + | + |
| 3 | CONF | CBH 7 | + | − | − | + | + | + | + |
| 4 | CONF | CBH 11 | + | − | + | − | + | + | + |
| 5 | CONF | CBH 8C | + | NDn | + | + | + | + | + |
| 6 | CONF | CBH 4G | − | ND | − | + | + | + | + |
|   |   | CBH 9 | − | ND | − | + | + | + | + |
| 7 | CONF | CBH 4B | − | ND | − | + | + | − | − |
|   |   | CBH 4D | − | ND | − |   |   | − | − |
| 8 | LIN | CBH 17 | − | ND | − | + | + | − | − |

[1]CONF = recognizes a conformational epitope; LIN = recognizes a linear epitope
[2]Summarizes results obtained in NOB assay and CD81-E2 binding assays described above
[3]Non reciprocal partial competition is observed. cBH-2 inhibits binding of CBH-5 to HCV 1 a or 1b E2 protein at a level of ~50%. CBH-5 inhibits binding of CBH-2 to HCV E2 of genotypes 1a, 1b, 2a, or 2b to ~80%.

Accordingly this experiment was then repeated using HCV and control sera in place of the HCV HMAbs (FIG. 19). Six genotyped HCV sera (three genotype 1a sera and three genotype 2b sera) and two HCV negative sera were tested against the homologous E2 protein at a dilution of 1/1000. As seen with the HCV HMAbs little or no inhibition of HCV E2 binding to GNA was observed. Nor did either of the negative sera significantly affect binding of HCV E2 to CD81-LEL. In contrast a wide variation of inhibition of E2 binding to CD81-LEL was observed with the HCV sera. Thus HMAb CBH-4G binding to a putative receptor, CD81, in a microtiter plate format.

It is evident from the above results that the monoclonal antibodies are an important addition in the development of diagnostics and therapies for the treatment of patients having HCV. By virtue of recognizing genotypes 1 and type 2, HCV assays can be performed with a higher expectancy of fewer false negatives and fewer antibodies are required for performing the assays to identify HCV infection. The antibodies will find use in a wide variety of protocols. In addition, the antibodies may be used to identify genotype, isolating virion particles, and identifying mimotopes. By virtue of their being human, they may be used in therapy, either prophylactic, to protect a subject who may be exposed to the virus, or therapeutic, to reduce the effective viral load of a patient.

Example 9

Competition Analysis and Epitope Localization of Human Monoclonal Antibodies to HCV E2 that Inhibit HCV Replication in a Small Animal Model of HCV Infection Materials and Methods Cell lines and viruses. HeLa cells were grown in minimal essential media (MEM, Life Technologies, Bethesda, Md.) supplemented with 10% fetal calf serum (FCS) and 2 mM glutamine. Human embryonic kidney (HEK-293) cells were maintained in Dulbecco's modified minimal essential medium (DMEM, Life Technologies, Gaithersburg, Md.) supplemented with 10% fetal calf serum (GIBCO) and L-glutamine (2 mM) (GIBCO) in 5% $CO_2$. Recombinant vaccinia virus expressing HCV envelope proteins were constructed and grown as described (HCV JoV). Vaccinia virus 1488 expressing the structural proteins of HCV 1a strain H was obtained from Dr Charles Rice.

Monoclonal antibodies. The production, purification, and biotinylation of the HCV HMAbs were performed as described (HCV JoV). Rat monoclonal antibody 3/11 to HCV E2 was cultured as described previously and was obtained from Dr. Jane McKeating. Rat monoclonal antibody to the influenza hemagglutinin (HA) epitope was obtained from Roche Diagnostics (Indianapolis, Ind.). Murine monoclonal antibody to the c-myc epitope was obtained from Santa Cruz Biotechnology (Santa Cruz, Calif.).

Competition Assays. Monolayers of HeLa cells were grown to 80% confluence, infected with recombinant vaccinia virus expressing HCV E2, and cytoplasmic extracts prepared as described (HCV JoV). Microtiter plates were prepared by coating wells with 500 ng of purified *Galanthus nivalis* (GNA) lectin (SIGMA, St Louis, Mo.) in 100 µl of PBS for 1 hour at 37° C. Wells were washed with TBS (150 mM NaCl, 20 mM Tris-HCl, pH 7.5), and then blocked with 150 µl BLOTTO (TBS plus 0.1% Tween-20, 2.5% normal goat sera, 2.5% non fat dry milk) by incubation for 1 hour at room temperature. Plates were washed twice with TBS followed by the addition to each well of 15 µl of extract in 100 µl BLOTTO. After 1.5 hours at RT, plates were washed 3 times with TBS followed by the addition of competing antibodies at various concentrations in a total volume of 50 µl/well. Plates were incubated for 30 minutes at which point 50 µl/well of a 8 µg/ml (CBH-4G) or 4 µg/ml solution (all other HMAbs) of biotinylated test antibody was added. After incubation for 1.5 hours at room temperature, the plates were washed 3 times with TBS, and 100 µl of 1/1000 diluted alkaline-phosphatase conjugated streptavidin (Amersham-Pharmacia Biotech, Piscataway, N.J.) was added. After 1 hour at room temperature, the plates were washed 4 times with TBS followed by 30 minutes incubation with a 1 mg/ml solution of p-nitrophenyl phosphate (PNPP). Absorbance was measured at 405 nm with a multi-well plate reader (BioTek Instruments, Winooski Vt.). Signals obtained with biotinylated test antibody and E2 in the presence of competing antibody were compared to signals obtained from test antibody and E2 in the absence of any competing antibody.

Isolation and cloning of HCV E2 deletion constructs. HCV 1b RNA was isolated from serum from an individual infected with HCV genotype 1b using the PureScript (Gentra systems, Minneapolis, Minn.) according to the manufacturer's instruction. Both the vaccinia virus recombinant Q1b and all of the HCV 1b deletion constructs were derived from the same individual. HCV RNA was converted into cDNA using random primers and reverse transcriptase (Perkin-Elmer Applied Biosystems, Foster City, Calif.) according to manufacture's protocol at 42° C. for 30 min. Fragments of HCV E1 were amplified by polymerase chain reaction (PCR) using pfu taq polymerase (Stratagene, La Jolla, Calif.) from cDNA with appropriate oligonucleotide primers (obtained from Integrated DNA Technologies, Corlville, Iowa) that contained flanking Bgl II or Pst I restriction sites. HCV strain H constructs were amplified by PCR from viral stocks of vaccinia virus construct vv1488. Amplified DNAs were subsequently ligated into the Bgl II and Pst I digested pDisplay plasmid (Invitrogen, Carlsbad, Calif.). All plasmids were constructed using standard procedures (28). The presence of in-frame HCV inserts was confirmed by DNA sequencing using ABI PRISM Dye terminator cycle sequencing on an automated sequencer (PE-Applied Biosystems, Foster City Calif.).

Expression of HCV E2 deletion constructs. Human embryonic kidney (HEK) 293 cells were seeded to obtain 60–70% confluence by the following day. For transfection of a T-75 flask, a mixture of µg of the appropriate plasmid DNA and µg of PerFect Lipid Pfx-2 (InVitrogen, Carlsbad, Calif.) were combined in ml of serum free media at a DNA:lipid ratio of 1:6 (w/w). After four hours incubation at 37° C. the transfection solution is replaced with 2.5 ml of complete medium and cells were grown for an additional 24 hours. Cell extracts were prepared by washing cells with PBS and resuspending them in 1 ml of lysis buffer (150 mM NaCl, 20 mM Tris pH 7.5, 0.5% deoxycholate, 1.0% Nonidet-P40, 1 mM EDTA, 0.5 mg/ml Pefabloc (Boehringer Mannheim, Indianapolis, Ind.), 2 µg/ml Aprotinin, 2 µg/ml Leupeptin, and 1 µg/ml Pepstatin). Nuclei were pelleted by centrifugation at 18,000×g at 4° C. for 10 minutes. For Western blot analysis, extracts were combined 1 to 1 with 2× sodium dodecyl sulfate polyacrylimide electrophoresis sample buffer (SDS-SB; 20% glycerol, 10% β-mercaptoethanol, 4.8% SDS, 0.125 mM Tris pH 6.8). Proteins were denatured via heating to 95° C. for five minutes followed by sodium dodecyl sulfate polyacrylimide electrophoresis (SDS-PAGE) in 12% polyacrylamide gels of 20 µl aliquots of the denatured extracts. SDS-PAGE and subsequent Western blotting were performed using standard methods.

For microtiter plate assays, microtiter plates were prepared by coating wells with 500 ng of purified *Galanthus nivalis* (GNA) lectin (SIGMA, St Louis, Mo.) in 100 µl of PBS for 1 hour at 37° C. Wells were washed with TBS (150 mM NaCl, 20 mM Tris-HCL, pH 7.5), and then blocked with 150 µl BLOTTO (TBS plus 0.1% Tween-20, 2.5% normal goat sera, 2.5% non fat dry milk) by incubation for 1 hour at room temperature. Wells were washed twice with TBS followed by the addition of 25 µL of extract from HEK-293 cells transfected with E2 deletion constructs diluted in 75 µl of BLOTTO. After 1.5 hours at room temperature, plates were washed 3 times with TBS followed by the addition of monoclonal antibodies at various concentrations. Plates were incubated for 1.5 hours, washed 3 times with TBS, and then 100 µl of appropriate alkaline-phosphatase conjugated secondary antibody, diluted in BLOTTO as recommended by the manufacturer, was added (for anti-human and anti-mouse, Promega, Madison, Wis., for anti-rat, Kirkegard and Perry, South San Francisco Calif.). After 1 hour at room temperature, the plates were washed 4 times with TBS followed by incubation for 30 minutes with a 1 mg/ml solution of p-nitrophenyl phosphate (PNPP). Absorbance was measured at 405 nm with a multi-well plate reader (Du Pont Co, Wilmington, Del.).

Flow cytometric analysis. Various dilutions of test antibody in a total volume of 100 µl of staining solution (PBS plus 1% FCS and 0.1% sodium azide) were combined with $10^6$ viable HCV E1 expressing or control HEK-293 cells, resuspended in 100 µl of staining solution, and incubated at 4° C. for 45 minutes. After adding an additional 3 ml of staining solution, the cells were pelleted by centrifugation for 10 minutes at 500×g at room temperature. The pellet was reserved and resuspended in 100 µl of FITC conjugated secondary antibody diluted as recommended by the manufacturer (Jackson Immunoresearch laboratories, West Grove, Pa.) in staining solution. After 45 minutes at 4° C., 900 µl of staining solution was added, and the cells were pelleted as above. The cells were then resuspended in 1 ml of fixative solution (3.8% formaldehyde in PBS), and the amount of HMAb bound to the surface of cells was analyzed on a FACScalibur (Becton-Dickinson, San Jose, Calif.). For two color staining secondary antibodies were conjugated to R-phycoerythrin and fluorescence monitored at 606 nm while EGFP fluorescence was monitored at 545 nm.

Results

Human monoclonal antibodies recognizing HCV E2 were obtained from two sources. Ten HMAbs (CBH-2, CBH-4B, CBH-4D, CBH-4G, CBH-5, CBH-7, CBH-8C, CBH-8E, CBH-11, and CBH-17) were obtained from an individual who had an asymptomatic infection with HCV of genotype 1b. The HMAb XTL-U68 was obtained from an individual who had cleared HCV infection with a separate isolate of HCV 1b. The antibodies varied in the breadth of their reactivity with different genotypes of HCV E2 and in their ability to inhibit the interaction of HCV E2 with human CD81. The designations, reactivity, and properties of the HCV HMAbs are summarized in Table 6.

TABLE 6

| | | | HCV HMAbs | | | | |
|---|---|---|---|---|---|---|---|
| HCV E2 Antibodies | | | E2 Reactivity[3] | | Functional Assays | | |
| HMAb[1] | Heavy[2] | Light | Gtyp 1 | Gtyp 2 | Inhibit CD81[4] | Bind Virions[5] | Trimera[6] |
| CBH-2 | VH5-51 | VκIII A27 | 7 (8) | 2 (2) | ++ | ++ | ++ |
| CBH-8E | VH1-69 | VκI O12 | 8 (8) | 2 (2) | ++ | ND | ND |
| CBH-5 | VH1-69 | VκI L12 | 8 (8) | 2 (2) | ++ | + | +/− |
| CHB-8C | VH4-59 | VκIII L6 | 5 (8) | 2 (2) | ++ | ND | ND |
| CBH-11 | VH1-69 | VκI L12 | 4 (8) | 2 (2) | ++ | − | ND |
| CBH-7 | VH1-69 | VκI O12 | 8 (8) | 2 (2) | ++ | − | ++ |
| XTL-U68 | IgG1 | ND | 8 (8) | 2 (2) | − | ++ | ++ |
| CBH-4G | VH1-9 | VκI A20 | 8 (8) | 2 (2) | − | ND | ND |
| CBH-4B | VH1-9 | VκIII A27 | 8 (8) | 0 (2) | − | ND | ND |
| CBH-4D | VH1-9 | Vλ 2a2 | 8 (8) | 0 (2) | − | ND | ND |
| CBH-17 | VH3-73 | Vλ 3h | 7 (8) | 0 (2) | − | ND | ND |
| 3/11 | ratMAb | | 8 (8) | 2 (2) | ND | ND | ND |
| HA | ratMAb | | 2 (2) | 0 (0) | − | ND | ND |
| R04 | IgG1 | | 0 (8) | 0 (2) | − | − | ND |

[1]CBH Antibodies are further described in Hadlock et al. J. Virol. 74:10407–10416, 2000; incorporated herein by reference. HA recognizes a synthetic epitope present in some HCV E2 constructs. rMAb 3/11 was generously provided by Jane McKeating, Ph.D.
[2]Antibody sequences are from Chan HC, et al. In Press Blood.
[3]The number of reactive E2s is followed by the total number tested (in parentheses).
[4]++ = inhibits binding of E2 to CD 81. − = no inhibition. ND = not done.
[5]++ = binds to HCV virions in immunoprecipitation and or CD 81 inhibition assays.
[6]++ = significantly inhibits serum HCV levels in Trimera mice. Test HMAb is pre-incubated with HCV inoculum prior to exposure to human liver and transplantation into Trimera mice. HCV serum viral loads are determined at 15–20 days post transplantation.

Sequence analysis of the IgG1 genes of 10 of the 11 HMAbs confirmed that they were derived from independent B cells. Of note, HMAb XTL-U68, CBH-4B, CBH-4G, CBH-4D, and CBH-17 all failed to inhibit the binding of E2 to CD81-LEL (Table 6).

Competition assays were employed to determine the number of distinct sites within E2 that were reactive with the HMAbs. Individual HMAbs were purified, biotinylated, and the binding of the antibodies in the presence of increasing concentrations of competing antibody was determined. Representative binding curves are presented in FIG. 21. Binding of HMAbs CBH-2, CBH-5, CBH-8C, and CBH-11 to HCV 1b E2 were all significantly inhibited by an excess of HMAbs CBH-2, -8E, -5, -8C, and -11. In general HMAb CBH-5 exhibited the highest level of inhibition, and CBH-2 and CBH-8E exhibited the weakest inhibition. For HMAbs CBH-2, -5, -8C, and -11, an intermediate level of inhibition was observed with HMAb XTL-U68, and no significant inhibition was observed with a control HMAb, R04, or HCV HMAbs CBH-7, CBH-4B, and CBH-4G. In contrast, HMAb CBH-7 was strongly inhibited by itself or HMAb XTL-U68, very weakly inhibited by HMAb CBH-4B, and unaffected by the presence of HMAbs CBH-2, -5, -8C, -8E, -11, -4G, or the control antibody. Similarly HMAb CBH-4B was strongly inhibited by HMAb XTL-U68, and showed intermediate levels of inhibition with HMAbs CBH-7, CBH-4B, and CBH-4G. HMAbs CBH-2, -5, -8C, -11, and 8E recognized epitopes that were in close proximity to each other and potential define an antibody binding site within HCV E2

The results from the full series of inhibition experiments are presented in FIG. 22. Five antibodies CBH-2, -8E, -5, -8C, and -11 that recognize conformational epitopes and can inhibit the binding of E2 with CD81-LEL all significantly cross competed and formed one competition group (Group I). A second competition group (Group II) contains HMAbs XTL-U68 and CBH-7. A third competition group is formed by HMAbs CBH-4G, CBH-4B, and CBH-4D, and a fourth competition group is formed by CBH-17, the only antibody in the panel to recognize a linear epitope. The binding of antibodies from group I was only marginally affected by antibodies from group II and not affected at all by antibodies from groups III or IV. The binding of antibodies from group II to E2 was not affected by the presence of antibodies from any other group. Antibodies from group III were unaffected by the presence of antibodies from group I and either strongly inhibited, or in the case of CBH-4G binding in the presence of CBH-7, stimulated by the presence of antibodies from group III. HMAb CBH-17 did not influence the binding of any of the other antibodies. Thus the 11 HCV HMAbs defined four relatively distinct antibody binding sites within HCV E2.

Currently there is no efficient culture system for the propagation of HCV. When HCV structural proteins are expressed in mammalian derived cells the proteins are usually retained intracellularly. Recently, however several groups have reported the successful expression of HCV E2 on the surface of mammalian cells. Since HCV E2 expressed on the surface of cells might more closely mirror the structure of HCV E2 on the surface of infectious virions, we expressed the extracellular domain of HCV 1b E2 (amino acids 384–661) in a the pDisplay vector. The HCV E2 sequences were expressed in-frame with the transmembrane domain of platelet derived growth factor receptor (PDGFR). The signal sequence at the carboxy terminal of the HCV E1 protein was replaced with the murine IgK leader sequence. Strong linear epitopes from influenza virus hemaglutinin (HA) and c-myc are located immediately in front and behind the HCV sequences, respectively. The expected molecular weight of the HCV 1b construct sf1b (expressing amino acids 384–661 of HCV 1b E2) was 42 kD, prior to glycosylation. Two different immunoreactive proteins were produced by the sf1b-E2 cell line when protein expression was analyzed by Western blot. The first is a relatively discreet band migrating at 68–70 kdal. This species was efficiently purified by affinity chromatography with GNA lectin and is an intracellular form of E2 with mannnose-rich carbohydrate chains. The second immunoreactive proteins is a heterogenous smear which ranged in size from 70 to 98 kD. This species was not efficiently purified by GNA lectin chromatography and is assumed to have complex carbohydrate chains and be the major species present on the surface of the cells. DNA sequencing confirmed cloning of the expected insert with no frame shifts or terminations.

The HCV E2 construct sf1b-E2 was introduced into CHO cells and a cell line expressing the protein was obtained. The sf1b-E2 expressing cells were then combined with the HCV HMAbs or control antibodies, and the ability of the HMAbs to bind to cell-surface expressed HCV E2 was determined. When stained with the monoclonal antibody to the HA epitope, a strong signal was obtained from greater than 95% of the cells. No specific signal was obtained from the parent CHO cells nor was any signal obtained with the sf1b-E2 expressing cell line and control antibody. The HCV HMAbs CBH-2, CBH-7, and CBH-4B all exhibited staining of the sf1b-E2 cell line that was equivalent to that observed with the HA epitope. In contrast the HMAbs CBH-11 and CBH-17, although also reactive with the cell surface expressed E2 protein, exhibited 10 fold reduced staining relative to the other HMAbs (Table 7). Thus 9 of the 11 HCV HMAbs reacted strongly with cell-surface expressed E2 protein, and two of the HMAbs exhibited significant reductions in reactivity when E2 was expressed on the cell surface.

TABLE 7

Reactivity of HCV HMAbs with intra & extracellular E2 proteins

| HMAb | Sf-1b | | pDN-411 | | PDN-447 | | PDN-470 | | PDC-644 | | PDC-579 | |
|---|---|---|---|---|---|---|---|---|---|---|---|---|
| | GNA[1] | Flow[2] | GNA | Flow[3] | GNA | Flow | GNA | Flow | GNA | Flow | GNA | Flow |
| CBH 2 | ++ | 338 | + | | − | | − | | + | | − | |
| CBH 8E | ++ | 408 | + | | − | | − | | + | | − | |
| CBH 5 | ++ | 546 | ++ | 17 | − | 2 | − | 2 | ++ | 28 | − | 2 |
| CBH 8C | ++ | 282 | ++ | | − | | − | | ++ | | − | |
| CBH 11 | ++ | 43 | ++ | | − | | − | | ++ | | − | |
| CBH 7 | ++ | 303 | ++ | 19 | ++ | 26 | ++ | 14 | ++ | 27 | − | 2 |
| CBH 4G | ++ | 175 | ++ | | ++ | | ++ | | ++ | | − | |
| CBH 4B | ++ | 241 | ++ | 17 | ++ | 21 | ++ | 9 | ++ | 18 | − | 2 |
| CBH 4D | ++ | 173 | ++ | | ++ | | + | | ++ | | − | |
| CBH 17 | ++ | 23 | + | | ++ | | ++ | | − | | − | |
| HA | ++ | 375 | ++ | 42 | ++ | 36 | ++ | 19 | ++ | 75 | ++ | 40 |
| c-myc | ++ | 68 | ++ | | ++ | | ++ | | ++ | | ++ | |
| R04 | − | 3 | − | 2 | − | 2 | − | 2 | − | 2 | − | 2 |

[1]Results in GNA capture assays are expressed as ++ strongly positive (OD > 0.5), +positive (~OD 0.1 to 0.5), − negative.
[2]Mean Fluorescence obtained with 10 ug/ml of indicated HMAb staining CHO cells permanently expressing the sf1b-E2 construct.
[3]Mean Fluorescence obtained with 10 ug/ml of indicated HMAb staining HEK-293 cells transiently transfected with the indicated HCV E2 constructs. A blank cell indicates the HMAb was not tested by flow cytometry.

Next we were interested in localizing the regions of HCV E2 that contained the binding sites recognized by antibodies from the four different groups. To that end deletions were made from the amino terminal and carboxy terminal ends of sf1b-E2. One of the deletions pDN411 removed the hypervariable region of HCV sf1b-E2. The other deletions removed larger portions from the amino or carboxy terminals of sf1b-E2. The deleted E2s were then re-cloned into the vector pDisplay which allows for the cell surface expression of inserts. HCV E2 deletion constructs expressing sequences from genotype 1b and the H isolate of HCV 1a were constructed (SEQ ID NO: 28–35) (FIG. 23). The expression of the E2 deletion constructs was verified by transfection into HEK-293 cells followed by Western blot analysis of cytoplasmic extracts using a monoclonal antibody to the HA epitope (FIG. 24). No reactivity was observed with a control antibody to a CMV protein (data not shown). As seen with sf1b-E2, both a faster migrating discreet band and a slower migrating heterogenous smear were observed with all constructs. Similar results were obtained with sfH1a-E2 and pDNH-411 (data not shown). DNA sequencing confirmed that each of the constructs expressed the expected sequences with no frame shifts or terminations.

Therefore, the HCV E2 deletion constructs were transfected into HEK-293 cells, cytoplasmic extracts prepared, and intracellular forms of E2 captured onto microtiter plates using GNA lectin. The reactivity of the HCV HMAbs with the GNA captured E2 was then determined. As expected, all of the HCV HMAbs reacted with sf1b E2 protein and none reacted with proteins captured from extracts of mock-transfected HEK-293 cells (FIG. 25). Also all of the HCV HMAbs were strongly reactive with E2 produced by pDN-411, indicating that the epitopes recognized by the HMAbs did not include HVR-1. Next, the same panel of antibodies was tested against the extracellular domain of HCV E2 derived from strain H both with (sfH1a-E2) (SEQ ID NO: 29) or without (pDNH-411) HVR1 (SEQ ID NO: 30). HCV HMAbs CBH-8C and CBH-11 did not recognize either sfH1a-E2 or pDNH-411, suggesting that the epitopes recognized by these two HMAbs were mutated in strain H derived E2 protein. Significant reductions in the reactivity of HMAbs CBH-2, CBH-8E, and CBH-5 with strain H E2 protein were also noted. These HMAbs retained reactivity with the HVR1 construct pDNH-411, confirming that the epitope recognized by these HMAbs was outside of HVR1. The other HCV HMAbs and control antibodies exhibited equivalent reactivity with the strain H derived E2 proteins and the genotype 1b E2 proteins. Thus nine of the 11 HCV HMAbs recognized an epitope conserved between sf1b-E2 and sfH1a-E2.

Further deletion of amino acids 384–446 (pDN-447) (SEQ ID NO: 31) or 384–469 (pDN-470) (SEQ ID NO: 32) from the sequences of sf1b-E2 abrogated the reactivity of all Group I HMAbs (CBH-2, -8E, -5, -8C, and -11). Also rat MAb 3/11 which was previously determined to recognize a linear epitope consisting of amino acids 384 to 445 of HCV E2 was non-reactive with pDN-447 and pDN-470. In contrast, HCV HMAbs of group II, III, and IV retained their reactivity with both constructs. PDN-447 and pDN-470, indicating that the epitopes recognized by HMAbs from these groups were located in the central to carboxy terminal regions of HCV E2. Finally, E2 proteins with deletions in the carboxy terminal region were evaluated with the HCV HMAbs. All of the HCV HMAbs, except for CBH-17, were reactive with E2 proteins expressing amino acids 384–644 of HCV E2 (pDC-644) (SEQ ID NO: 33). In contrast, none of the HCV HMAbs were reactive with constructs expressing amino acids 384–579 of HCV E2 (pDC-579) (SEQ ID NO: 34). The rat MAb 3/11 retained reactivity with both carboxy terminal deleted E2 proteins as did Mabs to the HA or c-myc epitopes. Thus deletion of HCV E2 sequences between amino acids 644 to 579 is sufficient to abrogate reactivity of all 10 HCV HMAbs that recognize conformational epitopes.

Use of the GNA assay confirmed reactivity of the HCV HMAbs with the intracellular forms of the deletions. To verify the reactivity of the HCV HMAbs with the cell surface expressed E2 of the same deletion constructs the binding of the HMAbs with cells expressing the E2 deletion constructs was evaluated by flow cytometery. Constructs were evaluated with CBH-5 from HMAb group I, CBH-7 of HMAb Group III, and HMAb CBH-4B of HMAb group III. Control antibodies included rat MAb 3/11 and HA. Representative results with E2 deletion constructs pDN411 and pDN447 are presented in FIG. 25. Results with all of the E2 deletions are included in Table 7. Because the E2 deletions were introduced into the HEK-293 cells via transient transfection only about 50–60% of the cells took up plasmid and expressed E2 proteins. Thus the geometric means of the fluorescence observed are noteably reduced relative to those obtained with the cloned CHO cell line. Nevertheless, results obtained with HMAbs CBH-5, CBH-7, and CBH-4B by flow cytometry were in complete concordance with the results of the GNA capture assay (Table 7). Thus HMAbs from groups II and III recognize epitopes located between amino acids 470 to 644 of HCV E2. HMAbs from group I recognize an epitope located between amino acids 411–644 of HCV E2.

Example 10

High Levels of Antibodies that can Neutralize HCV Infection are Rare in HCV Infected Individuals Patients and Methods Patients. Sera evaluated were from individuals undergoing nucleic acid testing to confirm or follow up a diagnosis of hepatitis C infection between 1991 and 1999. All individuals were being seen for their hepatitis at clinics in the San Francisco bay area. The subjects were positive for HCV RNA by polymerase chain reaction, negative for the presence of hepatitis B virus surface antigen, genotyped, and not receiving antiviral therapy at the time the sample was obtained. Demographic information was obtained from medical records and included age, sex, date of diagnosis, previous interferon therapy, alanine transaminase (ALT) value, and potential route of exposure. The majority of the subjects reported at least one risk-factor for HCV infection. Not all information was available from all subjects. Liver biopsies, when performed, were scored using the histologic activity index (HAI). Genotype analysis was performed using the InnoLIPA assay according to manufacturer's instructions (Innogenetics, Leuven, Belgium). HCV viral load determinations were performed with the COBAS Amplicor HCV monitor kit (Roche molecular systems, Alameda, Calif.). HCV negative control sera were obtained from plasma of blood donors to the Stanford Medical School blood center, and were negative for the presence of transfusion-transmitted viruses by standard antibody-based screening assays.

E2 Antibody Screening of HCV sera. Monolayers of HeLa cells were grown to 80% confluence and infected with HCV E2 expressing vaccinia virus. Twenty-four hours after infection cells were harvested and extracts were prepared as described (Hadlock et al., 2000). ELISA assay for HCV E2 reactivity were performed as outlined below. Microtiter plate wells were coated with 500 ng of purified *Galanthus nivalis*, lectin in 100 ml of PBS for 1 hour at 37° C. Wells were then washed with TBS and blocked by incubation with BLOTTO (TBS plus 0.1% Tween-20, 2.5% normal goat sera, 2.5% non fat dry milk). Plates were washed and each well received 15 ml HCV E2 containing extract diluted in BLOTTO. After incubation for 1.5 hours at 25° C., wells were washed with TBS followed by addition of increasing dilutions of sera from HCV infected or uninfected individuals diluted in BLOTTO. After incubation for 30 minutes biotinylated test HMAb was added to a final concentration of 2 mg/ml. The plates were incubated for 1.5 hours at 25° C., wells were washed three times with TBS and 100 ml of streptavidin-AP conjugate added for 1 hour at 25° C. Wells were washed 4 times with TBS followed by incubation with PNPP. Substrate development was allowed to proceed for 30 minutes, then the absorbence of the wells at 405 nm was determined using a multiwell plate reader.

For each dilution of competing serum the optical density (OD) reading obtained was compared to the OD obtained from wells without competing antibody. The resulting percentages of bound antibody were plotted versus the dilution and employed to calculate the dilution of sera that resulted in 50% inhibition of test HMAb binding. Sera that did not achieve 50% inhibition were assigned a titer of 40, which was less than the lowest dilution tested. Individuals evaluating sample seroreactivity were blinded to the viral load and clinical status of the samples they were testing. Statistical analysis was performed using InStat and Prism software packages (Graph Pad Software Inc, San Diego, Calif.).

RESULTS

In this study, sera from HCV-infected individuals were evaluated for the presence of antibodies capable of inhibiting the binding of CBH-2 and CBH-7 to HCV E2. Human monoclonal antibodies CBH-2 and CBH-7 were purified and biotinylated, and the dilution of serum that resulted in 50% inhibition of CBH-2 or CBH-7 binding to a genotype-matched E2 protein was determined. Sera from HCV-negative individuals were used to measure nonspecific binding and to establish a cutoff value. Sera from HCV-infected individuals were considered positive for the presence of competing antibody if 50% or greater inhibition of E2 binding was obtained at a dilution of 1/200 or greater (FIGS. 26 and 27). Among 74 sera from HCV-infected individuals positive for viral RNA, 35 (47%) were positive for antibodies inhibiting CBH-2 binding, and 32 (43%) were positive for antibodies inhibiting CBH-7 binding (FIGS. 28 and 29). Fifteen sera (20%) were negative for the presence of antibodies that inhibited both CBH-2 and CBH-7. Nineteen (27%) individuals has high titers (>1/1000) of antibodies that inhibited binding of CBH-2 or CBH-7 (see Table 8). These individuals had a significantly reduced median viral load ($2.4 \times 10^6$ vs. $4.7 \times 10^6$, p=0.035), but were not otherwise different than other HCV infected individuals. Thus, most HCV infected individuals are characterized by low levels of serum antibodies with putative neutralization activity. Individuals with low levels of CBH-2 or CBH-7 like HMAbs can be identified using a simple inhibition assay. Therapeutic use of HCV-neutralizing human monoclonal antibodies, such as CBH-2 and CBH-7, has the potential to be of value in these individuals.

TABLE 8

Distribution of CBH-7 inhibitory titers in HCV Sera

| Characteristic | N/Value | CBH 2/CBH 7 Inhibitory Titer | |
|---|---|---|---|
| | | <1000 | >1000 |
| HCV Sera | 74 | 55 (73%) | 19 (27%) |
| Genotype 1a/1b | 36 | 26 (72%) | 10 (28%) |
| Genotype 2a/2b | 38 | 29 (76%) | 9 (24%) |
| Male/Female | 47/26 | 35/19 | 12/7 |
| Age | Median (N) | 45 (54) | 48 (20) |
| | Range | 31–70 | 40–73 |
| Years HCV + estimated | Median (N) | 5.0 (31) | 5.0 (13) |
| | Range | 0.5–28 | 1–32 |
| Previous Interferon | 18 | 14 (78%) | 4 (22%) |
| Viral Load (GEq/ml) | Median (N) | $4.7 \times 10^6$ (36) | $2.4 \times 10^6$ (16)* |
| | Range | $1.8 \times 10^4$–$2.5 \times 10^7$ | $1.1 \times 10^5$–$6.7 \times 10^6$ |
| ALT | Median (N) | 97 (43) | 124 (15) |
| | Range | 19–4480 | 26–301 |
| Disease Severity (HAI) | Median (N) | 7.5 (31) | 7.0 (11) |
| | Range | 1–11 | 3–13 |
| Cirrhosis | 9 | 8 (86%) | 1 (14%) |

*Significantly different than <1000 group, p = 0.035. Significance testing was performed using the Mann Whitney test.

OTHER EMBODIMENTS

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. An isolated antibody that binds to a conformational epitope of a Hepatitis C virus E2 protein, wherein the epitope is found in Hepatitis C virus of more than one genotype, and wherein the antibody is selected from the group consisting of CBH-2, CBH-4G, CBH-5, CBH-7, CBH-8C, and CBH-11, or binds to the same conformational epitope as that bound by an antibody selected from the group consisting of CBH-2, CBH-4G, CBH-5, CBH-7, CBH-8C, and CBH-11.

2. An isolated antibody that binds to a conformational epitope within amino acids 411 through 644 of E2 protein of Hepatitis C virus 1b, wherein the antibody-binds to the E2 protein of Hepatitis C virus of more than one genotype, wherein the antibody is selected from the group consisting of CBH-2, CBH-5, CBH-8C, and CBH-11, or binds to the same conformational epitope as that bound by an antibody selected from the group consisting of CBH-2, CBH-5, CBH-8C, and CBH-11.

3. An isolated antibody that binds to a conformational epitope within amino acids 470 through 644 of E2 protein of Hepatitis C virus 1b, wherein the antibody is capable of binding to the E2 protein of Hepatitis C virus of more than one genotype, wherein the antibody is CBH-4G or CBH-7, or binds to the same conformational epitope as that bound by CBH-4G or CBH-7.

4. An isolated antibody that binds to the epitope recognized by CBH-2, -4D, -4B, -4G, -5, -7, -8C or -11.

5. The isolated antibody of claim 1 wherein the antibody inhibits binding of HCV E2 protein to CD81.

6. A cell line expressing the isolated antibody of claim 1.

7. The cell line of claim 6 wherein the cell line is a B cell line.

8. The cell line of claim 6 wherein the cell line is a human cell line.

9. The cell line of claim 6 wherein the cell line is a mammalian cell line.

10. The cell line of claim 6 wherein the cell line is a eukaryotic cell line.

11. The cell line of claim 6 wherein the cell line is a hybridoma.

12. The cell line of claim 6 wherein the cell line has been transformed with Epstein-Barr virus (EBV).

13. The cell line of claim 6 wherein the cell line has been infected with a virus.

14. The isolated antibody of claim 1, 2, 3, or 4, wherein the antibody is a monoclonal antibody.

15. The isolated antibody of claim 1, 2, 3, or 4, wherein the antibody is a human antibody.

16. The isolated antibody of claim 1, 2, 3, or 4, wherein the antibody is a humanized antibody.

17. The isolated antibody of claim 1 wherein the antibody is a mammalian antibody.

18. A combination of two or more isolated antibodies wherein at least two of the antibodies bind to different conformational epitopes of E2 protein of Hepatitis C virus of more than one genotype, wherein each antibody is selected from the group consisting of CBH-2, CBH-4G, CBH-5, CBH-7, CBH-8C, and CBH-11, or binds to the same conformational epitope as that bound by an antibody selected from the group consisting of CBH-2, CBH-4G, CBH-5, CBH-7, CBH-8C, and CBH-11.

19. The combination of claim 18, wherein the combination shows increased total binding of the combined antibodies to E2 protein of Hepatitis C virus compared to the binding shown by any of the antibodies individually.

20. The combination of claim 18 comprising CBH-7 and CBH-4G.

21. The combination of claim 18 comprising CBH-7 and CBH-17.

22. The combination of claim 18 comprising CBH-7 and CBH-5.

23. The combination of claim 18 comprising CBH-7 and CBH-2.

24. The combination of claim 19, wherein each antibody in the combination binds to a different epitope.

25. An isolated antibody that binds to a conformational epitope of Hepatitis C virus E2 protein, wherein the antibody is selected from the group consisting of CBH-4B and CBH-4D.

26. A combination of two or more isolated antibodies, at least two of which bind to different conformational epitopes of E2 protein of Hepatitis C virus, wherein each antibody is selected from the group consisting of CBH-4B, CBH-4D, CBH-4G, and CBH-7.

* * * * *

UNITED STATES PATENT AND TRADEMARK OFFICE
CERTIFICATE OF CORRECTION

| | | |
|---|---|---|
| PATENT NO. | : 7,091,324 B2 | Page 1 of 1 |
| APPLICATION NO. | : 09/728720 | |
| DATED | : August 15, 2006 | |
| INVENTOR(S) | : Foung et al. | |

It is certified that error appears in the above-identified patent and that said Letters Patent is hereby corrected as shown below:

In column 1, line 21, delete "DA60596" and insert --DA06596--.

Signed and Sealed this

Nineteenth Day of December, 2006

JON W. DUDAS
*Director of the United States Patent and Trademark Office*